United States Patent
Sun et al.

(10) Patent No.: US 8,679,760 B2
(45) Date of Patent: Mar. 25, 2014

(54) BIOMARKER AND METHOD FOR EVALUATING RISK OF PROLIFERATION, INVASION, OR METASTASIS OF CANCER

(75) Inventors: H. Sunny Sun, Tainan (TW); Jia-Shing Chen, Tainan (TW)

(73) Assignee: National Cheng Kung University, Tainan (TW)

( * ) Notice: Subject to any disclaimer, the term of this patent is extended or adjusted under 35 U.S.C. 154(b) by 103 days.

(21) Appl. No.: 13/099,694

(22) Filed: May 3, 2011

(65) Prior Publication Data

US 2012/0282597 A1 Nov. 8, 2012

(51) Int. Cl.
*C12Q 1/68* (2006.01)
*G01N 33/53* (2006.01)

(52) U.S. Cl.
USPC .......................................... 435/6.14; 435/7.1

(58) Field of Classification Search
None
See application file for complete search history.

(56) References Cited

PUBLICATIONS

Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
Choi-Ying Chiu, et al. "Cloning and Characterization of T-Cell Lymphoma Invasion and Metastasis 2 (TIAM2), a Novel Guanine Necleotide Exchange Factor Related to TIAM1"; Genomics 61; Jul. 15, 1999; p. 66-73; Academic Press.
Yi Ding, et al. "Overexpression of Tiam1 in Hepatocellular Carcinomas Predicts Poor Prognosis of HCC Patients"; Int J Cancer 124; 2009; p. 653-658; 2008 Wiley-Liss, Inc.
Dong Dae Seo, et al. Neural Cadherin Overexpression is a Predictive Marker for Early Postoperative Recurrence in Hepatocellular Carcinoma Patents Journal of Gastroenterology and Hepatology 23, 2008; p. 1112-1118; 2007 Journal of Gastroenterology and Hepatology Foundation and Blackwell Publishing Asia Pty Ltd.
Deng-Fu Yao, et al. "Specific Molecular Markers in Hepatocellular Carcinoma"; Hepatobiliary Pancreat Dis Int.; Jun. 15, 2007; p. 241-247; vol. 6, Issue No. 3.
H. Sunny Sun, Identification of Putative Tumor Suppressor Gene for EBV-Associated NK/T Cell Lymphoma in Taiwan (III), 2004, Institute of Molecular Medicine National Cheng Kung University, Abstract only.
Jia-Shing Chen, Characterization of the Role T-Cell Lymphoma Invasion and Metastasis 2 (TIAM2) in Hepatocellular Carcinoma, Electronic Theses and Dissertations Service, 2010, National Cheng Kung University, Abstract only.

* cited by examiner

*Primary Examiner* — James Martinell
(74) *Attorney, Agent, or Firm* — Bacon & Thomas, PLLC

(57) ABSTRACT

The present invention relates to a biomarker associated with a cancer and a method using the biomarker to evaluate a risk of proliferation, invasion, or metastasis of a cancer. The method of the present invention comprises the following steps: (A) providing a tissue sample to evaluate for risk of proliferation, invasion, or metastasis of a cancer, wherein the tissue sample comprises a non-cancer region, and a suspected cancer region; (B) detecting expression levels of a biomarker and a predetermined standard in the non-cancer region and the suspected cancer region respectively, wherein the biomarker is T-cell lymphoma invasion and metastasis 2 (TIAM2); (C) comparing the expression levels of the biomarker and the predetermined standard in the non-cancer region to the expression levels of the biomarker and the predetermined standard in the suspected cancer region.

9 Claims, 8 Drawing Sheets

BIOMARKER AND METHOD FOR EVALUATING RISK OF PROLIFERATION, INVASION, OR METASTASIS OF CANCER

BACKGROUND OF THE INVENTION

1. Field of the Invention

The present invention relates to a biomarker associated with a cancer and a method using the biomarker to evaluate the risk of proliferation, invasion, or metastasis of a cancer and, more particularly, to a biomarker and a method using the biomarker which can be used to evaluate the risk of proliferation, invasion, or metastasis of cancer in an early stage.

2. Description of Related Art

In recent years, it is found that foods or food additives, and environmental pollutions are blamed for directly causing cancer. It is also found that not only in Taiwan, but also in the developed countries around the whole world, the incidence rates of cancers are quite high. Additionally, according to the data published by the American Cancer Society, cancer is perhaps the most significant threat to public health.

If the proliferation, invasion, or metastasis of cancers can be detected in the early stage, the survival rate of patients with cancers can be greatly increased. Hence, many studies focus on developing methods for analyzing or predicting cancers in the early stage. Currently, as the developments of gene profiling and proteomics, biomarkers for analyzing or predicting cancers are well developed, such as α-fetoprotein (AFP), T-cell lymphoma invasion and metastasis 1 (TIAM1), and N-cadherin.

However, all of them are applied with limitations. For example, AFP is a useful serological marker for diagnosis of hepatocellular carcinoma (HCC), but it showed 40% false-negative. Furthermore, up-regulation of N-cadherin is only correlated with recurrence after surgery, and TIAM1 overexpression was observed in 63.8% poor prognosis of HCC patients. Besides, since these proteins also expresses in normal liver tissue, the determination of pathological overexpression of given protein may not be easy. Hence, it is desirable to provide a biomarker and a method using the biomarker, which can improve the accuracy of predicting the risk of proliferation, invasion, or metastasis of a cancer.

In addition, hepatocellular carcinoma (HCC), i.e. liver cancer, is the fifth-most common cancer worldwide and shows high prevalence in Asia and Africa. Despite the heterogeneous etiology, one unique feature of HCC is its aggressiveness with early vascular invasion and metastasis. If the proliferation and the invasion/metastasis in hepatocellular carcinoma can be predicted in the early stage, the incidence rate and the mortality of the liver cancer can be greatly decreased. Therefore, it is also desirable to provide a biomarker and a method using the biomarker, which can predict the risk of proliferation, invasion, or metastasis of a liver cancer precisely.

SUMMARY OF THE INVENTION

The object of the present invention is to provide a method for evaluating a risk of proliferation, invasion, or metastasis of a cancer, so the risk of proliferation, invasion, or metastasis of a cancer can be predicted precisely through the method of the present invention.

Another object of the present invention is to provide a biomarker for evaluating a risk of proliferation, invasion, or metastasis of a cancer, which can be used to evaluate whether a tissue in a suspected cancer region is a cancer tissue or not.

To achieve the object, the method for evaluating risk of proliferation, invasion, or metastasis of a cancer of the present invention comprises the following steps: (A) providing a tissue sample to evaluate for risk of proliferation, invasion, or metastasis of a cancer, wherein the tissue sample comprises a non-cancer region, and a suspected cancer region, and the tissue sample is preferably selected from the group consisting of liver tissue, breast tissue, pancreas tissue, brain tissue, thymus tissue, prostate tissue, colon tissue, or other solid tissues; (B) detecting expression levels of a biomarker and a predetermined standard in the non-cancer region and the suspected cancer region respectively, wherein the biomarker is T-cell lymphoma invasion and metastasis 2 (TIAM2); (C) comparing the expression levels of the biomarker and the predetermined standard in the non-cancer region to the expression levels of the biomarker and the predetermined standard in the suspected cancer region through the following equation (I):

$$\text{Value} = \frac{\text{(the expression level of the biomarker in the suspected cancer region)}}{\text{(the expression level of the predetermined standard in the suspected cancer region)}} - \frac{\text{(the expression level of the biomarker in the non-cancer region)}}{\text{(the expression level of the predetermined standard in the non-cancer region)}} \quad \text{[Equation (I)]}$$

wherein when the value is positive, this indicates high risk of proliferation, invasion, or metastasis of liver cancer, breast cancer, thymus cancer, prostate cancer, colon cancer, pancreas cancer, or other solid cancers; and when the value is negative, this indicates high risk of proliferation, invasion, or metastasis of brain cancer.

In addition, the present invention also provides a biomarker for evaluating risk of proliferation, invasion, or metastasis of a cancer, which is selected from the group consisting of nucleotides, a complementary of the nucleotides, a derivative of the nucleotides, a protein, a derivative of the protein, a peptide of the protein, a mutation of the protein of TIAM2.

Preferably, the biomarker of TIAM2 protein was used in the method of the present invention.

When the method of the present invention is used to evaluate whether a person is at a risk of proliferation, invasion, or metastasis of a cancer or not, the prediction accuracy can be greatly improved. In addition, the present invention also provides a novel biomarker, TIAM2, which expresses specifically in tumor cells. Hence, when the biomarker of the present invention is used to evaluate whether a person is at a risk of proliferation, invasion, or metastasis of a cancer or not, the prediction accuracy can be further improved. More especially, the method and the biomarker of the present invention can be used to evaluate the risk of the invasion or metastasis of a solid cancer, which cannot be accomplished by the conventional method and biomarker. Hence, the method and the biomarker of the present invention can predict the severity of the solid cancer in an early stage, and thereby doctors can provide effective treatment to patients to delay the invasion or metastasis of tumor cells into vessels.

According to the method of the present invention, the non-cancer region means a region of normal tissue. Preferably, the non-cancer region is surrounded around the suspected cancer region. In addition, the risk means a possibility that the cells in the suspected cancer region are tumor cells, or a possibility that a person to be evaluated suffers from a cancer. In addition, when the value is positive, this indicates that the suspected cancer region is a cancer region, i.e. a region of tumor tissue, and the person is at risk of proliferation, invasion, or metastasis of a cancer. Furthermore, the method of the present invention can be used to predict not only the proliferation of a cancer, but also the invasion or metastasis of a cancer. When the value is positive/negative, this indicates that the tumor cells may invade or metastasize into blood vessels. The invasion or metastasis of the tumor cells may cause the cancer become severe, and metastatic cancers may be developed.

In addition, according to the method and the biomarker of the present invention, TIAM2 is T-cell lymphoma invasion and metastasis 2 short fowl (TIAM2S), or T-cell lymphoma invasion and metastasis 2 long form (TIAM2L). Preferably, TIAM2 is TIAM2S. In addition, according to the method and the biomarker of the present invention, the sequence of the nucleotides of TIAM2 is SEQ ID NO: 1, the sequence (i.e. the expressed sequence) of the nucleotides of TIAM2S is SEQ ID NO: 2, and the sequence of the protein of TIAM2S is SEQ ID NO: 3.

According to the biomarker and the method of the present invention, cancer may be liver cancer, breast cancer, pancreas cancer, brain cancer, thymus cancer, prostate cancer, colon cancer, or other solid cancers. Preferably, the cancer is liver cancer.

In addition, according to the method of the present invention, the tissue sample may be any tissue nodule to be detected. For example, the tissue sample can be nodules of liver, breast, pancreas, brain, thymus, prostate, colon, or other tissues. Preferably, the tissue sample is liver nodules.

Furthermore, according to the method of the present invention, the expression level may be a protein expression level, or an mRNA expression level.

When the expression level is a protein expression level, it can be detected through any conventional analysis for protein expression. Preferably, the protein expression level is detected through Western blot analysis, Gel electrophoresis, Enzyme-linked immunosorbent assay (ELISA), Immunohistochemistry (IHC), Immunoprecipitation (IP), or Mass spectrum analysis (MS). More preferably, the protein expression level is detected through Western blot analysis. In addition, the predetermined standard used in the analysis for protein expression can be α-tubulin, Glyceraldehyde 3-phosphate dehydrogenase (GAPDH), or β-actin. Preferably, the predetermined standard is α-tubulin, or β-actin. More preferably, the predetermined standard is α-tubulin.

When the expression level is an mRNA expression level, it can be detected through any conventional analysis for RNA expression. Preferably, the mRNA expression level is detected through quantitative real-time reverse transcription PCR, or reverse transcription PCR. More preferably, the mRNA expression level is detected through quantitative real-time reverse transcription PCR. In addition, the predetermined standard used in the analysis for mRNA expression can be 18S ribosomal RNA, α-tubulin mRNA, Glyceraldehyde 3-phosphate dehydrogenase (GAPDH) mRNA, or β-actin mRNA. More preferably, the predetermined standard is 18S ribosomal RNA.

Other objects, advantages, and novel features of the invention will become more apparent from the following detailed description when taken in conjunction with the accompanying drawings.

DETAILED DESCRIPTION OF THE PREFERRED EMBODIMENT

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

Figure 1:
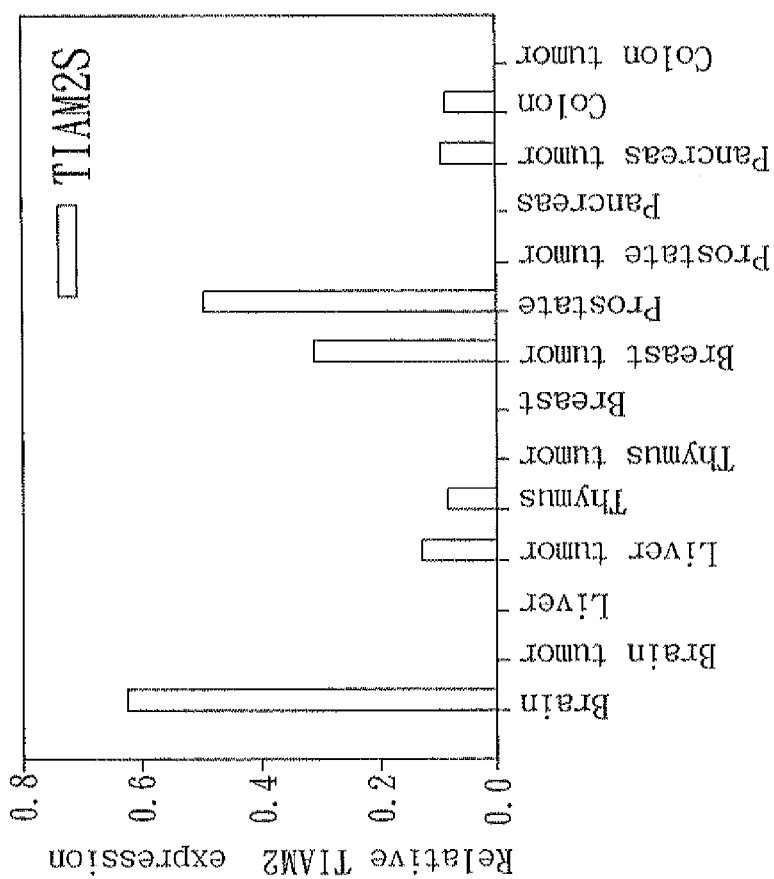
FIG. 1 is a diagram showing the results of the expression of TIAM2S mRNA in normal and tumor tissues of brain, liver, thymus, breast, prostate, pancreas, and colon.

Identification of Endogenous TIAM2S Expressions in Normal Tissues And Tumor Tissues with Semi-Quantitative RT-PCR and Western Blot The cDNA panels for different human tissues including normal brain tissue, brain tumor tissue, normal liver tissue, liver tumor tissue, normal thymus tissue, thymus tumor tissue, normal breast tissue, breast tumor tissue, normal prostate tissue, prostate tumor tissue, normal pancreas tissue, pancreas tumor tissue, normal colon tissue, and colon tumor tissue were purchased from Clontech (Palo Alto, Calif.) and (Biochain, Hayward, Calif.). TIAM2S-specific PCR primers were used to amplify TIAM2S. The PCR parameters were 95° C. for 5 minutes followed by 30 cycles of amplification at 95° C. for 30 seconds, 64° C. for 20 seconds, and 72° C. for 20 seconds, with a final extension at 72° C. for 10 minutes. The PCR products were separated on 8% acrylamide gel. The relative expression levels of TIAM2S in different tissues were measured from each PCR product by spot density function using Alphaimage 1200 (Alpha Innotech Corporation, San Leandro, Calif.), and normalized by the density of 200 bp band of the 1 Kb plus DNA marker (Invitrogen). The results of the expression of mRNA in each tissue are shown in FIG. 1. In addition, normal human tissues including normal brain tissue, normal liver tissue, normal thymus tissue, normal breast tissue, normal prostate tissue, normal pancreas tissue, and normal colon tissue also were purchased from (Biochain, Hayward, Calif.). Antibodies used for Western blot were purchased as follows: rabbit anti-α-tubulin, from Cell Signaling Technology (MA, USA); goat anti-TIAM2 antibodies from Santa Cruz Biotech (CA, USA).

The Western blot analysis was performed as follow. First, 30 μg of protein was injected into 6% SDS-PAGE in Tris-glycine-SDS buffer (10 mM Tris, 50 mM glycine, 0.1% SDS, pH 8.0), and separated with electrophoresis. Then, the proteins on the SDS-PAGE were transferred onto PVDF membranes, and the membranes were blocked in TBST (10 mM Tris-HCl, pH7.5, 150 mM NaCl, and 0.05% Tween 20) containing 5% non-fat milk for at least 1 hour and incubated overnight with primary TIAM2S antibodies. The membranes were washed four times in TBST and incubated with horseradish peroxidase-conjugated secondary antibody for 2 hour. After washing and staining the membranes, the signals on the membranes were detected with an enhanced chemiluminescence (ECL) system (PerkinElmer Life Science, Waltham, Mass.). In the experiment of the Western blot analysis, α-tubulin was used as a control for analyzing the total amount of the TIAM2S proteins.

As shown in the results of FIG. 1, the expression of TIAM2S mRNA was detected in liver tumor tissue, breast tumor tissue, and pancreas tumor tissue. However, the expression of TIAM2S mRNA was not detected in normal liver tissue, normal breast tissue, and normal pancreas tissue. On the contrary, the expression of TIAM2S mRNA was detected in normal brain tissue, normal thymus tissue, normal prostate tissue, and normal colon tissue, but not detected in brain tumor tissue, thymus tumor tissue, prostate tumor tissue, and colon tumor tissue. Furthermore, only normal human brain was detected with abundant TIAM2S protein expression which indicated the expression of TIAM2S protein may be controlled by special translational regulation. Taken together, these results indicate that the aberrant mRNA expression of TIAM2S is observed in many solid tumors which indicated TIAM2S is a potential tumor associated gene and the final gene product of TIAM2S protein is more suitable to be a marker than TIAM2S mRNA.

Collection of HCC Specimens

A total of 88 paired (tumor part and matched non-tumor part) and 3 metastatic HCC samples were collected from patients with liver cancers (mean age 57.9±15.6, ranging from 13 to 85 years) undergoing surgical operation. Among them, 28 and 59 pairs were collected from the Department of Surgery, National Cheng Kung University Hospital and the Taiwan Liver Cancer Network (TLCN), respectively. Diagnosis of liver cancer was confirmed by histological examination. Sample collection protocols were approved by the IRB Committees and informed consents were obtained from patients. Tissues were taken separately from cancerous and surrounding normal parts of the resected specimens and were immediately frozen until further processed for nucleic acid and protein extractions. An additional seven metastatic HCC specimens from four individual patients were collected from the Tumor Tissue Bank in the Department of Pathology, National Cheng Kung University Hospital and 30 benign hemangiomas (8 males and 22 females) were from TLCN as negative controls. Among the 91 paired HCC samples, 32 paired samples (35%) were under pathologic stage I, 26 paired samples (29%) were under pathologic stage II, and 25 paired samples (27%) were under pathologic stage III.

Identification of TIAM2S mRNA Expression in HCC Cells with Quantitative Real-Time RT-PCR Total RNA from frozen specimens of HCCs were isolated using Rezol C&T (Protech Technology, Taipei, Taiwan) according to the manufacturer's protocol. qRT-PCR of TIAM2S and 18S ribosomal RNA (18S rRNA) was performed with TaqMan assays (Applied Biosystems, Foster City, Calif.) according to the manufacturer's protocol. The levels of TIAM2S mRNA expression in each of the HCC tumor samples were measured (i.e., the $2^{-\Delta\Delta C_t}$ method) and normalized to the expression level of the normal part from each specimen. All measurements were performed in triplicate and the experiments were repeated at least twice. Twenty pairs of HCC samples were used to examine the ectopic expression of TIAM2S mRNA in HCC cells, and the mRNA expression level of TIAM2S in each tumor cell was normalized to its normal counterpart, 18S rRNA. The results of the TIAM2S mRNA expression in HCC cells are shown in FIG. 2.

Figure 2:
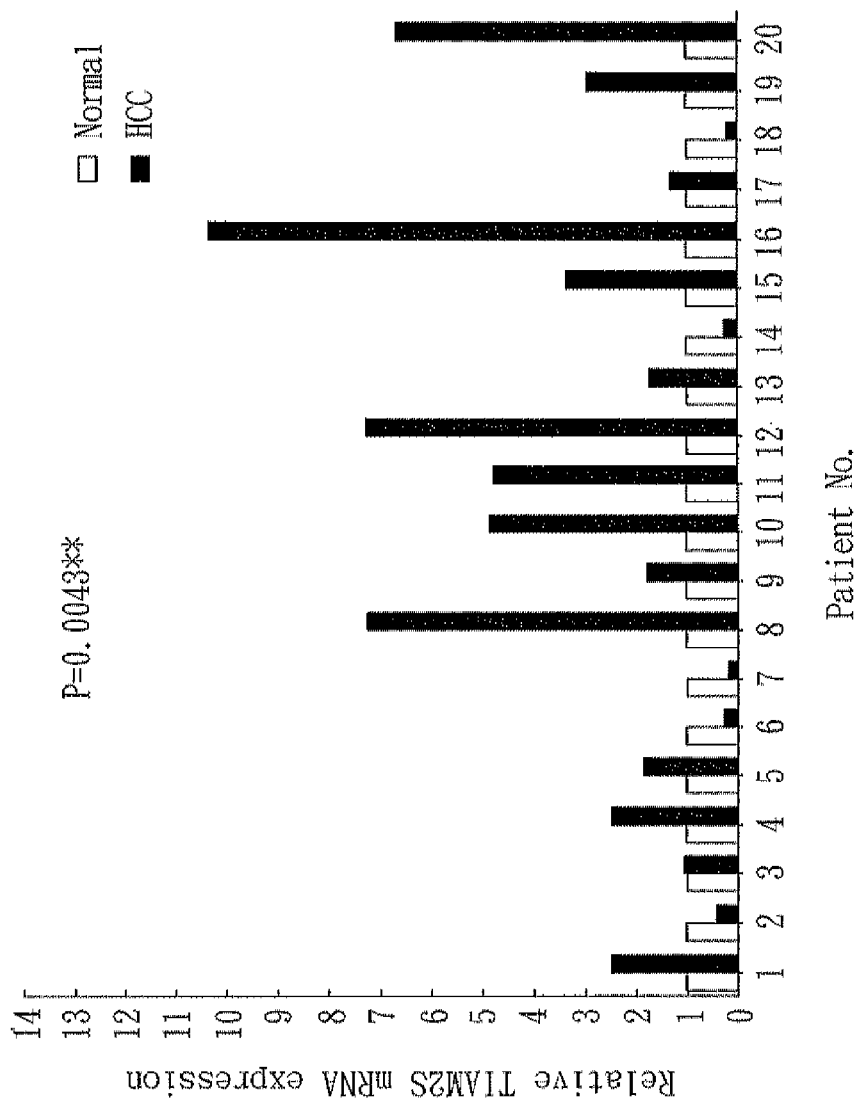
FIG. 2 is a diagram showing the results of the expression of TIAM2S mRNA in HCC cells.

As shown in the results of FIG. 2, the TIAM2S mRNA expression in HCC cells is higher than that in normal tissue, and especially the results from paired-t test demonstrated that TIAM2S mRNA is significantly expressed in tumor cells (**: P=0.0043). In addition, examination of TIAM2S mRNA in 20 paired HCC cells revealed that 65% (13/20) of HCC cells showed an increase (from 2- to 9-fold) of TIAM2S mRNA in tumor.

Identification of TIAM2S Protein Expression in HCC Cells with Western Blot Analysis Approximately 150 mg of the aforementioned HCC samples was dissected and snap-frozen in liquid nitrogen. The frozen samples were added to 1 mL RIPA buffer (50 mM Tris, pH 8.0, 150 mM NaCl, 1% Triton X-100, 0.5% sodium deoxycholate, 0.1% SDS, 1 mM PMSF and the cocktail of protease inhibitors) and homogenized by using tissue grinder immediately on ice. The lysate was rinsed twice with 1 mL RIPA buffer and constantly agitated at 4° C. for 20 min to maintain homogenization, followed by centrifugation for 20 minutes at 19,600×g at 4° C. The supernatants were collected and subjected to western blot analysis.

The results of the Western blot analysis show that TIAM2S protein only express in tumor cells, but does not express in normal cells. In addition, none or trace amounts of TIAM2S protein were detected in the hemangiomas. These results indicate that TIAM2S protein specifically express in HCC cells.

In addition, the Western blot density of TIAM2S protein in HCC cells and normal cells from each patient was normalized to that of α-tubulin in HCC cells and normal cells respectively. Herein, the Western-blot density of TIAM2S and α-tubulin in HCC cells and normal cells has to be from the same patient. The normalization was performed by the following equation (II), and the density and the value are summarized in the following Table 1.

Value=[(the density of TIAM2S protein in HCC cells/ the density of α-tubulin in HCC cells)−(the density of TIAM2S protein in normal liver cells/the density of α-tubulin in the normal liver cells)]   [Equation (II)]

TABLE 1

| Patient No. | Normal liver cells | | HCC cells | | Value |
| --- | --- | --- | --- | --- | --- |
| | TIAM2S | α-tubulin | TIAM2S | α-tubulin | |
| 1 | 0.2 | 4. | 5.9 | 5.5 | 1.02 |
| 2 | 0.3 | 4.1 | 8.2 | 5.9 | 1.32 |
| 3 | 0.3 | 3.1 | 0.4 | 3.6 | 0.01 |
| 4 | 0.2 | 4.8 | 2.7 | 5.2 | 0.48 |
| 5 | 0.2 | 3 | 5.8 | 4.6 | 1.19 |
| 6 | 0.3 | 4.7 | 1.7 | 6.8 | 1.19 |

Value: the density of ectopic expression of TIAM2S protein

As shown in Table 1, the values of each paired sample are shown in positive, which means that the TIAM2S protein expression is positively related to the formation of liver cancer.

Figure 3:
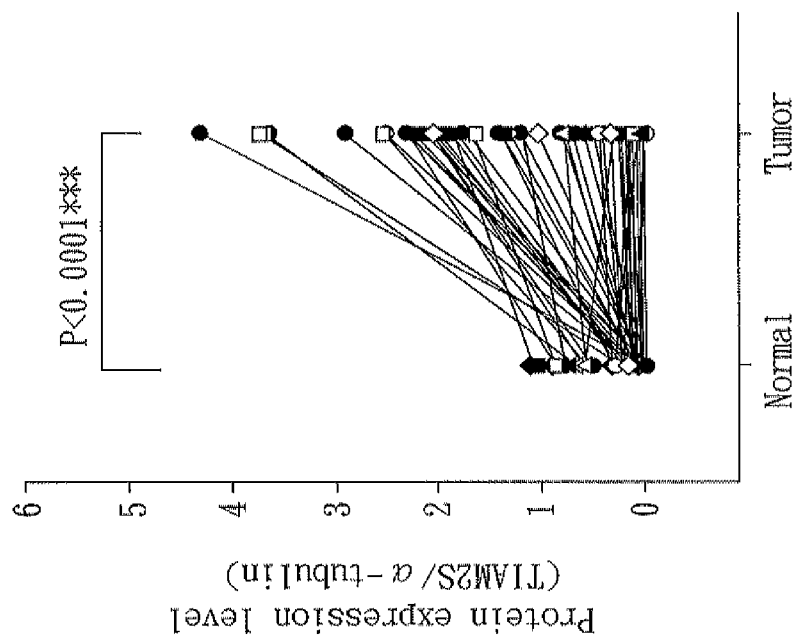
FIG. 3 is a diagram showing the quantified results from Western blot analysis.

Furthermore, FIG. 3 is a plot showing the results from Western blot analysis of 69-paired HCCs, which were quantified with spot density function using alpha-imager system. After 69 HCC samples were detected with Western blot analysis, the results indicate that 60 (87%) HCC samples showed aberrant TIAM2S protein expression in tumor cell, and the paired-t test shows that the ectopic expression of TIAM2S is significant in HCC cells (***: P<0.0001).

Figure 4:
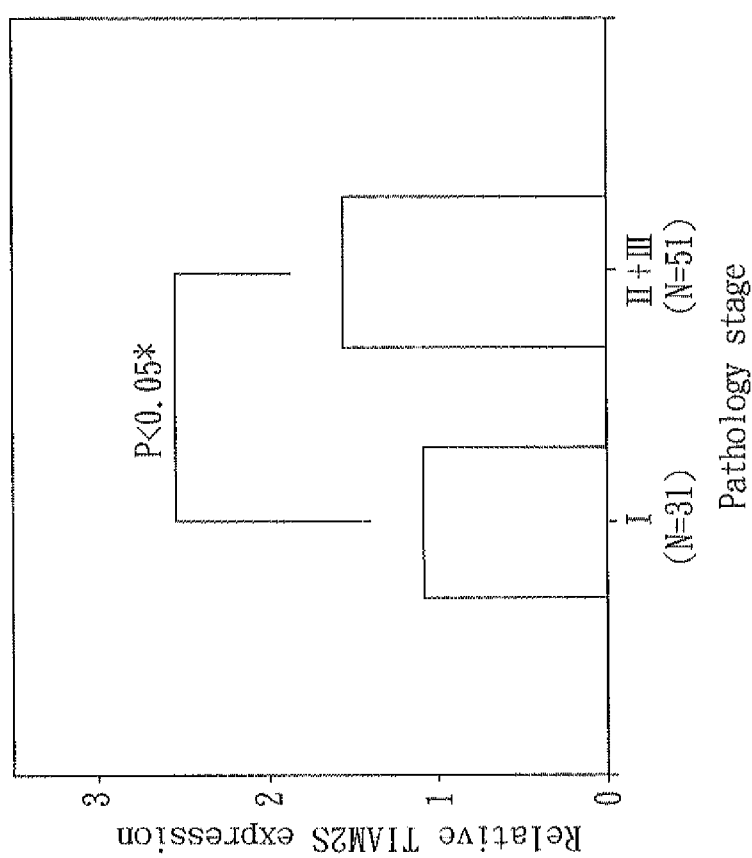
FIG. 4 is a diagram showing the correlation of TIAM2S protein expression in HCC samples with different pathology stages.

In addition, the correlations between TIAM2S expression levels and various clinical features were also analyzed. If the HCC samples are under stages II and/or III, it indicates that the probability of tumor invasion into vessels is high. Therefore, the risk of invasion/metastasis of tumor cells is increased. As shown in FIG. 4, the expression of TIAM2S protein was increased in HCC samples with the invasive phenotype (stage II and III), but not in those with the non-invasive phenotype (stage I, *: P<0.05). According to the results shown in FIG. 4, the TIAM2S indeed can be used as a biomarker to evaluate the risk of invasion or metastasis of tumor, especially liver cancer.

According to the aforementioned results, the method of the present invention, which uses TIAM2S as a biomarker to evaluate a risk of proliferation of a liver cancer, has high accuracy (87%). However, the method using AFP as a biomarker has an accuracy of about 50%. Hence, the method of the present invention has higher accuracy than that using AFP as a biomarker. In addition, the biomarker TIAM2S of the present invention can also be used to evaluate a risk of invasion/metastasis of a liver cancer, which cannot be accomplished by the conventional biomarker AFP.

Cell Proliferation Assay

The human hepatoma cell line, HepG2, was used to generate stable cloned cell lines for overexpression of recombinant TIAM2S. One control clone of HepG2/pcDNA3.1A+ (V1A3) and two independent clones of HepG2/pcDNA3.1A+_TIAM2S (T1A1 and T2C1) were obtained after selection for 30 days using G418. Cells were maintained at 37° C. in a humidified atmosphere of 5% $CO_2$ in α-MEM supplemented with 100 U/mL penicillin, 100 μg/mL streptomycin, 700 μg/mL G418, and 10% FBS for further applications.

Cell proliferation was measured using a colorimetric assay according to the manufacturer's protocol (CellTiter 96 Aqueous One Solution cell proliferation assay; Promega, Madison, Wis.). In brief, stable clones were seeded at $5 \times 10^3$ cells/well in 96-well culture plates (each group had four wells). The effect of overexpression of TIAM2S on cell growth was determined at various time points. The intensity of the color was measured at 490 nm using a 96-well microplate reader (Labsystems, Multiskan EX, Helsinki, Finland). The corrected absorbance (after subtracting the control blanks) was used to determine the proliferative response. All experiments were independently repeated at least three times. The relative proliferation rates of stable clones carrying control vector (V1A3) and recombinant TIAM2S (T1A1 and T2C1) are shown in FIG. 5.

Figure 5:
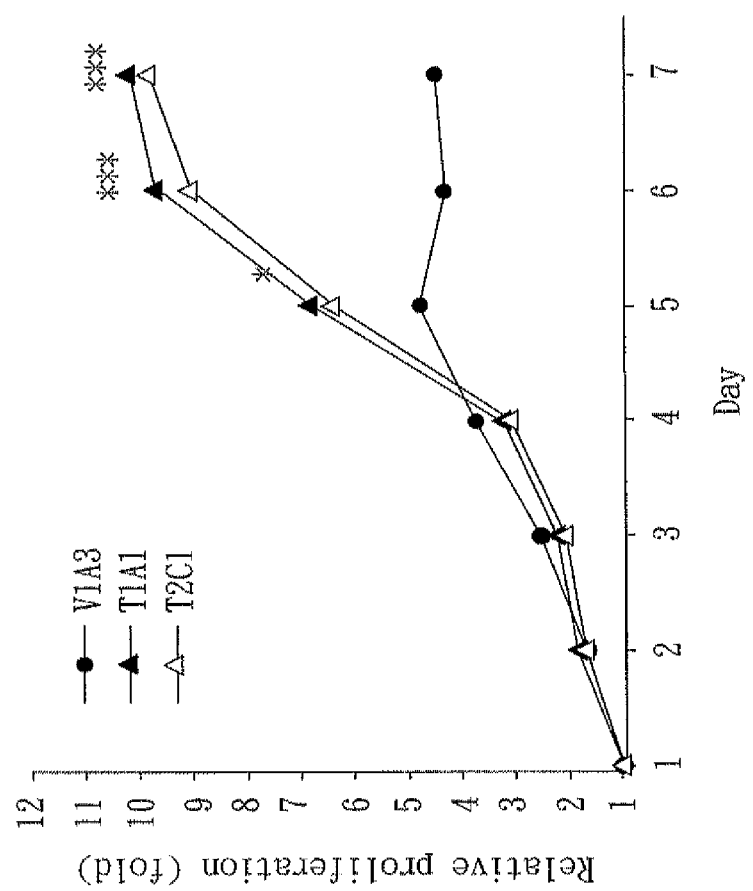
FIG. 5 is a diagram showing the results of a cell proliferation assay.

According to the results shown in FIG. 5, HepG2-TIAM2S cells (T1A1 and T2C1) continued to grow while HepG2-control cells (V1A3) stopped growing after day 4 (*: P<0.05, : P<0.01, *: P<0.001). It means that stable expression of recombinant protein, HepG2-TIAM2S cells, promotes the growth ability in HepG2 cells (a low dedifferentiated HCC cell line).

Cell Invasion Assay

The aforementioned control clone of HepG2/pcDNA3.1A+ (V1A3) and independent clones of HepG2/pcDNA3.1A+_TIAM2S (T1A1 and T2C1) were used in the present experiment. A transwell with an 8-μm pore size polycarbonate membrane filter (Millipore, Temecula, Calif.) was coated with a uniform layer of 15.15 μg/cm² Matrigel basement membrane matrix. The coated transwell was air-dried completely. Before carrying out the experiment, the Matrigel was reconstituted by adding 40 μL α-MEM with 0.1% FBS and incubated at 37° C. for 1 hour. Trypsinized cells ($1.5 \times 10^5$) were suspended in 100 μL α-MEM with 0.1% FBS and added into the upper camber of the transwell. α-MEM (700 μL) containing 10% FBS was added to the lower camber. After 24 hours of incubation, the non-invading cells and the upper side of the pore membrane were removed with a cotton swab. The cells on the lower surface of the membrane were fixed for 15 minutes with methanol and stained with 0.2% crystal violet for 30 minutes. The invading cells were counted by dividing the membrane area into five fields and visualizing the fields at 200× magnification.

Figure 6:
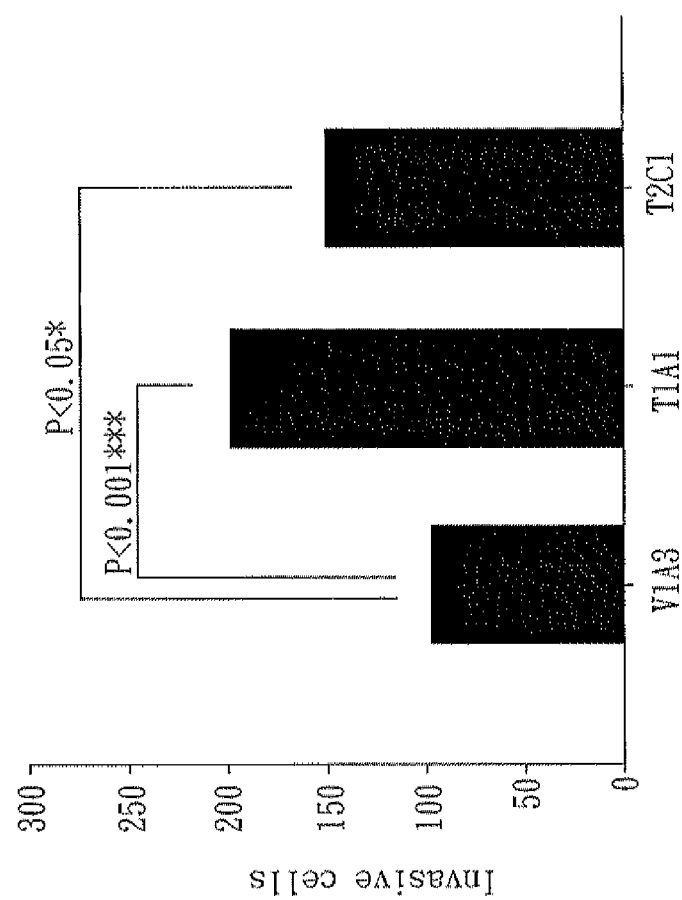
FIG. 6 is a diagram showing the results of a cell invasion assay.

The sum number of the violated stained cells from five randomly selected fields on the transwell is shown in FIG. 6 (*: P<0.05, : P<0.01, *: P<0.001). As shown in FIG. 6, the number of invaded cells was greater in T1A1 (P<0.001) and T2C1 (P<0.05) cells than in control V1A3 cells. Thus, the data revealed that TIAM2S increased the invasive ability of HepG2 cells, and it suggests that TIAM2S is involved in promoting growth and increasing invasiveness in TIAM2S-expressing cells.

In Vivo Tumorigenicity Assay

The control (V1A3) and TIAM2S stable clones (T1A1 and T2C1) were subcutaneously injected into 8-week-old ICR nu/nu mice to examine the tumorigenicity. About $5 \times 10^6$ cells from individual cloned cell lines were injected (in 0.2 μL PBS) subcutaneously into the dorsal region using a 27-gauge needle. Nine mice were used for each cell line and the tumors were palpated weekly after inoculation. Tumor volumes were measured after 3 weeks using a caliper (calculated as length×width×height×0.52) until the tumor volume reached 1,000 mm³ or after 8 weeks. The mice were then euthanized; tumors were excised and embedded in OCT. HE-stained sections from various excised tumors were evaluated for invasion ability. The results are shown in FIGS. 7A-7C.

Figure 7B:
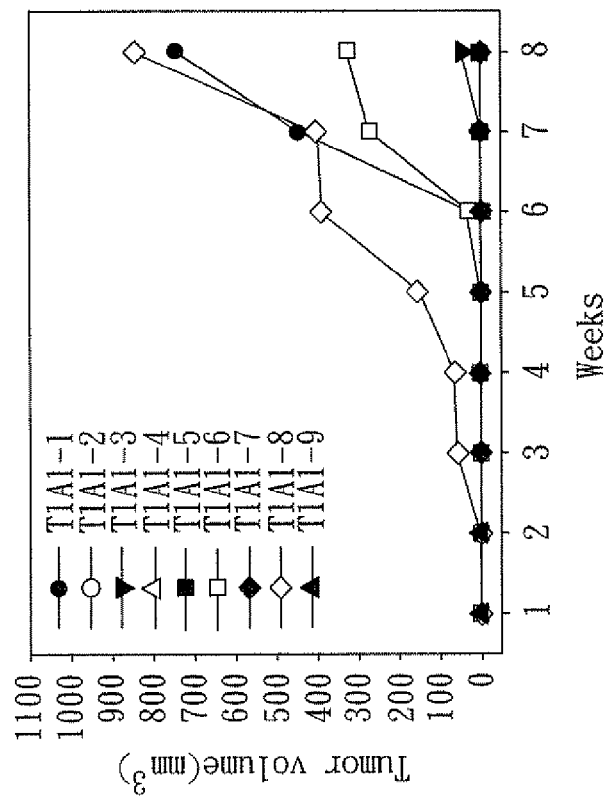
FIGS. 7A-7C are diagrams showing the results of in vivo tumorigenicity assay.
Figure 7A:
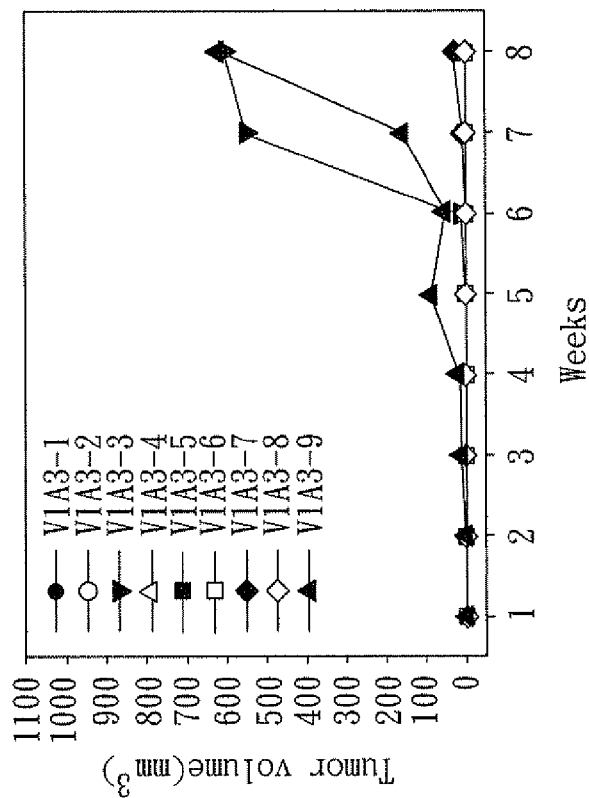
Figure 7C:
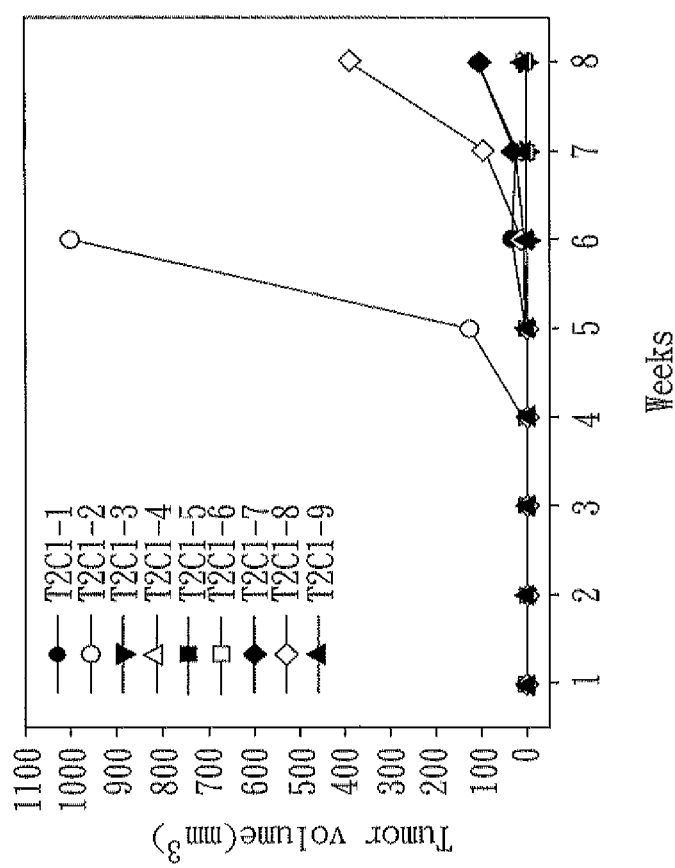

FIG. 7A shows the Xenograft tumor volume in mice injected with control clones (V1A3), FIG. 7B shows the Xenograft tumor volume in mice injected with TIAM2S stable clones (T1A1), and FIG. 7C shows the Xenograft tumor volume in mice injected with TIAM2S stable clones (T2C1).

As shown in FIGS. 7A-7C, the total number of tumor-growing mice was slightly higher in the TIAM2S group (9/18; 50%) than in the control group (3/9; 33%). Compared to the TIAM2S-expressing group, tumors grown from the control group were round and smooth and they were more easily stripped and dissociated from the adjacent tissues. In contrast, tumors grown from the TIAM2S-expressing group were multi-module with rough edges and were hard to separate from the adjacent tissues. The ratio of tumors showing the invasive phenotype was 0% (0/3) and 55.6% (5/9), respectively, in the control and TIAM2S groups. Recombinant TIAM2S expression was detected in tumors grown from TIAM2S-expressing cells but not from control cells.

In addition, results of histological analysis demonstrated that TIAM2S-expressing tumors tightly contacted or even penetrated into the surrounding skeletal muscle layer and showed an unclear boundary. In contrast, tumors grown from the control group showed clear boundaries between tumor and stroma cells and showed no connection with neighboring skeletal muscle. These data are in agreement with the cellular tumorigenic assays and further support the role of TIAM2S expression in promoting cell growth and invasion.

According to the results of the cell proliferation assay, the cell invasion assay and the in vivo tumorigenicity assay, the expression of TIAM2S may increase the invasive ability, so it may play a role in cancer metastasis. Therefore, the biomarker of the present invention, TIAM2S, can be used not only to evaluate a risk of proliferating a cancer, but also to predict the invasive and metastasis ability of a cancer.

Although the present invention has been explained in relation to its preferred embodiment, it is to be understood that many other possible modifications and variations can be made without departing from the spirit and scope of the invention as hereinafter claimed.

What is claimed is:

1. A method for evaluating risk of proliferation, invasion, or metastasis of a cancer, comprising the following steps:
   (A) providing a tissue sample to evaluate for risk of proliferation, invasion, or metastasis of a cancer, wherein the tissue sample comprises a non-cancer region, and a suspected cancer region, and the tissue sample is one selected from the group consisting of liver tissue, breast tissue, pancreas tissue, brain tissue, thymus tissue, prostate tissue, and colon tissue;
   (B) detecting expression levels of a biomarker and a predetermined standard in the non-cancer region and the suspected cancer region respectively, wherein the biomarker is T-cell lymphoma invasion and metastasis 2 (TIAM2);
   (C) comparing the expression levels of the biomarker and the predetermined standard in the non-cancer region to the expression levels of the biomarker and the predetermined standard in the suspected cancer region through the following equation (I):

Value=(the expression level of the biomarker in the suspected cancer region/the expression level of the predetermined standard in the suspected cancer region)−(the expression level of the biomarker in the non-cancer region/the expression level of the predetermined standard in the non-cancer region)  [Equation (I)]

wherein when the value is positive, this indicates high risk of proliferation, invasion, or metastasis of liver cancer, breast cancer, thymus cancer, prostate cancer, colon cancer, pancreas cancer, or other solid cancers; and when the value is negative, this indicates high risk of proliferation, invasion, or metastasis of brain cancer.

2. The method as claimed in claim 1, wherein the TIAM2 is T-cell lymphoma invasion and metastasis 2 short form (TIAM2S).

3. The method as claimed in claim 2, wherein the biomarker is selected from the group consisting of nucleotides, a complementary of the nucleotides, a protein, and a peptide of the protein of TIAM2S.

4. The method as claimed in claim 1, wherein the cancer is liver cancer.

5. The method as claimed in claim 1, wherein the tissue sample is tissue nodules.

6. The method as claimed in claim 5, wherein the tissue sample is liver nodules.

7. The method as claimed in claim 1, wherein the expression level is a protein expression level.

8. The method as claimed in claim 7, wherein the protein expression levels are detected through Western blot analysis, Gel electrophoresis, Enzyme-linked immunosorbent assay (ELISA), Immunohistochemistry (IHC), Immunoprecipitation (IP), or Mass spectrum analysis (MS).

9. The method as claimed in claim 8, wherein the predetermined standard is α-tubulin, Glyceraldehyde 3-phosphate dehydrogenase (GAPDH), or β-actin.

* * * * *

SEQUENCE LISTING

<160> NUMBER OF SEQ ID NOS: 3

<210> SEQ ID NO 1
<211> LENGTH: 167435
<212> TYPE: DNA
<213> ORGANISM: Homo sapiens

<400> SEQUENCE: 1

| | | | | | | |
|---|---|---|---|---|---|---|
| ggctctgtgt | atgaatgaca | aggatacctt | cagccagctc | attctggatg | aatgaatgat | 60 |
| tacactaagt | gtcctccaca | ttcctctgtg | ggtaagtttg | aggcacttgt | atatctcaaa | 120 |
| ggctttaaaa | gtatatgtca | gtctgtattt | ctttgcttaa | tcaccacatt | ctcacgtagc | 180 |
| tctgttaatt | gcactttgta | tgagaagttg | agtggggaaa | gccaaagcag | gtttgctgaa | 240 |
| tgctgataat | tgaggttcct | gcaagcaaca | gggctccaga | gctcagtaga | ttattacaaa | 300 |
| agcactttaa | ttagatatgc | tggatggtcc | actcagtgtg | gaaaacgggt | atgccaggcc | 360 |
| tctctgggac | cttaggtgga | gaggatgcag | cctgggcagc | tttagtttcc | gtccttttat | 420 |
| gtgccacata | ctgatagagc | acacacttaa | actccagacc | aaataggacc | tcctgcttga | 480 |
| gaacgcagag | agcatataat | ttctaattgg | agttgtaaga | tcaggtaagc | tcaggggacg | 540 |
| gggattttag | gaagccactg | aggaaaggtc | agattccaac | tgtgacctta | aggctgtttc | 600 |
| attccgactg | aggtgtttta | ctgattggat | gtgttggtgt | cgcaggttaa | gtactaaagc | 660 |
| aggaaagctg | aacagttccc | cagcggcgtt | tgaaatggtg | gcaggtagtt | ccctggactg | 720 |
| tttgccgtgt | ctggagttcg | tgcgtgctta | gctgaagcac | gctcagatga | acataacctt | 780 |
| cccaggcata | accttctgct | gttttgattta | gattgcccca | gcttttcttg | gctgattgct | 840 |
| tcatgctttt | tgggtttcag | ctcaaagtac | tccctctgaa | ggacgctgac | cacccaatct | 900 |
| aaaggacgcc | cagccactgc | taccacgcca | cgctctctta | gttgcctgca | aagtccttgt | 960 |
| ccctcactga | tcgttttctc | cttgcatatt | tatgtatcgg | cttgttgtct | gtctccgcct | 1020 |
| tccttagagc | agaagctcca | caagggcagg | aaccttctct | gcctggttcc | tcacctgtct | 1080 |
| ccagagccca | caacagcatc | tgttgcacag | cagatatgtt | ttgtctgaat | gtatgagttg | 1140 |
| aacggttaaa | tgaggctcat | tgtgtaaatt | gctcaatgtc | acatggtgag | atacttattc | 1200 |
| acactggagg | atatttaaaa | ggtttgtctg | tttaaacatt | tttttgaaat | gtgaattcct | 1260 |
| ccctcacatt | atgatcaaat | ttaacattag | attagatgca | aacaggaagt | tatctaatat | 1320 |
| ctctgggttt | atttataaat | ataatacata | ttaaagctag | aaattttgat | cctaattttg | 1380 |
| gtaagctttg | tttgtgttga | ccttttttctt | tttttttatca | tctacattgg | aatatccaaa | 1440 |
| agtagtatct | aattagcctt | ggagaggtgt | ttgtgcttta | acgatgttca | aaactactgc | 1500 |
| tgaaatacac | tatttggaaa | gcctaaggtc | tacagttatt | tagagtcaga | ctgcctgagt | 1560 |
| tctttgaatc | ctgtctctga | cattttcttg | ctagtgacct | ggagtaggtt | attattgcta | 1620 |
| tttttttgag | acagcgacgc | gctctgttgc | ccaggctgga | atgcagtgac | gtgatcttgg | 1680 |
| ctcactgcaa | cctcgaccac | ccgggatcaa | gcagtcctcc | cacctcagcc | tcctgagtag | 1740 |
| ctgggaccac | aggcccacac | cactgggccc | ggctagtttt | ttttataatt | tgtagagacg | 1800 |
| aggtcttgct | atgttgctca | ggctggtctc | aatctcctgg | cctcaagtga | tccgcctgcc | 1860 |
| tcagcctccc | aaagtgctgg | gattacaggc | gtaatcccac | ccaggatcaa | gcagtcctcc | 1920 |
| cacctcagcc | tcctgagtag | ctgggaccat | aggcccgcac | cactgggcct | ggctaatttt | 1980 |
| ttaataattt | gtagaggcga | ggtcttgcta | tgttgctcag | gctggtctca | atctcctggg | 2040 |

```
ctcaagtgat ccgcccgtct cagcctccca aagtgctggg attacaggca tgagccacca    2100
tgcaagctgg gtaagttatt aacctcttga tgcttcactt tcttcttatg taaaatgggg    2160
ataataaaat tttccttgaa gaatgattat gattaagtat gtgagtatag gggttatata    2220
aatttctgct gttttattta gtatatactc agatttttat atattcaata tacaaattag    2280
gtttaaaaat aatatatttg ctcatgcctg taatcccagc actttgggag gctgaggcag    2340
gcggatcacc tgaggtcggg agttcaagac cagtctgacc aacatggaga acccccgtct    2400
ctactaaaaa tacaaaatta gccaggcttg gtagtgcatg tctgtaatcc cagctacttg    2460
ggaggctgag gcaggagaat cacttgaacc tgggaggcag aggttgtggt gagccaagat    2520
cgcaccattg cactccagcc tgggcaacaa gaatgaaact ctgtctcaaa aaataaatt     2580 ttatatttat atatttgggt agtggtcatt aaatggtaac acaagtttga aatttgtttt    2640
gtttgcatgg agaatttgtt ttgcattgaa acagcagtc cattcatgag atcaccagaa     2700
agaatagact tgcttataat aagttatact tctaataagt aacagtgaca ataaaactgt    2760
ttgcaaacat gccatttct gtgtgtataa caatatagtt gtcttttggg tatcagacag     2820
acctggtttg agttttccag ttgtgcttgt tttgtggcct tcagtaaatt gctaaacttt    2880
gcttggcctc agtttcctca tctgtaaaat aatgataata atacagttca aagaggattg    2940
ctgtgagaat taaatatgaa aatgtatgtc acactcctgg catggtgcct acctcacagt    3000
gtaggtgctt aataatcctg agtgtccttc tgtccctttc tccagaccgt agatggaaga    3060
tgcacgttga tagcaagagg aaggtgattg ccattgggga aggtgtggaa agggcgtcct    3120
gtacatgatg atgaagggag tgggcttagc ttagcaagtg gtaagcttag cagggaaccc    3180
aattccgacc ttgaagtgtc tgagcagatg tcatgtgtaa ggggaagcag ggatgctgtg    3240
tctgatctgc ccctgcagga agcactagga ccggcaggta tcagtagtga aaggccactt    3300
tgggtttcac gtgaggaaga cttcctata gagctgtgga aagatgagat ggtgcctctt     3360
tgcaatagtg agcgtctcag ggccggatgt ggtgtctgac gactggttgg ctgcagatca    3420
agagctctgt agagaggatt cctccaagca ccaggaaggc agactacatg gcctctgcgg    3480 ccccttttcaa tgcttgtatg tcagtggccc cctttctaaa ttcatgcctg attatctgct   3540
ttcctaggcc aagttggttg tatgccccca gaaacctagg atttagcctt ctgaagtcag    3600
ggagttggga ctgcttattg tttaatttta aaatgttttt taggattgac aattttgtg     3660 tttgtatttt gtcatttgca gcagaggctg caaactggtg agttttgggc tggttctggg    3720
ctgtggataa cctttgtttg gcctagaaaa tgtgatcagg ggatcactgt gttaactaaa    3780
tttaaattga ttgcctgcgt ttaaaaacta agaattttac aaaaaagcca aattttagt     3840 gtttcttcaa aatgtgggat tatctggcaa cattgggttc taccttctca gctggcagtg    3900
gatagctgaa gctgtgtaga tggtggcctt ttggttgggt catgcgtcag ctggtttgcc    3960 acagtccccca ccactccaca cagtcttccc atcatcaaat gtcagttgtc attttttcatt  4020 tacttaagtt gttttctttt agtagaatta ggagaaaact gaaacagtta ttttttcaat    4080
gtccatagta gtaatggaaa aactaaagat attttcatag tttcaaactt caagaaaaaa    4140
atagaagagg gtatattttg gatgtatgcc gaagtatact tgtagaagtc taacttgcaa    4200
acaagtggtt tctgtgtctt tagactgcat gactcagtca ggcctgcttc actcagactt    4260
tttttttttt tttttttttt tgagacaggg tctcactgtt acccaggctg gggtgcagtg    4320
gcgctatctc agctcactgc agcttcaaac tcctggaccc aagcaatctg cccacctcag    4380
cctcctgagc agctgggatt ataggcatgt cccaccatac ctggctatat ctatggtttt    4440
```

-continued

```
tttttttttg ttttttttgtt tttttgtttt tttttgtaga gatgaggttt cactatgttg    4500
cccaggctgg tcttgaattc ctgagctcaa gtgatccgcc cgcgtcagcc tcccaaagtg    4560
ctgggattac aggcatgagc caccgtgcct ggcttcgctc atatatttaa atagctctga    4620
aggtatctga gtgtgacccc taatctggac agttaaattt tccctctgtc ttcagatgtg    4680
actcatttcc tccctctttt tcagttctcc atggtcatgg agaaggagtt gcctggcagc    4740
atatctttt tgccttccct aacatccact gtggcctcct ggcttggtga atggggaca     4800
gtgtgtaatt tgcacacgtc tgtgatctat ggaactaagt tccattctgc tttttccagt    4860
ggatccccaa tcctccctag acttcatggc cccaaacaga tggagcctgt aacctcgttg    4920
actctgagtg atataaccga gggagtgggc tcaatgccta ttaaggcaca gattgaagtt    4980
ttaggactct gttctttgtg cattttgatg tttagtacga acagaatctg ctttgtttt    5040
gctttacaag agtgattctg gcttcattgt gaagaacttg gctggagaga gagcagggaa    5100
gatccgtggt aattaacttc agttttttgt agggtggttg ggtggaagag aggagtagga    5160
tgtgtgttga taatgatgga aagactgatt agtggaattt ttagaatgac tgatttaaag    5220
ttgctggaag gagttctcat ctatcaactg gttatttact gatggaatgt gcccctaac    5280
agatctgtga actttccgtc actcaatgta tttaggtaaa tgagagtggc cccatctgtc    5340
aggatgctgt aggagattcc taaattagag ggaaggttgg gctagataga tgacctctct    5400
ggtctctttg gaactcaaat tcaattattc tctgaattaa acttattagg aatcttccag    5460
cttgaacaat tttacttcag tccataaaga gaaatatta tgagttgact gagaggctga    5520
atataacatt ataactttaa ctacaattag atctgggcag attacttgca ctttctccaa    5580
tgttccaata taaccttcaa aaatgttgta aacagatgta cccagtagct agtatttata    5640
agccgggatt ttacaagcat atttcctgaa ggatttttt tctaccaaaa actttgtttt    5700
accttagcca aaactcattg tgtaggtttc ttttttggta gcgtaataat acagatgtta    5760
tcatttacat aaaagtatta tccgttactc tttgtaaagc atttttattta atttcaaaac    5820
ttaggatttt gtacattatc attcattgct gtttgttaag gtgtatttaa tttggatata    5880
atgacctaca gaaaaaggtc actttaaaga aaaactttt aaaaatgatt tttaaatgat    5940
gcataatcga tgtacatagt tctggggtat gaatggtaat tcagcacgtt catataattt    6000
gtaaagatca aatcagtgta attgggatgc ccattacctt aaatatttgt gttttcttca    6060
tgttagaaac attagaacta ttctttata gcttgtttgg aacttataat acattattgt    6120
aaactagagt cactctactg atctaacact aggtttatt tcttctatca aacagtatat    6180
ttgaacccat taatcaacct gtcttcatcc attccttcct acccttccca gcctctggca    6240
accaccaatc tactctctac tttcattaga cttactttt ttcttttttt tatctcccac    6300
atgtaagtga gaacatgtga tatttgtctt tctgtgcttg gcttatttca cttgatgacc    6360
tccagttca cccacattgc tgcaaatgac aggatttcat tcttttatg gctgaataat    6420
aatccattat gtatatatac cacatttct tgacccattc atctcttgat gggtacttag    6480
gttgatatat tttggctttt gtgaatagtg cagtaataaa catgggagtg caaataccc    6540
tttgatatat tggttttctt tcttttggat ctatacccac tagtgggatt gctggatcac    6600
atggtagttc tatttttagt tttttgagga aactccaaac cgttctccat agtgattgta    6660
ctaattcgca ttccttcaaa gagtgtacaa gggtttccct ttctctacat cctctctagc    6720
atctgtcatt gcctgtcatt tttataaaag ccatttttcac tggggtgaga tgatatctca    6780
ttgtagtttt gatttgcatt tctctgatga ttagtgatgc tgagcatttt ttcatgtacc    6840
```

```
tgttggccat ttgtatgtct tcctttgaga aatatcagtt cagatctttt gcccattttt    6900
aattgaatta tttgttttt  gctgttgagt agtttgagct ctttatatat catggttact    6960
aatcccttgt agataggtag tttgcagata ttttctccca ttttgtgggt tgtctcttta    7020
gtttgttgat tgttcccttt tctgtgcaga gcttttatt  tttattttt  tgaaacaggg    7080 tcttcttctg tcaccctgac tggagtgcat tggtgcaatc acagctcact gcagcctcaa    7140
actcctgggc tcaagccatc ctcccatttc agtctcctga gtagctggga atacaggcac    7200
tcaccatcat agctagccac ttttaaatt  ttttgtagag agaggtcccg ttctgttgcc    7260
caggctggcc tcacacacct ggcctcaagc gatcctcctg ccttggcccc caaagtgct     7320 gggattacag gtgtgagcca ccatgcctag cctgcaggag ctttttagct tgatgtaatt    7380
ccatgtatcg atttctgctt ttatgcctgt gcttttgagg tcttagacag aaaatcattg    7440
cccagaccaa tgtcctgaag catttcccaa atgttttctt ctggccgttt catattttca    7500
ggtcttagat ttaagtcttt aatccatttt gacttgattt attgtgtata gtgagagatg    7560
gagtctaatt ttattcttct gcctatagtt aacagttttc ccagcaccat ttattgaaga    7620
gactgtcctt tccccattgt atattcttgg tgcctttgtc aaagatgagt tggttataaa    7680
tgtgtgaatt tttatctgga ttctctgttc tgttctactg gtgtatgtgt ttttttgttt    7740
ttctttcttt cttaagccag taccatgctc atttggttgt tagagctttg cagtcaattt    7800
tgaagtcagg tatagtttga tgcctccaac tttgttctta ttgatctata cctttggcta    7860
ttcagggtct tttgtggttt tacataaagt ttagaacacc tttttttcc  tatttttgtg    7920 aggaatgtca ttggtatttt gatagggatt gcattgaatc tgtaaattgc tttgcgtagt    7980
attgccattt taacaatatt aattcttcca agccgtgagc atggaatatc tttccatttt    8040
ctaatgtgtc ctctttggtt tattttatca gtgtgttaca gtttttatcg catggatctt    8100
ttacttcttt ggttaaattg cttcctagat attttacatt cattgtagct attgtaaatg    8160
ggattgccta cttgatttca ttttcatatt gttcgctgtt ggcatatata gatgctactg    8220
attttgtatg tttattttgt atcctgcaat tttgctggat tcattatca  gttccaacag    8280 tttttggtgg agtctagatt tttctaaata taaaaccatg tcatgtgtga acaaaggcta    8340
ctttgaacaa aagggtaatt tgacttcttc cttccaatt  tggatgcttt ttatttcttt    8400
ctctcgccta attgccctgg ccaggatttc cagtactatg ttgaataaaa gtggtaaaaa    8460
tggaaaagaa caacttttat gaagaattag tttttaaatcc acatttttat gtcacaatat    8520
ttgcactctt gtgaaagtaa ttaattggtc atttgatgat attattgggg cttgcttgtt    8580
atgtaagtaa cacttggagt ttataaatgt accataaggc cgggtgcagt ggctcacgcc    8640
tgtaatccca gcactttggg aggctgaggc gggctgatca cctcaggtca ggagtttgag    8700
accagcctga ccaacacgga gaaactccat ctttactaaa aatacaaaat tagtcgggcg    8760
tggtggcaca tgcctgtaat cctagctact gggaggctg  aggcaggagg attgcttgaa    8820
cccgggagtc agaggttgcg gtgagccaag attgcgccac tgcactccag cctgggcaac    8880
aagagcaaaa ctccatgtct ctctttctct catctatatg tgtatatata tatgtgtgtg    8940
tgtgtgtgtg tgtgtgtgtg tgtgtgtgtg tgtaataaaa tatctcattt ccaagataat    9000
tgactgcatt aaaatttatt tgtgcattta atgcctttga aacacttaga aaagtttat     9060 attagggaat ttagatttgc aatggcttta aagcaataca taccatgcta gtattgcgtt    9120 ttgaatttc  tcaaaattga ctattgattt tgaagacatc ttcagtttgc ttttaaaaat    9180
gttaaaaatt tatcttgttc ttcatttgt  tttcatttaa tccgtagcca ttgagtaatt    9240
```

-continued

```
aatgatggtg tggtataagg ctcacaaacg tgatgcataa taattgtggg agaggaaaat    9300
taccagaact ttgaggccca gtaacattgc ttcataacag tgttgtgagg tgatagcatt    9360
gaagttatta acgctatggc taccagtgtt ttctgttcat ttgtttgtta tatttaggat    9420
ttgtctgggt ttatctgaat cagttaatat gcagtatagt catgtatcac ttgacaatgg    9480
ggaaagttct gagaaaagtg taagatgatt tcctcattgt gtgaacatca tagagtgtac    9540
ttacatgaac ctagatggta cagcctacta cacacccagg ctatatgcca tagcctatgc    9600
tcctaggctg caaacctgta tggcatgtga ctgtagtgaa tactgtaggc agttgtaaca    9660
caatgggaag tatttgtgta tctaaacatc tctaaataga gaaaaggtac agtaaaaata    9720
tggtatcata atcacgtgga accaccgtat atgcagtctg tcgtcggcta ttacactgtg    9780
atgctgcaca tgactgtatt aagttttttta actgagactg tgggttctc ttcatcagca    9840 tctgtgagat atgctgtctt ttgactgcgt atgatcatta tgagacaggc agagcagaag    9900
tttgggtcgt ctgactttgt ggctgtgaga ccttgactca cagtagcagg tgctggcgct    9960
tctcccacag tgtggagcat agagcaggag gcaggagcag gtggccagct gccagcacgg   10020
cggcactgca gtgttgcctt gttgaagatg ccggcttgga atatgaaatg ctaacgagaa   10080
atggtggggg atctttaagc agaaactctg tgaaaatttt gcttgatggg cagtgatcgc   10140
atgtggagtg gcttatttaa aataaaaggg attgcttggc ttctgacaac agagatgtag   10200
agtgcaacaa acactgttct tcctttcaca tttaccacca ctgccaccat cactgtcacc   10260
tcccattcat taattcgttc attcatgcat gcagttactt aacatgtatt tattgggtat   10320
tcaccatgtg ccaggcgctt cttaaagtcc tggactttca acagtaaaca atttaaacaa   10380
aatccctgcc ttcctgcctt gtggaattaa cattctaaga ggcagacctt atgttaaaca   10440
atttacatct attgttttac atgatcctta caatagcttg ggaggcagac aaaattatcc   10500
ccattttaca gattaagaaa ctgagggtta gagaaattaa atgatgtgtc cagtgtcaca   10560
tacgaaactg aggcgcagag aaattaaatg atgtgtccag tgtcatacag tgggatctga   10620
tgtcacgcca gagggactct aaattgtggg ccccgagttg ttttgctagc ctcttaggag   10680
caatgtctga gcggccaatg aattgcacgt cagttgtaca tttgcgtggg ttttcagcat   10740
cacacgtggg aggtaaacct tcacaccacc cctgttttag atatgaaggc cagtcctacc   10800
cgccctcact gtattctctg ggcaaatttg gaaacctttg gttttagaaa cagacttcct   10860
aaatttgggc cttttgatca aatggggaga aaaatcagct ccccggtaa tgtttctgag   10920 gatctcagga ttctcaggca gatacttggt gtgcctcatt ttcttctagt cttgccttca   10980
tctgggacat ttttgctacc gcatttctca aggtctgtgt tccttcagcc tacgttattc   11040
aaagtattgc ttttttcatca gaaacagtgt ggggaagccc tcttcagcac atgaatattg   11100
ccgaggtttt ttgcccatta atgtaattac atccaaggtg cacatttacg tttgtgaggg   11160
attatttaat cttttgtaat cctggttggg taaaagtaat ttatatttt aatctctact   11220 tatgattgtt attctttat ttttactttt cttccttgac tatagctaag cagtaaggag   11280
tggtgcttgg tcagatgttc tgtcagaagc attctgtgtt tgacctgaga agtaaagaat   11340
atggaaggag ttttttattgt tttcttcttt gaattctaag cagagaggtt atttctgata   11400
gttcacatta ctttagaaca tttatttatt tattttattta gagacagagt cttgctctgt   11460
tgcccaggct ggagtacagt ggtgcaatct cggctcactg cagcctctgc ctctcgggtt   11520
ctcctgcctc agcctcccga gtagctgaga ctacaggtgg acactgccac gcctggctat   11580
tttttgtatt tttttagtag agatgcggtt tcaccatgtt ggctaggatg gtcttgatct   11640
```

```
cctgacctca tgatctgcct gccttggcct cccaaagtgc tgggattaca ggcatgagca    11700
accgtgccgg cctttttttt ttgagacaca gtctcacttt gtcgcccagg ctggagtaag    11760
tgcagtggca ctatcttagc tcattgcaac ctctgccatc tgggttcaag tgattcttcc    11820
acctcagcct cccaaatagc tagggctaca ggtgcgtgcc accatgcctg gctaattttg    11880
ggcagaaat  ggggtatcac tgtgttggcc aggctggtct tggactcctg acctcaagtg    11940
gtctgcctgt cttggcctcc caaagtgctg gattacaggt gtgaatcac  tgcatctggc    12000
ctagaactta tattttaat  gtcagttttt cttataatta tttatagatt agaacatgtt    12060
atttacattt cttatttgtg ataggcatta tgattgtcaa ccccactta  tgatgaagga    12120
tatgggattc aggaagcctc taagttttga agagatgaat tgctagccca gatctactgg    12180
ttttgaagcc tgagatgttt ccactattcc cttattttta ttaataataa tttgtcatgt    12240
gatagtggct ctcaaacttt tcattctggg ggtgttccaa tgccccatct tatcatttta    12300
tattctccag ctcttctctg gataggaaca gaaaccctca agaatatatc tttgcatgca    12360
tgtgtgcaca tgcagtctag gatattcagg ttttttatta cagtcaggtt tgcaacaatt    12420
tttgcatagt ttttgactag gtattagtaa aacatggtgt ttttatgga  ttaattat     12480
gtgtgtgtgt gtgtgtgtgt gtgtgtgtgt gtgtgtgtgt gtatacatat atttcctcc    12540
caacatttta ttaagaaaat ttgcaagaat atagaaaaat caaagaatt  gtatagtgaa    12600
cacccataaa cccaccactt gattctataa ttgttaatag cttgccattt tgcttttac    12660
atgggtcatt ttacattgta tccttcaaaa tagaatactt cgtaagtggt aatttacatt    12720
tttctcagag atctttgcca aggaatttaa ttttagatgc ctgttaacac atatgtcctg    12780
ttatattatt atctcagaat aaagcattag aaagatcaag tctagttta  tgatttggaa    12840
ctctctggtt tttgtaattt taggatggag aactaaattg acagtatacg actgtagttg    12900
ggcagtctaa agaacttgag aaaccttaca tagtttgaaa ccccaagtga ctttataaat    12960
tcatagaact aaagtcattt gggtgacctc agtaataaaa aatgaaatca gacaatgcaa    13020
aaccatcgga aatatctgag gaatgttgga gataattcat gtgtacagga ggttctggca    13080
gagaagggat ctacatataa aatgtatcaa aaggtcagaa ttgttttaag aaaacctaga    13140
agcaggaatt agtggccggg cgcggtagct cacgcctgta atcctagcac tttgggaggc    13200
tgaggcgggt ggatcacctg agatcaggag ttcaagacca gcctggccaa catggtgaaa    13260
ccctgtctct tctaaaaata caaaaattag ccgggtgtgg tggtgcatgc ctgtgatccc    13320
agctactcgg gaggctgagg caggagaatc acttgaaccc aggaggcgga ggttgcggtg    13380
agccgagata gcactattgc actccagcct gggcaacaga gtgagactct gtctcaaaaa    13440
aaaaaaaaa  aaaaaagga  attagagtag gggcatgcaa atatttccat gcaattaatt    13500
gttcttctga tcttttttt  gctctctgat acatatctct ttaaatttcc ttctcctgca    13560
caattttct  tcccttgta  tcacagagtc ccttttctgt cttaatgtgg aaggctttca    13620
tttacactgg ctgttatttt atttatttt  acctatttta gtaacagaaa tgaggctgct    13680
gggtctgaag gaagcagagc tcatgattta atagcattca ttcttcttct gtatttacct    13740
cacacacaca cacccccccc cccacacccc cacacaccccc cacacaccaa attaacattt    13800
tgggaattcc cgtgttttgt gttatgtgac ttggcctccg tggcaacctc tgacttcagt    13860
cccggggctt gtggttactt gggtggtaca tccttgtgct gccgcctgtt gctggccagc    13920
tctgtgacct tttgcaagtc acttaaggtc tctgttctt  tatctgtaat tccagagggt    13980
tggactaggg aattttgcag gtttatccca ccagcactaa aaattccctg ttctgtgttc    14040
```

```
acattaacat ttttctctc ctccctgcgc ttctccctg accccgccct gacttaaatg    14100
ttttgtgctc aggctaattt ttataactat tacactgatg gtcttcaata atggctctta    14160
ttattggcca attaagatta gaaagcatgg ccggcacggt gggtcacacc tgtcatccca    14220
gcactttggg aggccaaggt gggcagatca tgaggtcagg agatcgagac catcctggct    14280
aacacagtga aaccccgtct ctactaaaaa tacaaaaaat tagctgggcg tggtggcggg    14340
cgcttgtagt cccagctact agggaggctg aggcagggga atcgcttgaa cccgggaggc    14400
ggaggttgcc gtgagccgag atcgtgcctc tgcactccag cctgggcaac agagagagac    14460
tctgtctcaa aaaaaaaaa aaattataaa gcataccttc aagtgtataa taacttcatg    14520 tggaaaaga ttgtgtgtgt gcctatatgg gtagatggat gtatgtgtat gtaaaataca    14580
gttttcatcc agataaggaa ttaaaggctt atctgtctat ggtagaggct ggtctgtaat    14640
attaggtaaa aatctttctg ttggatatgt agatccttt tcttttgaga tagggtctca    14700
gtctgtcacc caggctggag tgcagtggtg cagtcatggc tcactgcagc cttgacctcc    14760
ccaggctcaa tagatcctcc cacctcagct cccaagtaac tgggactact ggcatgcact    14820
accacacctg gctaattttt tgtattttta gtagagatgg ggtttcaccg tgttagccag    14880
gatggtctca atctcctgtc ttgctctgtc tcccaggctg tagtgcagtg gcacagtctt    14940
ggctcactgc agcctctgcc tcccgagttc tcccacttca gcctcatgag taggtgagac    15000
tataggtgca tgccaccacg cccagctaat tttgtattt ttagtagaga cgaggtttca    15060
ctgtgttggc caggctgatc tcaaactcct ggcttcaagt gatctgcccg cattggcctc    15120
ccagaggctg gaattatggc atgagccatc gcccctggcc ctggctaatt tttttatttt    15180 tacttttgt agagataggg tctccctatg ttgtccaggg tggtcttgaa ctcctgggct    15240
caagtgatct gcccacatca gcctcccttg tagcttggac cacaggtgtg cactcccagg    15300
cttggctaat tttttttttt ttctgttagc taattgttta attttttct ggtagagaca    15360 gtctccctat gttgcccagg ctggtctcct aggctcaagt gatcctccca cctcagcctc    15420
ccaaagtgtt ggaatcacag gcatgagcca ccgtgcccag cctttgttat ttttaaaatg    15480
atgaaggtat taccttaaaa atctcttgcc acatgtttgt ccgggataat ttgtgtattc    15540
acatacttag aatatgtaca ttttgaaaac ctttgattaa gtggttttct tctataaaat    15600
atgaaggttt gtgatcctgt tctcctattc atcatcccgc ctccacaata acataaaaga    15660
tctgaaaatg ctgctttatc ttttgggtat tttatttat tttattttat tttattttat    15720 tttatttat tttttgaga gagtctct atgtatccca ggctggagtg cagtggcgtg    15780
atctcggctc actgcaacct ctgcccctg ggttcaggca attctcctgt ctcagcctcc    15840
tgagtagctg ggattacagg cgtgtatcac cacacctggc taattttgt agttttagta    15900 gagacagggt ttcaccatat tggtcaggct ggttccgaac tcctgacctc aggtgatcta    15960
ccctcctcgg cctcccaacg tgctgggatt ataggcgtaa gtcaccatgc ccagcctttt    16020
tggggtattt ttaaaatgta aggtctttca tcaaaggata tagcaagacc ccaaaacact    16080
ctgaacctct gctgtatata acttttattt aagataattt aatggttcat ttttaataaa    16140
aaagcaccac gttggggtaa caaggacttc caatgtacaa gactgtagtt cagccaactt    16200
aaaaatgaaa gaactctagc aaggaacaca agtaagttta tacccgatat tttgcaaatc    16260
atgatattat ttttaagggc ctctcttgag gcagggtttt tatgatcata acattccagc    16320
tgtggttttg gaggcagaat gtttactact gctctaaatg caaggatggt aggtgtgtat    16380
tcttactgct aaagggctta aaaaagaagc tgaggctccc ttcaagtgag taaacccttta    16440
```

```
ttcggctgac ttgggagccg tgttcctatg gaacttcggt ggtaattatg gaatgcaggc    16500
ccaacaacag cccagtcatg ggcgagcctg gcctctccga ggcatgatgg caggctgtcc    16560
cggctaatgg cttcaggcag cccatggaaa accactttct ggttaagtct gcatcatact    16620
gttccaccaa tggaaaaaat tgaacatgat gagggtgtgt agctagcaga caaaaatata    16680
tccagcattg cacaggatct gttttttagct ctcaacggct gagcatttga agtgttagac    16740 actgttttcct ggcttaccat gagcagaagg aagagtgagt ttgtggatgt gtatatagac    16800
tctagctttg tgaaactttt cttattaacg aacagacccc gagaaatact ggctacatcc    16860
aaagttctgg caaaggtaag gttataaatg tttacttccc ctcttctgga gttgagacgt    16920
aattttacat gtgagataaa aatgtttctc aaaatgctcc caccggcaat atataagtgc    16980
tgacttattt ttgtctgaca ttatttttgta cttaggcagc acacgttgct gtgcataagg    17040
gaattgttgc ctttaaattg gagtgtctgt gtgctttcaa acacctattg gtgatttatt    17100
gcagttgcct gcgccgtttt actaattaac tctccaaaat ttgtacgtat tgtatggatt    17160 tattttttcct gatggtctca agaaagtacc acttctcagt gtgatcatgt taaagcattg    17220
atgactatta ctttaccagt taattttttc agagtagaaa gggaaattaa gatgtggcag    17280
agattgtatt ttgcagtttt tgggttatta tatcatctca tcagggctta attttttagct    17340 gagtgggcta tttggcttaa gagtttcttt tcaaacttgt aatttgactt tcgctgttta    17400
gtatcgtttg tcttttttgtc ttaaacttta tgaaaaagaa atggaatccc ttgtaatctt    17460
gggagggggg tacttgttta agaggagtga ttgattcata ttctagtcca ttagaggctg    17520
ctcattcatt agggtatttg aaacaccaga agcacaagta ctgctgaacg tctggtgtgt    17580
gctcatcagc aggggccgag gagccctggc tttggtgtag ttcttccttg gctttacatt    17640
aatttggcca agcatgtaat tcgcagaaaa ttggtaggtg gagagacaga aatagggagc    17700
tttattgaag tcattgtaac ttacaggatt atttatagaa tttctggaaa gtaagggtac    17760
gggtgaacag ctgctggagt ttttcctaac aggtttaaac attttgttgt ggccttttgt    17820
cacacttagg gattctaaaa tttttatactt tcagcattat gaggttatga attattttca    17880
ggcaggctac gtgggttcgt tttcagctgt gctgggtcag ggctgtcatc tccatcggtg    17940
tattgggcat cccccatgtg ttcacttcct ttacagacac gtctttaggg atggaggaat    18000
gtgagtgtgg ttcaggcagg ttacagttca tagaaagatt ggtcatattt tattgatgac    18060
ttttcctttt catctaaaaa atgcggctct gacagagcca gcaagcactg agagcaggaa    18120
cagtgcactg accgccgcct tctccggtca cattaacact tgtcacctac tttgattttt    18180
gccagagctt gtggacagaa agtgaagtcc attgaagaac ttaatgactc aaattcatac    18240
tgaccagacc gtaaatagtg ttttgaatgc aaatagataa caccttttttt caatacttta    18300 gtgcagaggg agtgactttc caaagccctc tcattagatc aggcctgcag gaaggatgcc    18360
tggaagtgcg agataagcgt taggctcctt gtgaagagat tagttttcca gtgggtaagt    18420
gggtccttca cttacccatt aagtaaaaca gatgattctg tcttggtggt ctgagattgt    18480
gtttgagcag agccatgctt tcttttgcaa aattagttaa gggtctttgc agcttcttcc    18540
caccagaagt attgaataaa aaaccacaaa gcgtaaatat ctgatggggc actttactat    18600
atgtgtatgt gcctctaggt ttgactcact ttgtaagatt cccttatgtg attataataa    18660
atcaggttag tgagatccct tagttcaact ttttctttttt tgttttttgt tttgaaacag    18720
agtctcactc tgtcgcccag gctggagtgc aatggcgcga tctcagctca ctgcaagctc    18780
cgcctcctgg gttcacacca ttctcctgcc tcagcctccc gagtagctgg gactacaggc    18840
```

```
gcccaccacc acacccggct aattttttg tattttggt agagatgggg tttcaccgtg      18900
ttagccagga tggtcttgat ctcctgacgt catgatccgc ccgcctcggc ctcccaaagt     18960
gctgggatta caggtgtgag ccactgcacc cggccttcag cttttagatt tagaaaaata    19020
caggccgtga agaacaaggt ctatttggac atttttaaa ggataattt gcatctttt      19080
tgttttgaaa ttaagtgtgc cttctacatg aaggtaataa cagctttact agaagggcta    19140
gaaaaagat aaaggtatgg aatagaaaga aatagcagca gtattaaaaa cagtaaaaag     19200
taataataat ggtagtagat aaacctgaat gtctgactgt tgaattctat taacagggtg    19260
gaatgtcttt ttattactca gttctactta aaacaggctt acaaatatca ggaggcttca    19320
acatcagtgt ctcaggaaac atattgaaca ctcatttttc aggtctttat agtccatagt    19380
attgtagaga tagaacgtta gagctgaaaa tggaccttag gcagttttc aaaggagaca    19440
attgaagaac cacagaactg aagcgacttg tccgaagcca cagagatggt tagttaccca    19500
gctggaagga aattccaggt atcctgttag tcttttctt actctacctg ttccttaatt     19560
gaggaaactt tggcacatcc tgatgtatct tagataattg atagagactt gtgtatgcat    19620
acacatgtgt gcaaatatat acagacaaat gcacagactt tttttttttt ttttttta     19680
agacagagtc tcactctttt acccaggctg gagtgcagtg gtgtaatctc ggctcactgc    19740
aacctccacc tctgggttca agggactctc ctgcctcagc ctcccagta gctgggatta     19800
caggcaactg ccactacgcc cggctaattt ttttttgtat tttagtaga gacggggttt     19860
caccatgttg gccaggctgg tcttgaactc ctgatctcaa gtgatccgcc cgccttgaac    19920
tcccaaagtg ttaggattac aggcatgagc caccacgtcc agccgacatg cacatacatt    19980
tcctttcctc cctttgtcca tccttccttc ttcctttcct cttttctttc tttttttttt    20040
tgttgttctt tctttcatct atttacttac ctgtttacca aacgtgtttg gtaacctgtg    20100
tgttggtttg gtttacctgt ctgtttaaag ctctagtaga gaaagggct tttgcttttc    20160
ccatagccta gtcaaattca aagctgtaca ttcaatctgt gaccatcagc tctctgactg    20220
ttgccagaga gaattttagg tgcacacatg ttaccctaac ctatgtgata agacaggttt    20280
gattagactt catctgtcag tctcttcctg gttcagtctt agattggttt tctttggttt    20340
atagtcacat tccaatagaa gactgtttag gttttgttac ttctgtgcct tacaaaaag    20400
aagccctgga agggaacaga aacacagcag atgaggcctg gctttagtgc caaggtgatg    20460
taaggcactt ttggaaaagt aaagtttaca caaaagtga taggccaagt tatcatttac    20520
acttaaggaa agggatgcag tgggctccac agataatgtc aggatgaagt tgattcaggg    20580
tgttcctagg acttgaataa aggttcaaaa atcctgggta ttgttcaagc actggaaagt    20640
gagaataatc cttatcctgc ctttgtgctt gaccctgacc catctctata gtcgcagaat    20700
tgctagagtc ggatttctaa aatggagatg tggggaaggg ctaaggagag acagagtttg    20760
caagctttta aagacaaaag ctagaatcca tatgattaaa ggcaatgaga agaaaccaag    20820
tggagagaat aaagacaggc tcttttcga gttacccttg gccaccctg gaaggtggaa     20880
aaaggcatct taaagataaa tgaaaggaag ctttatacac agacacagta gtgaaccgag    20940
gaaactcatg acattaggag gcactggaga gtaaagcgct tcatggaaag tgtccatata    21000
ttcttggaat acacacacac acacacacac acacacacac acacacacac tctccgttga    21060
aaattgatag gatgatcaca aatgtatcca aacagccaga caagttaact ataaaacaac    21120
aacaataaca agcccctga aataacagga aactaacaat aaccatcact tacctttta     21180
agaaatgtca cagtgggaaa aaaatagaaa ttacaagaca acacagtgac atgcaggtaa    21240
```

```
tgaaggagtt tctcactgga gctcttgtat cctgacaccc tactgcatgt atgtgatgtt    21300
ggtgcctctc aaacgtttct gaagtttctg tgataggagg ggcagttgct ctagagccac    21360
ctcctcttgt gcgtgcaatt cctctccctt tgacccattc taggacattt taggaatggc    21420
ccctctctct gcaccacatc acattttccc tttaattctc attgcgtgct ggaattttc    21480 ctgaagatac acacatagac aataaatgaa gctcttttg atccctctgt ccttcccgct    21540
agcaactgat tcctctctgc tccccttat agtaaaactc tttgaatgag ctgtccctat    21600
tcactccctt cagtttcact gaccttatcc tcaaactcaa tccagtcggt ctttctccac    21660
cccattctgc ccttgtcctg ttcacaggga cctgcataat gccagatcta ctaaatgcac    21720
tgcttgttct aggttttgt tatttgaatc agaaacattt gacatggttg ctcagtcttc    21780
tccctgaagt gcttttccca attggcttta ggtgccacat actctcttgg tttcctcttt    21840
tttttttttt tttttgagat ggagtcttgc tctgttgccc aggctggact gcagtgatgc    21900
gatctcggct cactgcaacc tccgcctccc aggttcaagt gattctcctg cctcagcctc    21960
ccaagcagct gggattacag gcatgcgcca ccaagcccgg ctaattttg taattttttt    22020 tagtagagac ggggtttcgt tggccaggct ggtctcgaac tcctgacctc aggtgatctg    22080
cccgcctcag cctcccaaag tgctgggatt acaggtgtga gccaccaccg tgccaggtct    22140
cttggttcct cttaattcag ttcaccaact gcccccttctg tctccattat gggcttctcc    22200
tcatttcctt gaccccttaa tgtcaaggtg ccccagggcc tccttggacc ccatgtcttt    22260
cctttgttta cttatggaga acccatccag tttgtgtttt aaataccatc tttgtgtggg    22320
tgagcagccc acttctctcc tgaactccag actggtatta ccacttaagt atccagtgga    22380
cacctcaaac ccagcttgtc caaaactgaa ctcctcatct gcccgcgga agcctgctct    22440 gctctgccgt ctgcattctc ccatggcttt aatggaacag tgtggaatca tccttggtgt    22500
cactcacact tgcttccacc tgccctcgag tcctgctggc tctcccttcg gccctccaga    22560
gcttcagctg tgtccggagg cagcctcctc ccctaccacc cccctccctt accacccca    22620 cccaagctgg ggcgcattgc ctctcccctg catcgttccg gtagcctagc aggtccccct    22680
gctgcttcca ctgtgtcgct gacaatccat atccacacag cagctacaca gatccttta    22740 aaatgtccca tgatgagcct tctctatcac accctctaat tatgactttt tttctcaagg    22800
tgaaagccaa agtccttaaa ctgtccctca aggctgcctt cactggctct gtggcccctc    22860
tctgacctct cttgcccttc ttcccctcgc ttgctctgct gcggccatgc tggtccctgc    22920
ctctccggca cttgcacttt ctgttgcccc tgcccacggt gcccttccc tgaaatacac    22980 ttggtgtctc ctccttgcaa gtctctgctg aagtgtcacc attcagagag gcttcctcgc    23040
cttttaaaaa ttgcagcatc cttcccctct ccacgttgcc tcctccccca tttccttctt    23100
tactattttg tcaaagtgct tatcacctcc taaaagaaaa tttattttc ggccaggcgt    23160 ggtggctcat gcctataatc ttagcacttt gggaggctga ggccggcaga tcacttgagg    23220
tcaggagttc gagaccagcc tggccaacac tgtgaaaccc catctctact aaaaaaata    23280 caaaaattag ctgggcgtta tggtgggctc ctgtagtgcc agctacttgg gaggctgcgg    23340
caggagaatc acatgaaccc aggaggtgga ggttgtagtg agccgagatc atgccactgc    23400
aagccagcct gggcaacaaa gcaagactcc gtccttaaaaa aatttatttt cgttgttat    23460 tgttcatctc tctccacttt agtataagct ccatgagagc agggatactt ctttggatgg    23520
gggtctgttt tgtttattgc tgtatcccca gggcttagaa ctgtctagca aagagttgtt    23580
attcagtgaa catttattgc cttaatcagt gaaaatgtat cctccctggg aagcctgatg    23640
```

```
atgtagcaga agcaaactaa tgtaaatgct aaatatcgtt gaactcctat actttatctt    23700
aaaaatgtaa attttatact ttactttata tatatatata tatatatatt ttttttttt     23760 tcttttttt  tttttttttt tttgaaatgg agtcttgctg tgtcacccag gctggagtgc    23820
agtggtgcct tctcagctca ctgcaacctc tgcctctcag gttcaagtga ttcttgtgcc    23880
tcaggctcct gagtagctgg gattacagag gcgtgccacc acacccagct aatatttgta    23940 ttttttgta  gagatggggt ttcactgtgt tggccaggct ggtctcaaat tcctaatctc    24000
aagtgatcct cctgcctcag cctcccaaag tgttgggatt acaggcgtga gccaccgtgc    24060
cctgccatga tacatatttc tttattatgg acataatatt taaattactt agcattaaat    24120
gaaatcagag cttcaggaag atgccccttg gttattctgt ggccttgagt gtctcctctg    24180 ctctccctt  gtcttggtgg ccatgcccca cccccacagc catttggagg catactctaa    24240
gttataatta ttattgaaga caattaccat gaagcttaaa gtatcaagaa acaaaattc     24300 tcatttgcat aatgttcttt ataaggcagt agactgggat aactaaattt taaccataaa    24360
gctccttggg taacttagaa gtttagtttt tcattttatt cttacctctt catccccagc    24420
cacggaaacc tttgttacct ggagaaaaaa aatacccta  gagaaggatg tttaagatgt    24480
ttgatttgtg aaaggggcat ggattgatca gaaccacaac caccctttat ttatttaaat    24540
ttaattttaa ttttttttgag atggagtctc gctttgtcac ccaggctgga gtgcagtggc    24600
gtgatctcat ctcactacaa cctccgcctt ccaggttcac gcaattctcc tgtctcagcc    24660
tcccaagtag ctgggactac aggtgcccgc caccactcct ggctaatttt tgtatctttg    24720
gtagagatgg ggtttcacca tgttggccag gctggtctca aactcctgac ctcaggtgat    24780
ccacctgcct cggactccca aattgctggg attacaggcg tgagccactg ggcctggcca    24840
aaccactctt ttgaaaggga atcctgaaag ttaaattgta ctaaaaaaaa aaaaaaaagg    24900
aataatttca gattaagaag tacaaaataa tttaaaatta ttattttatt ttttaaagag    24960
acaacatctt actgtattgc ccaggctggt ctcaaactcc tgggctcaag ggatcctccc    25020
atcttggcct cccaaagtgc tccgaataca ggcatgagcc actgcattaa aatggcctgg    25080
tgtggtggct cacacttata atcccagcgc tttgggaggc caaggcagga ggattcaact    25140
ccttgagccc aggagttgaa aatcagcctg gcaacatag  tgagaccctg tctttacaaa    25200
caataaaata aaaaaattag caggcatggt ggtgcaagcc tatagtccca gctacttggg    25260
aggctgagac aggaggctca cttgagccct ggcatttgag gttacagtga gccgtgatca    25320
caccactgta ctccagcctg cgtgatagag caagaccctg gcaataagtt gatcaatcaa    25380
tcgatgttaa aaaatgatcg aaaatatcca ggtttgattc ctacctttgc ctcattattc    25440 atccctgga  ggctgaagtt attttctgta aaacagggat gattatgcaa cctatgagga    25500
ttcttgtgcc tggggtatcc cggcacacag cagcattaag aaaggattgg tcaggcgtgg    25560
tggctcacgc ctgtaatcta tgggaggccg aggtgggcgg ctcacctgag atcaggagtt    25620
tgagaccagc ctggccaaca tggtgaaacc ctatctctac tacaaataca aaaattagct    25680
ggatgtaacg gtgtgtgcct gtaatcccag aggctaaggc ctgagacttg cttgaacctg    25740
gcaggcagag gttgcagtga gctgagatcg caccagtgca ctccagcctg ggtgacagag    25800
agagactgcc atctcagaaa aaagaatgg  attaggccct tcccctcca  tccgtgtttc    25860 atctactttg gatatgaaaa aatgttaaat ttctataaat tagcaaattt aaactatacc    25920
aactagtata tatatgttgt ttttttttcct gaaagtttct ataagttgt  tagctaaaat    25980 cttatcaggt ttgttgtgaa tactcatatg aattaaggaa aatttcagca atgattggtt    26040
```

```
aatttacctg cagccctcag ggagaatcta cattgtagcc tgaagacata catttctaaa    26100
aatgactctc aaacaaggca aaaacccttg ttgaagtaga atagttacac attttatgaa    26160 ggtgggaaa  gcacccattt agatgagggg aaaaaaatat gtggtttaag ccccgttcat    26220
tttttaactt aaatgaaaca gtgcataatg aagaaatgtt ttgccaagaa taacttggta    26280
caatgaccgt ggtagatttt ggttacagaa tgtgattggg gtttaggagg acggtatctg    26340
cttctgatgt actgaagctc gggccttttca catccatgca ggtttccata gtcagcaaga    26400
agctgtgtgg ttgcagtctg agattccagc gcatgatgct gtttaagttt tgatgtaaac    26460
cttgggaagt gcttacccag gcctaagctt gctctttgtg gagtggctca agctcagaaa    26520
ggttaaaaac ggaggttatt taaaagtcac actcacaatt ttgaatccca tgtttataaa    26580
agttataaaa gagggccatt taaaagacat gctaacagct ttaggtcttt tgaatctttg    26640
ttctggtagt caccagaaca ggaccacgaa gtttatagag gccaggatgt tggacaagtt    26700
ttagctgaga cttgaagtag acggggggaga aagggcagag tgggactgaa catttgatat    26760
atttaaaaaa aaaaaataca tgtttcaaag agccgtggtg agaatgtgta aaatgccttt    26820
gaataatttc taaaagaaaa ataaggaaaa tatttcgtct tatccaggat tatttttagac    26880 aatattgatt ctgtaattta aaaaattaaa aaacaaaatt tttattgggc agcccctgag    26940
ccagaatagg ttcagagaag ctccttgatt ttgtaatttt gcttgaaagt gtgtgtgtgt    27000
ttaaattccc tgaaatattt tcagtttctg caatggctca catatagccg ggccactgaa    27060
tttacttgac attccaaaaa cataccagta atatttgtgg gattgccggt ttcaccatct    27120
ctctcataaa cttgatgctg ttaaagttgt catattctct ctcttccccc tgtagacgga    27180
gtcatgcttt gtcgcccagg ctggaatgca gtggcgccat ctcggctcgc tgcaacctcc    27240
gcctcctggg ctcaagcaat tctcctgtct cagcctcccg agtagctgga actacagtcg    27300
tgtgccacca cgcctgacta attttttgtat ttatagtaaa ggcggggttt caccatgttg    27360
atcgggctgg tctcgaactc ctgacctcag gtgatccacc cacctcggcc ttccaaagtg    27420
ctgggattac aggcacgagc cactgtgcct ggccttttcat attctctctt actgattctc    27480
cacatgtttc atggtttata atctctctcc ctccaggcac aagctgatga gctccttggg    27540
gaagggatgg tgtcatctct cacacttctg tccctcatgg tgtccagcac agtgctccgt    27600
gtataggaga gtctccaaac attcatgtcg aattgttgag tggaacttta aaatttcact    27660
tcatttcccc aagttctgc  caatactttg aacattttct tcctgggcca acactgcctc    27720
ccacactgac gctgagctgt tggctactgt ggactccttt cccagagggt gttccaaagt    27780
gtcctgaggt tgatggtcgt gccgtggtgt ttctgggaac agtgggtagg ggagggtgta    27840
aggggatggg caggggcctg tccaagattc ccttagcttc ccctcccctca gcctgccttt    27900 tccctcttac ctcctcctct ctccaaactt tgtccctgac cctggtgctt gggacctgca    27960
cccccttcac acctttccct gaaggagctg gggtctttct ccatgtattc tcttgtggat    28020
tcggtccttc agggatccag caagtggtta tggagcaccg tgtctttgaa caagccattt    28080
tctgttccct ggaattcctt tctttccttt cctttatttt tctttttttct ttttcttttt    28140 cttttttcttt tttttttttt ttgagacgga gtcttgctct gttgcccagg atggagtgca    28200
gtggcgtgat cttgactcac cgcaaccttt gcctcctgga ttcaagtgtt tctcctgtct    28260
cagcctccca gtagctgga  attacaggcg cccgccacca cacccagcta attttttgtat    28320 ttttttagtg gagaagggt  ttcaccgtgt tggccaggct ggtctcaaac tcctgacctc    28380
aggtgatctg cctgccttgg cctctcagtg tgttgcgatt acaggcgtga gccaccgcgc    28440
```

```
acggccttct ctttccttcc ttcatctaat ggaatcctac tcatcctcca agacccactt   28500
gttgggttat cttccttatt gggttgttcc taactttcct accaagaagt tgaatgtcca   28560
gtgaatgtgt gtgcttttt ttttaatttg tgcagtgcaa aaggatgaag cccatggacc    28620
taatctgtgg tgtccagatt gcacattaat gatgggccat ctttaaaaaa aaaaaaaatc   28680
ttgtacttac tgtctgtatc tgaagtgttt gccttggaca atgacttccc ttcccttcca   28740
ttcctttccc tttcttttt tttttgacg gagtcttgct ctgttgctca ggctggagtg     28800
cagtggcgcg atctcggctc actacaacct ccgcctcctg ggtttaagag attctcctgc   28860
tccagcctcc cgagtagctg ggattacagg tgcctgccac cacgcccggc taattttgt    28920 attttagta gagacagggt ttcactgtgt tggccaggct ggtctcagac tcctgacttc    28980
atgtgatcca ccagcctcgg cctcccaaag tcctgggatt acaggcgtga gccactgcac   29040
ctggccctga ctcttctttt ctttttttt tgagtgagaa tctcttcttc actcaggctg    29100
gagcgcagtg atgcaatctc cactcactgt aacctctgcc tcccaggttc aagtgattct   29160
catgcctcag cctctcgaat agctgggatt acaggcatga gccactgtga ccggctaatt   29220
tttgtatttt tggtagagat gggtatcacc atgttggcca ggctggtctc aaactcctgt   29280
cctcaagtga tctgcctgcc ttggccttcc aaaatgttgg gattacaggc gtgagccacc   29340
acgtccagcc aacaatgact tttcgaatgt tttgggactc gtcggagctt ggctctcctt   29400 ggatttctt agagtggatg taccattctg gcaaaactac ctcttgtggt tttataagtc    29460 agttttaaa acatttcttt tttaatcgtg actcaagaag acataatttt acttcacaac    29520
ccagtatatg gacaaacaca caagcacaca caagaattta gtttcatgaa acaaatttta   29580
ctcttactgg gattcactcg tctattttcc gttctgctag tctctcttct gctctatttt   29640
gttctcttgt attcatttaa aaatactggt atcaattcat cgaatggatt tcataaccca   29700
acaatgggcc acgacccacg gcttgatcag ccttctgtaa gccatgctgc agatgttggg   29760
atgttttcta aaacaggtgt gagtgtggag atcctccttg tgataaattg acttactaag   29820
gtgatgaact ggacaaaaag ctgagctatt gtctctgtgg aatttatgac tttcccgctt   29880
gttgaatacc agccatgctt gtcagcggag atcctgctcg gagggcattc cttgccgcag   29940
atgggtctat ccattcatct gttaatatgc atttggaagg agtcccgctg aattcaaaga   30000
cgaccagtga ggcccaacaa tgaaagctta gcttctgagg cccttcacag cagcttgctt   30060
tctgctcact ttttttgtaa ggattactct tcctaagcat tattcctatg gggaccagat   30120
gttccttttg cctgcctctt tatataaatt gggttcaagt cttcttgtga ttagaaatga   30180
gctccttcaa gtcttggtat tcaattcatg cattctgagt gtagttcatt gactcaggat   30240
gagagaaaca gattctggca gtatttacag agtttattag taagtttgga tccctggtag   30300
aggtgaatgc ttttgtttta gattttagg cacatttgtc ctgagtttta atattttcag    30360
tgatagagac aataataaaa cttcagggca ggatttctca gctttggaac tactgacata   30420
ttaggccaga taattaatta tttgttgtgg cgaactgtcc tgtatgttgt acggggttca   30480
gtagtatccc cctagcctta acccactagg tgacagtagc agaccccagt tgtgacaacc   30540
aaaaatattc ccagacatgc caaatgtccc ttggggaca aaatcactgt agttgagaat     30600
gactgcttta aggttgtacc agttcaatgc gcattcaggt tatttttctta catttcctaa   30660 cgtgagttat ctactaatga gagtgtatgg cttgtgtcac tggttttctt tacatttgat    30720
agactgcttg caaattaggt agttttatat gctgtaataa tttggaggaa ttgatcaaaa   30780
tgaaatgcta aaacctagaa gattctaaat ttatctatat ataatattta atttaataat   30840
```

```
agataatgaa agatctgaaa tgacagtttt aataagatct aatatcataa tatacaaaat   30900
cagacttaaa gctaaaattt aataatactt tgtgttgcat tattgaataa tgagtaggta   30960
atgacagacc tgaaacagca gttattatga gatctgatat cataacatac aaaattagac   31020
ttataactac aaattaataa tagtactctg ttgcatttcc cagtatttta gatggtttca   31080
catatgtttc cacacttgat tctcagtctg tgaggtagta gtgcagatat ttttatcctc   31140
aagttgcaaa tgaggaaaaa gaaattcaga aagcttgagc agtttgccca aagtctcaca   31200
tgctgtttga gagacagaag cagggcttaa cccgagttcg ctgacacaaa ccagactaga   31260
atttacggag actcctctcc ttagtggtta aagctgtccc cgaccctccc caaataaaga   31320
aaaccaagta gatattgcta tggttaatga tggctagccc ttttgttatc tggctcttgt   31380
cactatctga agtatttgcc tgggactagg atgagggtcc tagtttagta taagaatctc   31440
tctggagcga cgtgaagcct gttggtatct cctggtagta gcacttgcgc ttcctctcac   31500
ggtcttggcc agctgtagat ctcctttttt gcagtggctc cgttctgttt gctgtccccg   31560
atccagcccc cgccctcctc gcaggcctct gctcagcacc atctgcccac ccggagggtt   31620
tcctcctatt ccccttcagt tgctccatct gggcagccag ctcagggcct cagtccagag   31680
acaaagcaga ggcagacgat tctagttttc tttgctgtaa atgccacact acatggaact   31740
agagaatttg ggaatctgac tcatccaatc aagcccaggc taaaggcaaa tgaagaaaag   31800
gtaaatctcg aatttcctcc tgaaagctgt ttttccccgg gactcagtag atgacagtgg   31860
ctgttgggat tgtgatggca tacttaggac attcctccac attgctgcac gcttctggag   31920
tggttactga tcacactttt aagaaagaaa aacttccact cttggtaatt ttagcttaaa   31980
aagctacaga gcatactcat gtgaatgggg actgggaggg aatgcagaat ggaaggtagg   32040
atttggggga ttgggaggga atggagaatg gaagtdagga ttttggggat tgggagggaa   32100
tgcagaatgg aagtaggat tttgggggatt aggaggggaat ggagaatgga aggcaggatt   32160
ttggggattg ggaaggaatg gagaatgaa ggtaggatttt tggggattgg gagggaatgg   32220
agaatggatg gtaggatttt ttttttttgt tctaggtcca tgtcattgtg ataagttttt   32280
taaaattcca atatttatta taattgtccc gtaaataaaa aataattata aaaagtttg   32340 tacacagcat aaaatgtttg ctaactatac acattcttgg tgccacatta ttccagagtg   32400
acttcactta aattacgtct ctaccagccc tgggcctcgc cacacgttat tatacttcat   32460
atctcttcct gcaggttaga aaaccttcac aggggttgct gcgggtgact gtacgtatac   32520
atacttttgc tatttgtaaa caccaggccc ttttaaagta ctttttttt ttttgaaga   32580 gtttacatga atgaaatctg ttgttttta aattttttc agcccccttt ctattaacta   32640
aaatagtttt taaacttgaa tatcataaaa ttccctttagt aaaggagtca gggggccaga   32700
ggttactgaa catttgcctt aaatattccc ttgcttccag acaaaaatca tagctgaagc   32760
atgacagaaa aatatctgtt caatttgtca aattcctcag ggacaataat tacttagctt   32820
ccctcaggga gtatccttcc tgtcaataaa tttctcataa atattggata aattcttcct   32880
cctactgttt aaggctgttt tttttttct tccctgccag gattgaccca acattgcaca   32940
tttggtcagc attatgcata tgtgaaaatg cactttgttc tatatttctg tcactccctg   33000
tttgcttttc tctatcttaa ttatggaaat gtatcctcgt gagttgatat accagtcttt   33060
ctgtcatacc cagtaaggag gattcccgcc cttggtctgg ggtccgcatc aactgtgtag   33120
cacatgaatt gctgtcattt ggtcccacag gtgtctattg agtgcttata tgagcctcca   33180
ggtgctaggc cttgagtgca cagcatccag tagaggatgg gggtctcctg tgttttttaga   33240
```

```
aatatcccat gaaataaaaa aattaagcta tttaattgca aaagtagtaa gatgagctta    33300
ggttctaacc tgccgctggg gcagaaactt ccacctggga gtgattctgc ggctttgaat    33360
tctggcctct ttgtgtgtct gtgagtggct gacacagtcg gccactcaat cgcagttttg    33420
tccgctggtt ttggcgagct cagggcctgt gctgtgtgtg ctgcagctcg ggagggctga    33480
caaagagagg tggttgagga gtgagcggcc gggagccttt cgcctccagt gtcttcgctg    33540
gaccttggtc tttacaaaag gaaacaaatg aaggctcact ctgatccact cactgtgaca    33600
gtctgagtgg cagcagccag gagcttctct ggccatttgt agttccctca gttaaaaaat    33660
gaaagggtag ctaaggttca acagctcagg ctttgaactt tatttatttg tttatttatt    33720
attatcatca tcattttttga gacagagttg acagtcttgc tgcgtctgtc acccaggctg    33780
gagtccagtg gcttgatctc agctcactgc aacctctgcc tcccgattca agcaattctc    33840
ccacctcagc ctcccaagta gctgggatta caggtgtgtg ccctcacact cagctaattt    33900
ttttgtagtt ttagtagaga tggagtttca ccatttttggc caggctggtc ttgacctcct    33960
gggcttaagt gctccatctg cctcggattc ccaaagtgct gggattacag gcttgagcca    34020
ccatgcccag ccaggttttg aactttttttt ttctcttttg agactgagtt tcgctcttgt    34080
tgcccaggct ggagtgcaac ggcacaatct cggctcaccg caacctctgc ctctggcgtt    34140
taagtgattc tcttgcctca gcctcctgag tagctgggat tacaggcatg caccaccatg    34200
cctggctaat tttatagttt tagtagagac ggggtttctc catgttgatc aggctggtct    34260
cgaactcccg acctcaggtg atctgccctg ccttggcctc ccaaagtgct gggattacag    34320
gcatgagcca ccacacccag ctggttttgg acttttaaaa ggtggggttc ttgtggtcca    34380
gccccatgtg tgagatgggg ccaggttcta gtggcaagtc tagcagttgc tatccccttt    34440
ttagacgtgt gacacagctg cctactaaaa ggtagggtgc cggcagtata gcagccacct    34500
tctcagtcct cattaattag aggctgagct attggatttc ctgccaatgg ccaagtggaa    34560
aatctatttg acttttttt tttttttttaa tttaaatgt atctgcgtgg atagactcag    34620
gcaggagatt tgtctttgtc tttgttagag gaacctagct ccagtgtctt gcttctcctc    34680
ccactaactg taacagtcac cactgaggcc gggtgtggtg cctcatgctt gtaatcccag    34740
cactttggga ggccgaggca ggtggatcac ctgagagttc gagaccagcc tggctaacat    34800
ggtgaaaccc cgtctctact aaaaatacaa aaattagctg ggtgtggtgg cgggcacttg    34860
taatcccaga tgctcaggaa gctgaggcag gggaatcact tgaacccggg aggcacaggt    34920
tgcagtgagt cgagattgta ccgctgcact ccagcctggg taacagagtg agactctgtc    34980
tcaaaaaaaa taaaaggtgc cattgaaccc tcctaagaag atatacagta gccaataagc    35040
acatgaaaaa gatggctcaa tatcacttat cattagagaa atgcaaatga aacccataat    35100
gagatactgc ttatgtccat taggataact gctgtcgaaa aacagaaaat aacaagcatg    35160
ggtgaggatg tggaggaatt ggaactctgc tgcactgttg gtgagcatgt aaaatggtgc    35220
agctgttgcg gaaaacagta tggcggttct gtaaagaatt aaaaatagg g ctgggcgcgg    35280 tggctcacgc ctgttatccc agcacttggg gaggctgagg tgggtggatc acttaaggcc    35340
ggaagttcga gaccagcctg gccaacacgg tgaagccctg tctctactaa aatcagaaaa    35400
attatctggt gcaatggtgc gcgcctataa tcacagctac ttgagaggct gaggcagggg    35460
agtcacttgg acctgggagg cggaggttgc agtgagccga gattgtgcca ctgcactcca    35520
gcctggacga cagagcaaga ctctgtctcc aaaaaagag agaaaaaaaa aagaattaca    35580
aatagaataa cctaagtggt gtgcttatga caataaatag tttatttct aaaaataaaa    35640
```

```
taaaaataga ataacctaat gctattgcat ttccacttct gggtatatat cataaagaat    35700
tgaaagcagg gtctggaaga gctagttaaa cacccatggt catagcagca ttattcataa    35760
tagccaagag gtggaagcaa cccaagtgtc tctccatggg atgaatgaat aaacaaaatg    35820
tggcatgcac atgtaataga atgctattca gccttaacaa ggaaggaaat tctgacatct    35880
gctaccacgt ggatgaaact tgagggcatt atactaagtg aaataagcca gttgcaaaaa    35940
gacaaatgct ttcacttata tgcggtatct agagtcctca aattcataga ggcagaaagt    36000
agaatgacag ttgccagggg ctgtgggacc ggggaattgc tgtttaatgg gtgcagagtt    36060
tctgttctgc aagatggaaa gagttctgaa gatggatgtc ggtgacggtt gtacaacagt    36120
gtacttactg ctgccctgta catttaaaaa tgggtaagat gggccaggcg cggtggctca    36180
cgcctgtaat cccgcgctt tgggaggctg aggtgagcag atcacctgag gtcgggagtt    36240
tgagaacagt ctgaccaaca tggagaaacc ctgtctctac aaaaatacaa aaattagctg    36300
ggcgtggtgg tgcgtgcctg taatcccagt tactcaggag gctgaggtag gagaatcgct    36360
tgaacccagg aggcggaggt tgcagtgagc cgagattgtg ccactgcact cccgcctggg    36420
caagaagaac aaaactctgt ctcaaataaa taaataaata aataaatggt aagatggaaa    36480
atgttatgtt atccatgttt gaccacaatt acaaataaac tttttttttt tttttttaaag    36540 gaacaaaaag tcactattaa ggcctcaccc ctctgcttcc cgtgtctgtg gcttcgtgtc    36600
cagcagtgag cacggccaga ggggagcctc cccatctcag ccagtcctcc tccctttcag    36660
aagccctgcc ttatccctca gaggggggacc tcttgcccct gctaacatgt gcttgagaaa    36720
gcttttaatc tcatttatga ggtcaacctc tacaagctaa attattttaa ccaaggacta    36780
ttcactgtga tgtttatattt tgggctttgt ttttgctgct tggtcaaata gagaacaagg    36840
gccacctctc gtcacacagc ctgacgctcc tgcagcctg tgagactgag agttgttttc    36900
ctggtcatgg tgacagatga gccacgcatg actcactgga gcggtctccc ctgaaacaaa    36960
ggcatgcatt tgactgcaga ctgggtgttg agttggtggc ctttgcaaga ctgggtgggc    37020
agttctggct tcaaatgacc ctgatgaatc acacggttca cagacgtttc atttattacc    37080
ttgacagtga ccctggacac cagttgtttc ttcatataat ttgcgttaag gcttcctttt    37140
gactttgtgg gagcttggag taaaacgctt cacagagttt tcttgcgttt ctgtttttca    37200
ggctcacttc atggactcac tttgcgtgct tgttaaatgt gctgtgttgc tcccaagacc    37260
atgtaaagcc tactgaccac taacctccct cacagcagaa actagacgtc aggtaaaccc    37320
aacccttgtg cctgggggtc acgtcaagtt gcatgactgt gattaaggta ataagtaaag    37380
gtttaattat ttgggctagc gattttggtt ttaaatatt tgataattac caccaaagaa    37440
aagtcaatcc atttaacttc tgttttgtgg ctacacattc ttagatataa aagaattaaa    37500
aataaaaagc ctactaaata tatctggaga tctcaccaga agagcatcac ctccaactga    37560
cctaaaatag tgatatactg gtttgagtga gaaactagct gggcatggtg gcatgtgcct    37620
gtagttccag ctacttggga ggctgaggca ggagaatccc ttgagcccag gggtttgaaa    37680
ccagcctggg caacatagca agatcccacc tcaaaaaaat tatttcagaa tcaaagagaa    37740
tggtttcttc tttcctccct tcctcccctcc ctccttctcc ccctttttcac tttgagtttg    37800 gcttaactaa tagactcctt gagcaaactg gggtttttac aaggaagtaa gagtctaata    37860
ttaagttttt ctgatgccca tattctaagt cagcttcata cttacttctc tcatcatatt    37920
ctaaagtgaa gatacctgaa gtcttttacaa aagctctaga gattagtttt attaaaatgt    37980
ttttctttcc caaatgagag ctcttatttt ttcccccatt tttcatctca gcctcatttt    38040
```

```
tgaggacttc caggcctttt tcttttgtgg tattcctaga gccccaacag agcctggtac    38100
ctggtgtcat gttataaaaa tgtgatagtt tttgagcaaa agtctctcaa aatactgtgg    38160
agagatttta gctctaccag tagtttatgt ataatgaaaa tgtatctctc tgatcactga    38220
gatctgtgta tttagactga cagaataaag atactttccc taattttcct cttcaagaat    38280
cattagtttg gtcaggtgtg gtggctcaca cctgtgatgc tagcactttg ggaggccgag    38340
gcaagaggat ctcttgagcc caggagttca agaccagcct ggagcaacag agtgagaccc    38400
catatcttta aaaaaaaaa aaaaccccga gcttgagagt ggtagcacgt gcctatagtc    38460
ccagctactt gggaagctaa ggcaggagga tcacttgagc ctaggaagtc gaggctgcag    38520
tgagctgtga ctgcggcact gcactccagc ctggatgata acagtgagac tctgtctcaa    38580
aaaaaaagca aaaaaaatc attcaaagtc tctcaacacc aagcctgaag cagatctttc    38640
tcataagctg attttttatgc ctgttcgcct tctaaattaa tattgtataa tgaataatgt    38700
cttttaaaata attagcagac aggtgtgcag tgttgtctgt ctagctaatg agcagccttg    38760
caaaataagg agagcctgtt ctactgactg actcttgtcc ctactcctct gagtccttcc    38820
aggcactgaa gttgctgtgt aatatgcagg gcattcttt tagaaagttc tgtcataatg    38880
gaatgtaatt taggccacgg tcttactgat gcaactgttc ttaatttagg ttaaaatggg    38940
caactccgac agtcagtaca cccttcaagg atctaaaaat catagcaata ctattactgg    39000
tgctaagcaa attccttgct ccctgaaaat acgtggcatt catgcaaaag aggaaaagtc    39060
attgcatgga tggggtcacg gaagcaacgg agcaggttac aagtccaggt ccctggcccg    39120
aagctgcctt tctcacttta agagtaacca gccttacgca tcgagactcg gtggcccac    39180
atgcaaggtc tccagaggtg ttgcctactc cacgcacagg acaaatgccc cagggaagga    39240
tttccagggc atcagtgctg ctttctcaac tgagaatggc ttccactctg ttggccacga    39300
gctggcagat aacccatca cctccagaga ctgcaacgga caccttctca actgctacgg    39360
gaggaatgag agcattgcct ccaccccacc gggcgaagac cgcaagagcc cccgagtgct    39420
catcaaaacg ctggggaagc tggatgggtg tttaagggtc gagttccaca atggtggcaa    39480
ccccagcaaa gtgcctgcag aggactgcag tgagccggtg cagctgctga ggtactcacc    39540
taccttagca tcggaaacct cccctgtgcc tgaagccagg aggggtcca gcgccgattc    39600
cctgcccagc catcgcccct ctcccacgga ctctcgcctg cggtccagca aaggcagctc    39660
cctgagttct gagtcatcct ggtacgactc cccttgggc aatgctggag agctgagcga    39720
ggctgagggc tccttcctgg ccccccggcat gcctgacccc agtctccatg ccagcttccc    39780
acctggcgat gccaaaaagc ctttcaacca aagctcttcc ctctcctccc tcgggaact    39840
gtacaaagat gccaacctgg ggagcctctc cccctcaggt atccgccttt ctgatgaata    39900
catgggcacg catgccagcc tgagcaaccg tgtctctttt gcttccgaca ttgatgtgcc    39960
ctccagagtg cacacggggg accccatcca gtacagttcc ttcactctcc cctgtcggaa    40020
gcccaaagcc tttgttgagg atactgcgaa gaaggactcc ctcaaagcca ggatgcgacg    40080
gatcagtgac tggacgggaa gcctctcaag gaagaaaagg aaactccagg tgagcatacc    40140
ttagagcaga gggaagggtc cccacagttt ccccacctgg agaaggggaa ggttagtaga    40200
agccaccata gagtgttgtc ggggtgctta agtgatctgg caaagtgaa gagttcagtg    40260
gaaagcctgg ctcatctcat tttcaagtgt gggtttgttc tctcttttgc ttcagatatt    40320
ttcactttta gccacaaact ttaatcttcc catgtcttag tcagcttggg cagcaaacaa    40380
aataccacag acttggttta atcaacagac atctatttct cataattctg gaggctggaa    40440
```

```
gtcagaggtc agagtgccag tgtggtccga ttctggggag ggctctcttc ctggctgcag    40500
acagccgcct tctcactgtg tcctcatgcg gcagagagag caggaggtct aggctctttt    40560
cctcttctta taaggaccct aatcccatca tggggactct accctcatga cccctctaa     40620 accaattacc tctcaaagat gtcagttaaa tatcatccac tggtagttaa ggcctcaaca    40680 tggatttttgg ggagggggga aacaaatgtt cagtcaatag cattctggtt ctgtgcatgt   40740
ccctgcactc ttccatgcac tccacaggcc taatcttaag acttggccat agccggtgtg    40800
gcagctcatg cctgtcatcc cagcacttgg ggatgccaaa gtgggcagat cacttgaggc    40860
caggagtttg agaccagcct ggccaacatg gtgaaaccct gtctgtaccc aaaatacaaa    40920
aattagcctg gcgtggtggc gggtgcctgt aatccgagct actcaggagg ctgaggcagg    40980
agaatcgctt gaacctggga ggcagaggtt gcagtgagct gagatcacac ctgggcaaca    41040
gagagagact ctgtctttaa aaaaaaaaa aaagtaagta cagagttgga gagaattcct     41100
gaaagaattg gttatctgag aattttacta gacctcattc ttacagtcca aataaaacag    41160
ttgagattgt cattattttt ggttgaatag gcttgttgaa cttgatatta ctctgatgaa    41220
attaaaattt ctatgcttaa gttggtacat caaaaaaaaa agttgatgat atatctacat    41280
gtgtaatctt ttttttttt ctttttttg agacagagta tcgctccgtt gtacaggctg      41340
gagtacagtg gtgcgatctt ggctcactgc aacctctgcc tcccgtgtcc aagcgattct    41400
gctgcctcag cctcctgagt agctggcatt acaggcgtgc accaccatgc ctggctaatt    41460
tgtgtatttt agtagagacg gggtttcacc atgttggcca ggctggtctg gaactcctga    41520
cctcaggtga tccacctgcc tcggcctccc aacatgctgg gattacaagc gtgagccacc    41580
acatccggcc tatatgtgta atcttaacct cctcatggag atagctaatg gcatcctgaa    41640
aatatcttgt acctaagtgc atgtaataga aaaatatata tactgataaa actgataaaa    41700
taagaatgat gaatatactt ctgtatcatg gcatgtaaag ttttactggg ggagcaaagt    41760
ggcttatcca ccaggaagaa aagtgatagt ttgcctttt aggtaattag tggcaattgc    41820
tagattttca gtttgttgtt gttttgttat ttgttttat ttttgattat ttatataggg     41880
gagaagcttc ttttaaatt actctgtata agtcatggag ttgaagggaa tttgtgtggg    41940
cagttagtct ctagcagaat tgcatcctag atagacataa aattataaaa ttatatagag    42000 atttagggggt ggaaaataat ataacttttt tgagtagatt gcttcagatt tatgaagttt   42060
gactttcgtt acttccttct gatgtatata gcgtgtctgc ctccaccacc ccctcctgtg    42120
ctgggcttcg gttctccctc ctcttccttc acacagaggt gaagaacaga tgatcagcat    42180
cctgttttca gggcctcttc atatccctga atatattgta gtaatttgta tagtgatttt    42240
actcctggat catcactttt tcagactaaa ccacaaaata gtagagattt ccttgacttt    42300
tttctctcag ctcccatttc ctaaacaact gatccccact gagcataatg ggagacgcag    42360
cttctgctta cttgagggct gaagtcccag gtggacaacg tccacgcctt tttgattcaa    42420
gtgttatggt gcccacctgt gttcagctgt catccactgt gtccctaat tggtggtggc     42480 atcgagccaa tgattctgca tctcttatgt gcactgagtt tgttgctcat ctgtatatgt    42540
ggcctggctt acacgcggct ctagtgagct gcattcagtg acagttccca cttggttcag    42600
atgtagacca gtggctgctg tgtatgaatc attctatcac gggtaagtat ccctccttgc    42660
ctctcctgtc aagttaccct ccctgcgtct cctacccacg ggaactgggt ctccttcaat    42720
tctgcattgt ccaaaaactt aactctgaat tgtgtgcctg tagagttaaa aacaaaccgg    42780
ttagggccgg gtgtggtggc tcacgcctgt catcccagca ctttgggagg ctgaggcagg    42840
```

```
cggatcactg gaggtcagga gtttgagacc aacctggcca acttggtgaa atcccatctc   42900
taatgaaaat tagctgggca tgctggcatg tgcctgttag tcccactact tgggaggcag   42960
aggcaggaga atcgcttgaa cctgggaggt ggaggttgca gtgagctgag atcacgccag   43020
cgcactccag cctgggcaac agagtgagac tccatctcaa caacaacaac aacaacaaaa   43080
cagcaacaac aacaaaaaac tggttagaat caaggaatta gaatttttatt atttatttta   43140 ttttatttat ttattttttg agatgggagtc tctctgttaa aaaaagtacc ttcttagcaa   43200
atttcaggca tagaatatag tgttattaac tgtagtcacc ataatttacc ttagagctcc   43260
agaacttatt cctcctgcaa aactgaagct ttgtaccctt tgagcagcat cttcccattg   43320
ccctctcctg cccctggcaa ccaccattgt actctctgct tcaatgagtt ggactatttc   43380
agattccacg tataagtgga atcttgcagt gcatgtcttt ctgtagagtg acatctcttg   43440
agtttttact cttttttttt tttgagatgg agtcttgctc ttttttgccca ggctgtagtg   43500 cagtggcgcc atgtcggctc actcaagcga ttctcctgcc tcagcgtcct gagtagctga   43560
tccggattac aggcgtgtgc caccacccc agctgatttt gtgtttttag tagagacggg   43620
gtttctccat gttggtcagg ctggtctcga actcccgacc tcaggtgatc caccctcctc   43680
ggcctcccaa agtgctggga taacaggcgt gagccacctg gcttgagttt ttactcttga   43740
gtctttactc atctccactc tgctgtactg ccctagtcat caagttacat tagcccttgt   43800
ttctgattat tcgatttgat ggaagtgaag tcacttgtat ggaaatggaa atcgtatgat   43860
ttgtgtgtgt gtgtatatat atatatatag caggcacctt agtttcatcc gcataacaga   43920
tgattaagaa ttctagctga acctatttaa agacattcta tatttttttaa aggctctttt   43980 ttattagcct gaaaattagt gactggctat taggattcta gataaaaaga tttggaaatt   44040
tattagagac tgggagagtt catacctatg tataagaata agttataaat gctaaaatgc   44100 atcccccac ccccccccat ttctgaaaaa gaaaactcct tgctttgcta tggttaaaca   44160
tttaaaagtt ggcactgtaa gttgagaagc agtgtcaaga gtgtgtgtag gtcacactta   44220
actttgggac ttctgtgcct ttctgtggca gaattgggct tgttttgaag catattccgt   44280
catgcccctt gcagggtatc agaggtaatt ccagtgtttt tgggcgatga gtcagaggga   44340
catatttata actgagataa tgttaatact agctagatga gaagtgtttc ttcaccttt   44400 aggagttttt tgttttttg ttttgttttt cttttgagac agagtctcgc tctgtcgccg   44460
aggctggagt gcagtggcgt gatctctact cactgcaacc tccgcctccc gggttcaagc   44520
gattctcctg cctcagcatc ccaagtagct gggactacag gcatgtgccg ccgcacctgg   44580
ctaatttttc gtattttttg tagagacggg gtttcaccgt gttagccagg atggtctcga   44640
tctcctgacc tcatgatctg cccacctcag cctcccaaag tgctgggatt acaggcgtga   44700
gccaccgagc ccagccagga ttttgaaaa agcaacaaat tgacaattaa aaaaaaaact   44760
ctaagtattt ctaaagtttc ctgtccaagt gactcacaac agctggttta tttgctctgt   44820
tatgcataag catcagtgta taaataaata tgactggaga tgcagtgtaa acagtggcaa   44880
atcatatttc tatttgtaat atctgcttgg ggcgcagttg ttcatggctc ctgggtattt   44940
ggaagtactc tccagttgtg tgattattct cttacaaaac agcaagtaat tgcaacttga   45000 ttttttggatg aaatttctga aaaggaaacc tctctataca atgtaatatt caaaataagg   45060
cctttagtca atggtccttg acccagtttt ccatcatttt tattttaatg cataagaaaa   45120
tataatcaaa agcccactag cagctgagta gtcttgagtg tgcttggcgt ctctgcagag   45180
ttatcttcat ttaagccata aatgttgaat gtcagtgcct tttgagtcag aagttaagct   45240
```

```
cactttatgc tgaaaatttt aattactgcc atttaccagt gaaaagcctg tatgcaaatt    45300
atttttcttc agtgactaga cttctaatcc agatattaga gaaatgtctt tatgttttca    45360
gctctgtgca tggccagctt gatgttcaat gcacctggtc ctcacaggga gcaacattat    45420
tatataagta tgcattgtat ttagagctac ctgtgtttga tttttgtgtt ggagtaaata    45480
ctgcagttaa gaatcatgtc tttgatatct ccagtaccta gaataaaata ggtactcaaa    45540
tgaaaggatg tgaatgaata aatgggtata ttttttttcat gaaagtaatt ctctaagtaa    45600
gaaatattaa ttatgaaaaa aactggccgg gcgcggtggc tcatgcctgt aatcccagcg    45660
ctttgggagg ctgaggtggg cggatcacct gaggttggga gtttgagacc agcctgacca    45720
acatgaagaa accgtgtctc tactaaaaat acaaaattag ccaggtgtgg tggcgcatgc    45780
ctgtaatccc agatacttgg gaggccgagg caggagagtc acttgaaccc aggaggcaga    45840
ggttgcagtg agccaagatt gcgccattgc actccagcct gggcaatgag agcgaaactc    45900
catctcaaaa aaaaaaaaaa agaaaaacaa aaagctata gttactagcc agtacccttc    45960
atagataagg aatcctaagt gtattattat tgttattatt tttgagatgg agtttcgctc    46020
ttgttgccca ggctagagtg caatggcctg atcttggttc acagcaacct ctgccttcca    46080
ggttcaggtg attctcctgc ctcagccccc tgagtagctg ggattacagg tgctcaccgc    46140
caggcctggc taattttttgt attttttagta gagacgggtt tcaccatgtt ggccaggctg    46200
gttttgaact cctggcctca ggtgatccac ctgcctcggc ctcccaaagt gctagaatta    46260
caagcatgag ccacctcgcc atctattatt tttactatat gaactgggaa ataagatac     46320 tagagatctc aaagtctaga agtctagacc tgggcacttg gccagaagct ggggactata    46380
gggagaggaa gagaagttttt tgggttttgc ataacaatac tgagtccctg tcttccccac    46440
cctaccctgg tatagtaatt ttctaattta cctttcaaat gatccaggga aaaataaat    46500 tgcaagaata tgaattcttt cctggaagat actgattcat ggttagcaat gaagaaagaa    46560
atatcattct agtaatcttc actagtgtgt tgtaaacata ctagttaatt tctcgatgct    46620
aagcataggt tagatttagg agagccattt gtattttatt tacctctttta agtgctaatt    46680 ctactggata taaattgact tgggcaacac tatttttaaa attctttctg gtatgaagac    46740
ttgatggtta aagatgtatt tttgttacaa gaatcttgct ttgcattaca ttatcagcag    46800
ccactggtat tacacttatg ctgtgtgcaa gaagggatgc tttggatagc cgtaagctct    46860
gatgggtgat catgtgtgtt tctcacagga gccgaggtcc aaggagggca gtgactactt    46920
tgacagtcgc tctgatggac tgaatacaga tgtgcaggga tcctcccagg catctgcttt    46980
tctgtggtca gggggctcta ctcagatcct gtctcagaga agtgaatcca cacatgcgat    47040
tggcagcgat cccctccggc agaacattta tgagaatttc atgcgagagt tggaaatgag    47100
caggaccaac actgagaaca tagaaacatc tacagaaacc gccgagtcca gcagcgagtc    47160
actcagctct ctggaacagc tggatctgct ctttgagaag gaacagggggg tggtccggaa    47220 ggccgggtgg ctcttcttca gcccctggt cactgtgcag aaggaaagga agcttgagct    47280
ggtggcacga aggaaatgga aacagtactg ggtaacgctg aaaggtgagt gcagtgtcac    47340
ctgctgaggc cactggggat tgtttccgcc agccgtgctc tttgccagga agtgccaaga    47400
gactagcatt gatttgagtt cacatgaggg gtttgacaca ggatccatgg gctgccttca    47460
tgcagatact ttctcacacc cgtgaaatag gctttaccta ctattcacat gtattatgca    47520
gttcaataaa taattagtgg atttttttact tgttttttatt tttttttgaga cagagtcttg    47580 ctttgttgcc caggctggag tgcaatggca ggatctcagc tcactgcaac ctctgcctcc    47640
```

```
caggctcaag caattctcgt gcctcagcct cctgagtagc tggaattatg ggcgtgggcc   47700
accacacctg gctaagtttt gtctaatttt tagtagagat ggggattctt catgttgacc   47760
aggctgctct cataactcct gacctcaagc aggttgtcca ccttggcctc ccaaagtgct   47820
gggattatag gcatgagcca ctgcacccgg cctattataa tggttggatt taatacttat   47880
tgcttatttc ataggtattt agcttattta taggtatgcc tgtaccattt tcgctggatt   47940
tggagaaaaa aaagtcagta accaaaggta gtttagttgt ttggaaggca gcttctgaat   48000
ttcacattcc gtacatgttc agaactccaa agaggttttc tttccagctt gtgcaactaa   48060
gattatcatc tggattattg atttgtcatt ccagctttat gaacaaagtc tgtttgttgt   48120
catcactaac aagtgcagcc gtcttttttt tttttttaata tactttaagt tctagggtac   48180
atgtgcacaa tgtgcatgca ggtttgttac ataggtatat gtgtgccatg ttggtttgct   48240
gcacccatca actcgtcatt tacattaggt atatctccta atgctatccc tcccccattc   48300
ccccatccct caacaggccc cagtttgtga tgttccctgc cctgtgtcca tgtgttctca   48360
ttgttcaatt cccacctatg agtgagaaca tgcggtgttt ggttttctgt ccttgtgata   48420
gtttgctgag aatgatggtt tccagcttca tccatgtccc tgcaaaggac aggaactcat   48480 cctttttttat ggctgcatag tattctgtgg tgtatatgtg ccacattttc ttaatccagt   48540
ctatcattga tggaccagct gtcttttttt tttaaacata aaggcaatag aagtgagaat   48600
ttgttttgtt gacatgagaa aagtttttta taagcattgc catttaaaaa ctataattgc   48660
cttgaggaag agagaagctc caaatctgta cagcgttgat ttatgcagat gcacccagag   48720
cggcctcgca gcctctggca ttctgcacag ccccctggga ctctttgtca gaggagctga   48780
gtgtgttgtt caaagccaa acctcatcgt caagtgatgc ccttccctgt cacaggagag    48840
agcagaaaca tctgcaaata ctacgtgtgc aatgtccagt gccctctcaa ttacccettt    48900 ctagcttttc tttgcccctt atcgaacagt tggagccctg cttccccaac cgtggagggc    48960
aggcatcatg ccttcgttac cacaagcccc tctggcacct ctggtaaagg agcacttgca    49020
aaggcatttc atatccaagt gataccttt cctagcaggc cggcgggtgt acaaagccca     49080
ggggcccagc attcctcaca cgctgcagtc ctcttttcca tccctagatt tggatgcttg    49140
tagacattgt ggctggctga ggaaggtaaa gaacgtcccc agttttcca tactggcgag     49200 gcagatttct gtattgaatg acagaaacaa tttggaaagg tagaataatg ggttgaatct    49260
ggcaggatta acatttaaag agataagaaa gttctgcttt aaggtttaaa agtcagatag    49320
ctacccaagg acaggatagg gaaatgtggc tgcaaactat tatgagtgag gccaggtgtg    49380
gtggctcaca cctgtaatcc cagcactttg ggaggccgag gcgggtggat ctcctgaggt    49440
taggagtttg agaccagcct ggccaacatg gtgaaacccc atctctacta aaaatacaat    49500
aattagcctg gcatgatggc aggttcctgt aatcccagct actcaggagg ctgaggctgc    49560
agaatcgctt gaacctggga ggcggaggtt gcagagagct gagatcatgc cactgcactc    49620
cagcctgggc gatgagtgaa actccatctc aaaaacaaac aaacaaacaa acaaaccaaa    49680
acaagtatta tgagtgaaaa agatgtcggg atttaatttg caggccatgt gtttccaagt    49740
tgatgtggct gaaaaggtaa atgtgatttc aaagagcaaa tgtgatcttt agctacctca    49800
ttagagatgt catgtgatca tcagctacct ccttagaaat gctatatctc ttgcaaagga    49860
gatgacagtg tctcctttct ttgccctggt cagagctggt tgtttccctc cttgtgggca    49920
caatattgca ggagatttgt taggaaatga gaaattgatc cttgaaaggt tgtcctggag    49980
gatccctaaa tggggagaga gtgaacatgt tcccttaagg ggtaaacatc tgggactgtt    50040
```

```
tgtgaatcat agtctgaagc tgcctcctag tcacatgatg tgaatactta gaatggatgc    50100
acgttacccc atcatttgtc atgtatctac ttttttaagtg tgaaatttgt ttcttaaaat   50160
taattctgtg agaatttctt ccctgcctgt ctatggattt gaaaacccc agtatacatc     50220 accctagtgg tgggggttag actgggaggc agggtgactg tgtgtgtatg tgtgtgtgtg    50280
tgtgtgagag agagagagag agagagagag agagagagag agagagagaa tataccactt    50340
tgagaggctg ggccataggt gatgacaagg agatttagag ccgtgctaga tggaggaggg    50400
cataaagatc tagggatatt tagcatggag aaaataagaa ctgggtgaga gtgaacagca    50460
gtgtgtagaa gagacattga atttattctg ggtctgcaga ggttaggatg ggactaatag    50520
atgggagaca ggctgattct aaattaatat aaaaaacaac agtgacagcc atgggcacgt    50580
ggaaagatgc tccctttttg atttctgtgc tactgaccac atttgtccag agccaaattg    50640
tcgcaggctt cttgagggaa actcaggcag atatcactta agggctggaa gagctgattg    50700
gcagcttcct gtattttatc ccaaaaggta gaccaggaac ttctggctac caacttcagg    50760
ggtagtgatg ggcctgagtt gtcactgagc attgctagat ttgtagtctt ggctaggtcc    50820
tgctttcctg gtgtttgctt gtaaaacact tcaagatcca tggataaagg gtgctttgta    50880
gtataaatgt tatcaagcac acatttcttc ctttcctttg cagccaaggc aagacttgtg    50940
ataaagatgt ttttttcccc agcgtaacct tttccatgtg gctttctaca cctcttcct    51000 ctgggaattc agtatgttga gttctaattt cttggcttag aatccaagtt gtaatgtttg    51060
gacttaactg tttggtttaa tcttagttaa aaacacatat atgtgtacac acacacac     51120 acacacacac tcttaagcct aattttaaa ttatccttaa agtatccatg taaataaatg     51180
ggagacagtt ttctggagag agccgttatt aacaaaccat ctggttatct gcctacctgg    51240
aatgtatagg tatatgaggg acgtacatgt ttttcaaggc tttggaggat gtaataaatt    51300
ttcaacaagg gtaattctgc tttccatttg tcttttccag tgagtggatt ttcatgcagt    51360
tcactgggga cttcctgggc tgaagagttg gcaaggtcat taaacatatc cctcaaaatg    51420
tgcaacagac tgagtgatag tcagtgtcag gggaggagtt cataaactaa ttttagaata    51480
ctggtgattc tgccctgaga tgggccagca gcagggatgg gagatcaaaa gggtctcata    51540
gaaaaggtgg atttgaggga aaaccaagac taattgccct cttcccctg ggtgagattt      51600 ctactaatat tacgtctcta ttcttgtact gccattgcta tgccaatctg ttttctcttt    51660
ctgctaccat agcaagaacg tccagtgtca acgacccctc caagccaaga ccagcgcttg    51720
gtagggactg acagggctg ggggcccccca gcaccgggt gaacggcaag gcagggctgg      51780
tggcccccag catcggggtg aacggcaaag gcagggttgg gggccccag caccggggtg     51840 aatggcagag gcttcactga cacgggtgca gcccgtttcc actggcccca gtgcacccctt    51900 agagatgcag agtcccgtga agttgaactt gatgtcatag agttaagatt gatttcctga    51960
ttttttaaat ttgatagcca caaaattctg cctattgttt tacttcctgg cctggctcta    52020
atgtgaaatg tcctgttttg atttcatgcc tccaagttag agcggtagtc tgttgtccat    52080
gggttgttag gttggtgac attttggcat tggcccaagg tttgcattca ttcctctag      52140 atgccacgat ttaaaccatg gctgttggaa ttccagtgtt agggaagctg ggaagtgaac    52200
gtgaacccat tggaaagaat ttggacgtgt gtgcagctgg agctgctctg cccctttgcc   52260
ctggtcctcg ggccccgggt catggcttgt agcatgtgca acagtagcat cagatgggcc    52320
ttactcgatg agaagacttg gtttatagtt taactgctgc atcagtggct ggaaaaagat    52380
actggccagg cctgcaagaa gcagctctgg ctgtaaacct cttgctactt tcccttgttt   52440
```

```
gtaatacttg agttctgtca gcctgttagt ttggatgagt tttatttgcg gggaggagca   52500
aatgcgcagt ttcttgagat cataaagtac catggaggga gaaagtactg cttccgaagt   52560
ccaagcttgg agcaggcatc tttctctctt ggcttctatg tgctgttatc ggttctattg   52620
tataaacttg tttgttcata tcaagactta ttttaaagg aagtaatgaa attggaaaga    52680
ctgaaatagt tttcaaaacg tctgaacttt tatgaatgag gatgcaaaca cagtagtagg   52740
ataaagtacc gtgaagtggg ccccaggcat ttgtttacag tgaaggcagg ctggtgtttc   52800
tttcctgtca atgtgaaagg cacttgcgaa gcacccagat ggtggtcatg tcattgttat   52860
tcgtatgctg gaggttgcca catgagaagt ggtcaaaaaa gtttattgga tacagatttg   52920 agggatagt taacctatac aagaggacac atttgtgagc attttagaag cattagtttg     52980
cttaaaaatt gtgtctaata attataatgc aatttctaat taatgaagca aactcttaat   53040
aacttctacc tgcaatactt tatttgctta tgaggggaag agtaagtact taaaagcata   53100
tgttgcagta ttttagagt aacgtttgaa aattcaggca catttagttt cacttttctc    53160
ccttagtcta agtaatgttt tctattagtt tcactttct cccttagcct aagtaatgtt    53220
ttctattact gtgagataaa aggaaatact aaaaattaag ttattttaca tggcatttgg   53280
agaacaaacc gggtactttc tcataaatgg caaagtcccc taggtatgtt cagtttcttg   53340
ttcccattga tggtcaacgg agtgagtgag tgtgggattt tctgtggcct cttacattga   53400
gattccctaa ataatgtggt gttgtgctta aggatgaggg ctttgggggcc agagggcctg   53460 agttcacatc cctgctgctc cacagtgcag cggtgggacc cctgcaagga attcgatctc   53520
tcagttttct cattttagt gtgaaaggaa aataaaacct ggggacccca attcctgatg    53580
ccagaaggaa aaaaaaaaca agccgaaagc tgagtcatgc aagaagctgc ctttcctttt   53640 cttttctaagc aggagctaca gataaaaggt taaatatccc cacaggtagc tagctactct  53700
gtgttcacct tatcttatgt aaagtgctgg atgattacgt gattgacagt tcccctgcct   53760
gctccttttc ccttgcagca ggtggattac catgctctcc ctcgttcctc tccagcccac   53820
ttttaatttt taaacactga agccctcaac atcgtctttg gagaaaagca cagaccacag   53880
actatttctg tgattctgtg ttctcttcct ccgggcatgt ccacaacttt ggcaaaataa   53940
acttctcaat ggatcgagac cagtcctaga tacttttgg gtcacagtag aatgggctaa    54000
ataaccctgc ccaccttagg gcctctatgg ggattaaata agccagtgca tgtggagtac   54060
ttagaagagt taagcaacaa cttattattt ggtattgtta ttactgatat tacatttaca   54120 aagcatctc atttcattc aagttcattc tgatacaact aggtgtactt cagatgccac     54180
ttttccttgt ttaccatgtt tctgtcacat gattgtctca ctcaggtgtt tttaaaaaag   54240
tgtgtcactt accctcccag tccttttcctg catctccagg tctgaccggg atgttatttt  54300
gcttctctgt ttcacaggat gcacgctgct gttttatgag acctatggga agaattccat   54360
ggatcagagc agtgccctc ggtgtgctct gtttgcagaa gacagcatag tgcagtctgt    54420
tccagagcat cccaagaaag aaaatgtgtt ctgcctcagc aactcctttg gagatgtcta   54480 cctttttccag gtactgctgg tactttgtaa gtggaggtaa tagcttatgt actgctagaa   54540
taagaaggaa cagaaaaggc aaaacttgga aatgaaattg aataaatact tagttaggct   54600
ttggatttgg ccttaagcaa cagatgttgg cttccgctga ctgccaaggg cactgggcca   54660
tcagcaatcc agtcattcat ccagagggca cttttcaggt gcctctgaag tcccaggctg   54720
tggcccatga gatgctcatt gggacacaaa gagaaaaaaa tcatgatccc tgtcctggag   54780
tagctggcga tctagtgagc gcaatggtca agattcccag atttggggct tttaaaatga   54840
```

```
agcttggaga atattgatgg gagaggcttg ggttcttgcc acggatctca gtggatgtca    54900
aaagttttca ggaaaaccct catagacaaa tgctatgagg tctcatttcc ctgtggaagt    54960
ggtcttagga tcttaagatt caggttatct actgttagaa ttttcagtga cttttttagcc   55020 agtgagatgt tgtagaacat ggcggtactg agccatcggt attggggtcg ggcttaggtt    55080
tgaatcctgg caccttttgtt agcgttgagt ttgtaagtga tcttggagcg cgtaccagac   55140
ttctctgagc tttgggccct tcaaccagta ggataatagt ggcttacatg attgccgtaa    55200
gagtaaatga catcgtgtgt gtgttaaatg cttaataaat tttaacttgg tgattaatat    55260
taattcagaa caggtgagag tgagagctgg gaagtgaagt gtgcttctta aatgtccccc    55320
atctaaaccc agcacttgac atacacacag tgttggccgt aggttacatc tgactggaag    55380
tttcatggaa agcctcgtaa agcttgggtt tagatctctc ataaggatgg tcctgggtgc    55440
cctcagaagc cctgcagagc aacagtgttc tctaggctga ctttgggagt ctagaatgct    55500
cagaagtgct ccctcactta cccagtgctg gttaagctc cctgggcctt taattgtact     55560
gccattccca acctgactta acttactaga gccagggcct gagatttgat tttccttttc    55620
ttaacagaaa ggttgcttaa aaccttctat gatactttaa agcaaagtaa tgaatttatg    55680
ttagtctgaa ttgtaaggaa ggtaaaaaaa caaacaacaa caacaaaaag ttacattaaa    55740
tctgcatgga tttcttaggg tcaagtgtga aatgaatgtt ttattttgtg attcaggtaa    55800
aacatcctta gttttgagag tttccccgcc tgtgatccca gcactttgga ggctgaggca    55860
ggaggatggc ttgtggcgag gagtttgaaa tcagcttggt cagcatagcg aggccccatc    55920
tctacgaaag aacaataaaa aaattagcca ggcatggtgg tgcgcacctg tggtcccagc    55980
tacttgggag gctgaggctt gaggatcatt tgagctcagg aggtcaaggt tacaatgagc    56040
tatgattgtg ccactgcact ccagcccagg cgacagagtg agaccctgtc ttagcaacaa    56100
caacaacaga attttcccag gtgttctgtt ttgtgatccc agaggccact tgaggtttga    56160
ccctgtgact cgaatgtgtg tggttatttc tagacatcaa gagaaatgaa agtacttgtc    56220
agcctgctta gaatcatacc catttgccca ctttattcaa actttgctta ttgttttttaa   56280 aatattttc ttttaaaaaa tgtatcatta ttattattat tatttgagat ggagtcttgc     56340
tctgttgccc aggctggagt acagtggtgt gatctcagct cactgcaacc tctgcctccc    56400
cggttcaagc aattcttgaa ttcctccctc agcttcctaa gtagctggga ttacaggtgc    56460
ccgccgctat gcctggctaa tttttttttt ttttttttt ttgtattttt agtagaaact     56520
gtgtttcact atgttggcca ggctggtttc gaactcctga cctcaagtga cctgctcgcc    56580
ttggccttcc aaagagtgct aggattatag gcgtgagcca ccacgcctgt cctattatta    56640
ttttttaatt gacatgggga cttactgtgt tccccaggct ggtcttgaac tcctggactc    56700
aaaagtcctg ggattacagg catgagccac tgtgcccagc caaaaataaa ctattttttct   56760 tttatacaaa tagtatgtgg tctttgtgtt agaagtcact gaaaaataga gaaaggaaaa    56820
accttgatat attcaaagac aatagcatta ttttgtttcc ccccaatata cttttattta    56880
cattgttctt ttttttttt tgtattgagg ccatactgta gatgtaattt tatatccagg     56940
tttcaaaatt tcatattcta gtcctaatgt ttactcattc tgttaaaatt ccgaagacaa    57000
gtatcctttt atttatttat ttatttattt attttgagac agagtctcac tctgttaccc    57060
caggctggcg tgcagtggca cgatctcagc tcactgcaac ctccgccccc tgggctcaag    57120
tgattctcct gtctcagctt cccgagtagg tgggatttca ggcatgcacc accacacccg    57180
gctaattttt gtgtttttatt tatttatta ttttgagac agagtctcac tctgttaccc     57240
```

```
aggctggagt gcagtagcgt gatcttggct gactgcaacc tccgcctccc aggtcaaagt    57300
gattctcatg tctcagcctc ccaagtagct gggcttacag gcatgcgcca ccacgcccgg    57360 ctaattttg  tatttagta  gagatgtggt  ttcaccatat tggccaggct ggtctcgaac    57420
tcctgacctc aggtgatcca cctgcttcag cctcccaaag tgctgggatt acaggcgtga    57480
gccaccgtgc ctggccaagc atcctttag  agagtggcgt aatgtatcat gagtgtgtct    57540
cccctgttgt tcttatcact cctgtgttgt tggctagcac tcgttctgg  ttttagttcc    57600 tgtcctagtc agagctccat gatgctttct gctctgctcc taatgttctc tgagtccctc    57660
tgaacctgag ttgaatggtt gaatgtgttt ttgaaattaa gcagcttgta tgcagtgcaa    57720
gtacttcttg ggttttgtac atctaagccc agcctgccat tttggagagc actttagtgg    57780
taaaatgatt cgaaacaggc tttctccctc cctgtgtgta ggccaccagc cagacagatc    57840
tagaaaactg ggtcactgct gtacactctg cttgtgcatc ccttttgca  aagaagcatg    57900 ggaaagagga cacgctgcgg ctgctgaaga accagaccaa aaacctgctt cagaagatag    57960
acatggacag caagatgaag aagatggcag agctgcagct gtccgtggtg agcgacccaa    58020
agaacaggaa agccatagag aaccaggtac tgtttgtcta cacctgagtt ttcttccatt    58080
gctcatgtca cttgtgcagt gactgaacgc atgctgtcat cttggtggta tttcttggct    58140
cacatcttgg tggtatttct tacaccctgg gggaaataat ttctgtggtt tttcatttta    58200
ggtacctaat gtttgccatt ttgtgacatg ggtgatatga tatgctttat gacctttggc    58260
ggctctatgt atatactgaa atattttgtg acccaaactt aattcctaat ttgaatagtg    58320
ccttctggcc ttgatgattc actcatatat tgtcattttc tgaacaaaat ccatacaata    58380
aaaccactag aagattagac aggtaagatt ctaatacaat agctttggaa aacgtggttt    58440
ggtgtaacag ctgtttctgt gtctatggat tgcaaaaaaa cagtaatttt tctggttata    58500
acagagaagc acgtaacgaa atgctttctt ttctctgctg cggttccata ttcatataat    58560
aaatggctgc ttcctatggc atttgcattt tagagaaggg aaaacagttt gaaaattttt    58620
atttcccttt gctcagacaa cctaaacact tagacaagtg ttagtggaat ttcgagcatc    58680
cctatcttag tcaggtttcc taggagacag actttgatag tgatttagat gtaaaaagtt    58740
ttactgggaa tgctctcagg gacaacgcca gcctggagtg agggagcagg atctgggagg    58800
gacaagttgc attgtgatgc agcttgtccc acagcgagct gtggagctgg gagggccatt    58860
cagagctctg catggaggca gggtggccgg ccttcgtccc ctcaggccag cagggcaagg    58920
cagctcccct caatagaggt gagttaccac gaggggatct gtgtgtgagc tgggaaaagg    58980
aaagcaatgc ctctgtcttg aaggggaat  ccgggtgatt cactatagaa tccactacag    59040 cccctccaa  aaccagttgt caaatgacct gggaacttga atgaggaatg ggatgaagat    59100
agatagtgag caggttcttg cattttct   cctttagtta cttgttaagt tattacagag    59160
aaaccagttt cttaggaaa  aaaaatttca tggtaacaca acaatttaga catagtgtga    59220
cttattagaa aggaattta  catgtggtgt tttatttaaa ttgcaaatta ataatacct    59280 ctgtttatgt ctgaatgttt aaccttgttt ggaagttttt tcatctgtgt atatatgaag    59340
aattcagcat gaggctgggc atggtggctg acgcctataa tcccggcgct tgggaggcc    59400 gaggtgggca gatcacctga ggtcaggagt ttgagaccag cctggccaac gtggtgaaac    59460
cccatctcta ctaaaaatac aaaaattatc tgggcacggt ggtgggcgcc tgtaattcca    59520
gctactctgg aagctgaggc aggagaatcg cttgaacctg ggaggcagag gttgcagtga    59580
accaagattg tgcactgcac tctagcctgg gggaagagtg agactctgta taaaaaaaaa    59640
```

```
aaaagaattc agcatgagta ggaaaaaatt tctgtctaaa aataggaaac tgattaaagg    59700
catgcattca atgatacacc gagaatttgg aataatgtat caattggcaa tagcaaaata    59760
accaaataat tccgacctct gcccctcatt aatcttctca ctctatctac ctttgcttct    59820
ccttttctca tatctcatgt tgcctttctc ccatctcagc tctttccctc ctgcttattt    59880
tcccatctgc aaatactggt gtacctaata gatgcacctg gcttaaagaa ataaaaataa    59940
ttgtaaaata tggaccccgt ttctaagaaa ttataattta gttagagagc aagccttatg    60000
aacatgaaac taaaggtcat tctaaaatga tcgaagttag gtgacagctg gtatagtcat    60060
caaatattat gggagatcag agggttgagg ttgtactgtg atcttgagga aatgaagact    60120
tcctggaaga atatggtgtt aaaaagttgt taagaggtgt gaaggatttc caggctggaa    60180
gggtgttggg cgagcatgga gagacaattg gaagtgactg agtggtggct tggggctctg    60240
gagcacactg gagtcaaagg tttgggaagt gacaagagtt ggcagttagg ttggataggc    60300
aatgaagctt tttcagtctg tgtcttagtc tggaacaaaa tactgtaaag cgggtggctt    60360
ataaacaaga gcaatttatt tctcagagtt ctgaaggctg agaagtccaa gatcaagatg    60420
ccggcagatt cagtgtctgg tgaggccctg ctttctggtt tctagaagca tcttcttaac    60480
tgtattctag catgacatga ggagcgaggg atctttccgg gccgcgtttt ataaggccat    60540
ccatcctatt cacgagggct caccattatg actgtcgtgc gcagtggatt aagcagtgaa    60600
ggatgaaaga caccgtaact taatgcttga atcacacagt ttgttggcac gcaaacagtt    60660
cttaacagat attggtattt tatccccatt cacgctacac acaactcttg ttttcacccc    60720
tgttaggaac aagtcgggga tcttacatga ataggcacag gattggtcac agaagtcctc    60780
aggcatctgg gaatagcttc ccctggtatc aaggctggaa tgttgaggct gaagcattca    60840
gtcaaggaga tggcaagcct gactccgggt ccctttctga gtggcagcat ctcatcctca    60900
cgagtctgtg tctcagcaga gcaggtcgag ctgcctgagg gcttctcttt ttatagtccc    60960 tgtttggga tccacctgtg tctggttatc ttgaaggttg gtgcgcccta gcatgtgatg    61020
tcgtctcaaa ttggaatatc ccaatgcagt tggtctaaac agatttgggc attctggcag    61080
acatctgcac ttacaaacta actgtgataa catatttaca ctatacccat aaattgcact    61140
ccaaacaatg acctaatcat tgccccttt aaaaaggccc cacttcctaa taccatcacc    61200
taaagcatta agatttcaac gtacatattt cggagggaca cattcagccc atagtggtct    61260
tgtatgcaag gctcagatgg taaggtttat tttatactct gctttcaggt gggggatac     61320 aggtttttaa gctgaggaca aagcatgatg actgtagtgt ctttgaaaga ttaatcaggc    61380
agcagcttgg aggacagagt ggggcaaaag tgtcaggca gtggagtggc actgtgctgg     61440
gtgtatagat acaagggcct ggtcccaagt gacacaagtt caacagttta catgaaaat     61500 gtataacagg gtacataatt ttctgtaatt ctatagaatc tttttttttt ctttttttt     61560 cttttttttt tttgagacag agttttgctc ttgatgccca ggctggattg caatggtgtg    61620
atcttggctc atcttaacct ccacctccca ggttcaagcg attcccatgc gtcagcctcc    61680
tgagtagctg ggattacagg cgcccgccac cacgcccggc taattttgta ttttaatag     61740 agacggggtt tcaccatgtt ggtcaggctg gtctcgaact ctgaccttag gtgatccgct    61800
tgcctcagcc tcccaaagtg ctgggattac aggtgtaagc caccgcgct aatctcaatt     61860 ttttagaatc ttaaagacag taacttacac ccctgagcgg aactgttgct caaccaggat    61920
atgccattta aactcaaaag tacaaaatag ttttaacgag gaagccaaaa ctgccaagaa    61980
gaatgcagga ggtggaaggc tttgggatcc aacaagaaca cagctgctga cattgctgag    62040
```

```
ggagagctgc ccccacgagc ccagcttgcc tcctctcagg ccctgcctgc ccctcttaag   62100
gggcctcacc ctgctcacag ccaggggggcg ttcagctccc gaggcagtgc agccgtacct   62160
ccccgctctc tgtctgtgtg aatgtaggt tgggagtcca tgtggaggtg atgggacaga   62220
tcaaagagcc tgaaggagac acggttatcc cagagttttc tttgtaccat gtctcatcca   62280
tggtgctgat tttccaggat ccggcagcca cagcctgtct atcctgagat gagacttgtg   62340
gatccgagtg tctcagagtg ttcagagcac cccagtcaaa aatctcatcc tgaccataat   62400
cgtagtcgaa gggatgccca gcttggagtt ttcaggtctt tgggtagggt cagatgttta   62460
gggctaggga gagaaaaggg acatttggca acactgagag gctcctggcc tgttgtgtgt   62520
gtgtggtggt ggtgggtggg ggtttctctg tggccacaag gagtctaagc agacattttt   62580
ttaaaaattt aaatttgcat taaatgtaat tgtattccct tgtccatagt ttgtaaatgt   62640
ttaattgatg acatcatagt tggtgctatt ctctgattaa gaggggaggt tacttgaaca   62700 taaacccttaa cataaatcca ggggtctgga tggtcaggtg gcctgaagag aaactgtttt   62760
aaagaatgag ggtaattatc acttgtggtc cattatccat tctttgacag aatcatcact   62820
ttagttattt taagtgcacc tttctaatgc tactaatttt tcatttttgg ttctcccctc   62880
cccatagccc aggccctaac cccttcctgt gtcctcccca cactcccttc tccctacac   62940 ccttctccca acccctgccg tacatgcact ccctttctca tgttagtctt gtgagtttct   63000
ggtaacagac aattgggatt gattttagaa attcttgtcc aggcacggtg actcacacct   63060
gtaatcccag tactttggga ggctgaggct ggaggttcat tgaggccag gagctcaaga   63120 tcaggtgggg caacacagca agaccctatt tctgaaaaag aaaaaaaaaa gaaattctac   63180
ctggaagtat tctcctcacc gtattgcact ctttgaggtt atgatttagt cacatgttcc   63240
tgaagggctt tgtagtgtgt agcctgagtt atgtttgctg tgcccgctgt ccttgcatcc   63300
tttgtcagca ggttgtaaag gagctgttta cgctttttt tttttttttt tttgacagag   63360
tcttgctctg tcacccaggc tggagggtag tggcgcaatc tcagctcact gcaacctcca   63420
cctgctggat tcaagcaatt ctcctgcctc aacctcccga gtagctggga ttacaggcac   63480
ccaccactac gcccagctaa ttttttgtatt tttagtagag atggggtttc accatgttga   63540
ccaggctgtt ctcaaactcc tgacctcagg tgatctgcct gcctcgacct cccaaactgg   63600
tgggattaca ggcgtgaaac cactatacct ggccaagagc tgtttacttt ttaccttcag   63660
acacaaagac tgggaagcat taagcaggaa caagtacttg cttaaaattg cttttatgag   63720
atatttgaca aaaaaatgta atgtgaagcc acaaaggcaa aggtatttac agatcaagac   63780
caatcaggac agggtctcca aaatattccc taagcattta gctttctcta aacttccttt   63840
taaaaatatc tgtaaaagag cagtgcttta tccacttagc attttaaaac ctcaataaat   63900
atacatttat ttatgtagct tcctccccag cggttttccc tgaaaacctc agatgtagtc   63960
atttctagcc taaaaataga atgtgcaatg taggtgacat catgcaacag aaattctctg   64020
gaacaggttt tcttcgaagt acgtgggtgg agaagatcct ttttgaaata aaaaggcact   64080
atcgcagttg taacataccg gctgagctac atacggtcag tggtgacatg ctctggccgt   64140
gtcctgggcc tcttgggtgt ttctggggca ggatgatgca gctttcattt gagcatgtcc   64200
aatgtggacc agatcacacc gccatccaca cgccagatcg cctttgaagt tcccaggag   64260 gaagagttgt aaattaagtc cagttagtac tttatttgcc tttctgctta ttatttcaaa   64320
caagtaaaca aggacaaaac ctcaccaccc ttaggcagtc ttggcattct cccagatggc   64380
atcccccatc ctgcctcatt atgtgcgatt tccagggtag acaggcctgc ttctgtggtt   64440
```

```
aattaggctg gggagggagg aggtggttgg actaccaggg gttgctgtgg ggaaggagga    64500
agcacttgct ggtagggttc agactgctct gggttttatg aaatgtgggc ttcagtttaa    64560
atatttactt aaatacagtt ttaaaatcat aaagaggacg gattgcgttt ggacaattgg    64620
caactggtga agagaacaat gagaacaagg ctttgaggaa aatacgagga tactgtggtg    64680
tatttctgga tgtgtacagg gggaagcagt ttgaggaaca aaccactgga gtgtagcata    64740
tttgtgaggg gatttgaggg agataaagtc agattgtgga ggtggtgggt gaagatgtga    64800
actttattca ataggcaata gggagatggt gaaagtgtta tttttattt tttattttt    64860 aaggcaggca atagggagat ggtgaaagtg ttattttta tttttaagg cagagtcttg    64920 ctgtgttgcc caggctggag tgcagtggca tggtcttggc tcactgcaac ctctgcctcc    64980
tgagttcaag tgattctcgt ccctcagcct cccaggcagc tgcgattaca ggcatgtgcc    65040
actacgtcct ggtaattttt gtattttagt agagatggga ttggccatgc tggtctcaaa    65100
ctcctgacct caactgatcc gcctgcctca gcctcccaaa gtgctgggat tacaggtgtg    65160
agccagtgtg cccagctgga agtgttttta ttttctattt ttttgaaacg gagtctttct    65220
ctgtcgccca ggctgaatg cagtggtgtg atctcggctc actgtagcct ctgcctccag    65280
ggttccagtg attctcctgc cttagcctcc tgggtagctg ggattacagg cgtacgccac    65340
cacacccggc aaattttgt attttttgta gagacgggt tttgccatgt tggccaggct    65400
ggtctcgaac tcctgacttc aggcaatctg cccgccttgg cctcccaaag tgttgggatt    65460
acaggcatga gccaccgctc ccagcctgga aatgttttg ttaggagaat aagaatgttt    65520
ggtttagtta aatgagcgtt tgttcggtgc atactctggg tcaggcaaat gtgcacagac    65580
tggagactca aagaagtcac tgtctctgcc ctcagtgaca gtggcactgc tagagagagt    65640
gctagagcct tcagtgacag tggcacctgc tagagagagg tgacagacag ttgagctctc    65700
agtctagcag gtgacagaca gttgagcata caatttcaac ataacacagt gattcagtgc    65760
acgtggcatt ccagtgctgt ggaagacaga aatgggaaat atagcctcat gtgcagtcat    65820
ggaagaccct ggaggaggga ggccaagttg cttcttgaaa aatgaggagt ttaccgggag    65880
aatagagagg ggtcttccag gccaaggcac agtgggagca aatgcagtgt ggttttaggt    65940
aggtggtgag aggtagacag gggaagtagg actgtctgtc actctctcct cccggtacca    66000
ctgcagaagc ctccggtttc gcccttcgtc tgatgcatct tccatacaac agccagactg    66060
ggttgcatcg gaaaagcaca tctgggtcag gtgcagtggc tcatgcctgt aatcccagca    66120
ttttgggagg ccaaggtggg cggatcactt gaggtcagga gttcaagact agcctggcca    66180
atgtggtgaa accccgtctc tactaaaaat acaaaaataa ttagccaggt gtcgtggcgc    66240
atacctgtaa tccagctac tcgggaggct gaggcaggag aatcgcttga acccaggaag    66300
cagaggtttc catgagctga gatcacacca ttgcactcca gcctgggcaa cagagtgata    66360
tgtctcaaaa taaataaata aataaataaa gtaaaaaaat aaaaagcaca tgtgatcctg    66420
tgattgccag ataaagtccc tgataacctc tccccacctt gacctttatc tgcaactccc    66480
tgagcccacc cttctgctcc tttctttggg ttttcctca ggcagagagg actcctgtgc    66540
tgtgcacaaa tgtgccctgc tcccctccgc cctcttcatc tggctcaccc cttctcgact    66600
gtcatgaagg gtttagggt cgcttcctcc aaggcgctgt ccttgatcgc cttttgccc    66660 actccatcag ggagcccac tctcctccca cagttctcca tgtctgtgcc actgctgtca    66720
tccatggctt tgtcatgatt tcttcgtgtg taaggttgct cctgctataa aatacgtgct    66780
cctggaggaa ccgtgtctgt ttttttatct ctgaaccctc gatgccttgc ttgagttagt    66840
```

-continued

```
gaatgtgtgg aagcacctct gtctcgtctg tccagggatg ctgtcctctg tactgcagga    66900
aacagagatc ttctctgagt cagccaccac cccacttccc agtgttccag gccttcctgc    66960 ttcaccccg tctaacagaa cgcctccttt tgccctgcct tgttctcatg ctccccttcc     67020
ttgttttatc agagcctctg ccttaggcca ctatcatatg tgatttcaca ataactctgc    67080
aaggtaaaga tgtagatata gcacccgttt gttggatgag taaatagacc cttaggagaa    67140
gtatatttct tttcttttc tttcttttt tttttagaa ttaaaatttt ttttaaaaaa       67200
tagagacgag gtctcgctat gttgcccagg ttggtctcga actcctgggt gcaagcgatc    67260
ctcctgtctc ggcctctcaa agtgctggga ttataggagt gagccactgc acccagacga    67320
gaagtacatt ttccgtataa gtaccgtgca ctaactgatt gcgccactgg agcaccaaga    67380
agtgcatttg ctaatgtcac acagctgtaa agtggtagag ctgggatttg gacacaaatc    67440
tttgctccta attcataggc gctactgctc cgtaagactt gggtaaatca gatggtgctt    67500
tgcttgctaa ctaaaccagg tgatgaattg ttttgtgtgg aatagaatcc ttgatttact    67560
tgtttttata acttggatt ttcaggtcga tttgatggga attacattga ttataaaact    67620
gagtgaattt tgggtatgg gaattatatc tcaaaggaaa acagaacaaa accgaatctc     67680
tctactttag ctggttgttc taaatactgt taaacttgag tgtcatctat gtcactagct    67740
ggttcttctg tgaagatagg ttttagtatt tggaaagcat ggaacgggag tttttcagct    67800
tcttacacca agaaagaaac atgaattatc ttatgggaca aacctagtaa taggcaaatg    67860
actactgcga ttaaatgact aaatggcaga aaatatttt ctaggactgc tgggtgtggc    67920
aggaatgtac ttgtcatctt ttaaaaaaaa atcattattc atttgttatt tttagcatta    67980
ggcttcatcc ctctccctcc cactttacta caggagacca taacctttct gagttcatta    68040
aatcagtaaa gctgtgttag caataaagag gaaaattttg cattgaattt gtgccaatgt    68100
ttaaaaatgg gagtgttccc ctgtaatttt gttattagta acttcctttc acaatgaaag    68160
ataatgaaaa ccttctcaga gtgagttttt ttcagtcttg tctttttat gttttgagca     68220 tgggcattaa aagaaacaaa agctcaatct atatagaagt tatgttttt acttttttt      68280 ttttgacagg gtctcactct gttgcccagg ctggagtgtg cagtggccct gtctcggctc    68340
actgcagcct caacctcctg ggctcaagct atcctcccac ctctgcctcc cacatagatg    68400
gggctacagg tgtgcaccaa ccacacctgg ctgagttttg tgttttttta tagagacggg    68460
gtttcaccac gttgaccagg ctgcaagtgt ttttttttt cttttatat catatcttga      68520 tgtttatctt taaataataa ggaaacatct agaaacttat cagtatttaa agaatttagg    68580
aaaagggggt gggatgtctt ggattaaaag gaactgattt taggcattct agttttgat     68640 gttagaaaaa aatatctcca gaaacacctt gataaatgtg gtcaggtaat acattactat    68700
tttggtgatt attatcattg aactgtactg aatctctaaa ctaacataca taatagctaa    68760
aagattgtct ttttccctt tacccttaa aatatgtatc tttgtctttc ttttatgtca      68820
ccttctgaag aattgttata aaatgttttt ctttcaagtt aacattactt taaatttggg    68880
ctggctttga atgtcaaggc tggtaggata ttgaaatgta aagtgttcaa tatgaatagg    68940
gccactgagt gagagtgtgg tagtcttacc tccttctctg tagaatacct ggggtatat     69000 gggcagacat aaagtggaca ggtaaaaatg taaatgaaag ttgctaaggt cactatgagg    69060
atagtgcaca ggtatcttcc tatgagtcag aagacctggg aatcaggggc cccgttatag    69120
ctacttgaga gggtccctgt cccctacatg ttgttcacat cagaatcggc tttgggtctg    69180
ctagtctggt agggtgagct ttttacatga ctggtcaaat tgcttctctt ctggacttaa    69240
```

```
gtctcaactg ctgagaaatg aaggtatggt aataccaagt cccttgcaat tcattgtga   69300 atgttaacag cctttctaaa tactataagg tctgttgtga gcctttgggt ccagcacttg   69360
tacctcttct tccctctaag gaacccgagc ttctgaatca ggggcctcac cgtactttta   69420
cttgaatact ctttcaagtt cctctctaca actttgctga gtctgtggaa agaaaagtca   69480
aatatttcat attgattatt taaccacaga tcttcattta agctctggaa ctgattcttt   69540
ctataaagaa ccatgacctt aaaaataaga tgactatgat ctttcaatat ggaatagata   69600
cgtgagtaaa gatggcttac tctgccacaa agatctatag ggatgaaggc tgtatataag   69660 tcagggggtct ccagagaaac agaaacagta ggatgtgtgt atacctgaag aggtgtgtgt   69720
gtatgtgttt gtgtagggag agaatgagag aaatttatta taagaaatag gctcatgcag   69780
ttatggagaa gagcaagtcc caagatctgc agggtaagtc agtaagctgg agacctggga   69840
gagacaatgg tatagttcca gtctgagtct aaggcatgag aatgaagaca gctgatggtg   69900
tagttctagg ctgaagactg gtaggctcaa gattgaggaa gagcccatgt tttgttcaag   69960
tccaaagcca aggggaaaa aaagccagtg tcccagtttg aaggctgtca ggcaggagga   70020
gttctctctt acttgagggg gtgtcagcct ttttgtcctc ttcaggtggt caacagattg   70080
gatgaggccc acccacatta gggaaggcaa tccgcattac tcagtctacc catttaaatg   70140
ttaatatctc ccagaacatc cttggagaca caccccagaat aatgtttgac taaatacctg   70200
gtcaccccgt ggcccaatca agttggtaca taatattaac cattacgcgg gtggatcgct   70260
ttgaactcag gagtttgaga ccagcctggg caacatagta aaaccctgtc tctacaaaaa   70320
aaatgcaaaa attagccaag catggtggca tgcacttgtg gtcttgagag gctgagttgg   70380
gaggatcact tgagcgcagg aagcagaggt tgcagtgagc caacaatgta ccactgcatc   70440
cccagctggg gtatcagagt gagaccatgt ctcaaaacaa aaacaaaaac aaacaaacaa   70500
acaaaaaatc actccagtca ggataaggtt aagaaggata aggaacattg ttgaaataga   70560
gaagtcataa ggttactttt cctttgcatt ttctactaaa ttaaattta aatgaacttt   70620 acagtgtaca gtttattgag atactggttg tcttgaaact taataagata caatcaagac   70680
aacaaacgtc ttgattttta taaggtctcc ttttgggctat tggggtgtcc cagcccctgtt   70740 gactttccaa caaacctaag catctgggtc catgttctcc ctctgaattc acctgtattt   70800
tgtcccaaga tttgggtgga gaggtctatg agtgctgaag attattaaag tgtttctgat   70860
aaaactttat gattccctgt gtatccctgt gtgctcattc ccgatctgag ccggggtatc   70920
gggtctcact ctgataaccc cagctgggga tgcagtggca cattgttggc tcactgcaac   70980
ctctgcttcc tgtgctcaag tgatcctccc aactcagcct ctcaagacca caagtgcatg   71040
ccaccatgct tggctaattt ttgcattttt ttgtagagac agggtttcac catgttgccc   71100
aggctggtct caaactgtct ttacctctca gtactgcttt gatgtgtagt cacataagta   71160
cattaaatag tgctgttaaa aatactttta aaactacagg attcagtgca aatacaagag   71220
attgtcttct tccccaacct gtggtgattg gcatagacct gaattttatt ttattttgtc   71280
tttttttttt tttttctgag atggagtctc actctgttgc ccaggctgga gtgcagtggt   71340
gcgatctcag ctcactgcag cctccacctc cggggttcaa gcaattctcc tgcctcagct   71400
tcctgagtag ctgggattac aggcgtgtgc caccacacct ggctaatgtt ttttttttt   71460 tgtattttta gtagagatgg ggtttcacca tgttggtcag ctggtcttg aactcctgac   71520 ctccaatgat ctgcccgcat cggcctcccg aagtgctggg attacagacg tgagccatca   71580
ctcccggcct ttttgtctt tttaatccac catggattgc atgggcatct ttaccttctg   71640
```

```
gtatccagtg actcattcat tttctttttc tttccttttt ttcttttttgg agacagtctc   71700 gctctgtcac ccaggctgga ctgcaatggc gtgatctcaa ttcactgcag cctccacctc   71760
ttgggttcaa gagatcctcc cacctcagcc tctcaagtag ctgggactac aggcatgcac   71820
caccatgcct ggctaatttc tgtattttt gtagagacag gatttcgcca tgttgcccag   71880
gctggtctca aactcctggg ctcaagcagt ctgcccacct cggcctctcc aagtgctggg   71940
attacaggca tgagccactg tgccttgccg actcattcat tttctttcct cttatatctt   72000
caccctccat acaaccttca gaaaatatct gataaactgt tttacagtga ggcataaatg   72060
agtgtgataa actttaatgc attatccaat ctagaaatat ctacatatta ttagaagaca   72120
aaggaatcca tctataattg tggactttca ggaatcatct ggagagaaga tgtttgggaa   72180
acagaactga gatgatagtt tttactgaac cttaagtaag gtgtcagttt gtgcccatcc   72240
atcactctga aatctggaat tctctaatat ggcaggacca ggaagagact tgcagtttca   72300
atttgaactg tcttgttagc gtagaacagg agtcatcagt aataaggcca tgcaccagaa   72360
tcccagaagg tgctcatgaa atgtaaactt tcctaggcct cagacctaat ggataaaatc   72420
ttcaggcgta ggacctgggc atctgcattt ttaaaagcca acaggtcatt ctgtccattc   72480
aaggctgata ccagtaggcc accacgttgc taatagggt atacaggatc ttgagtgagg   72540
ttaaattctt tatggatgtt gacattgttt caatgcacct tggaatgtca ctgttttgct   72600
gacaaatgat gatgattaag aaattctttg tttagatctt gtgactgttt ttctttcatg   72660
cagaaaagtt gtgcagcgac caacctaaga aatagctaca gagaacttgg aaaaggtctg   72720
gggaatgccc agaatttgta atacttgtct atggggagag actggagggg gcagagtgtc   72780
cagtgttgga aatccttcaa agtattattt atccagaatg aaggattcac ctagaaagct   72840
tggtgtgaaa ggctaggatc tgtctgggtg ctcagcaaca tggcagaact agagatgcaa   72900
ctggtgcacc tgaaataacc taactcttca cactgcatcc ttgattacaa gcgttcactt   72960
acagaccttc tcttgagtgt tgagattgcg ctcaacagct tttgaatcac agctttctgt   73020
tcttctcgtt cttctgctga gtccctgtgt tggcaagtca caagagcctc tcttcaccta   73080
ttattaataa cttatctttg catgaaggta atacttgtag gtaatgcatt ttatatcttt   73140
gggagaaagg agagtggctc ccagagtttg gctgcatttc tttaccaact catgacttaa   73200
gttttgaaga agttcatagt aacttctgtg gtgtaaacag ctgcatatac tttaatttta   73260
tttagatgta cagatggcag ttattctcca agatacttac ttaggagtat actcagtaaa   73320
attctatttg tccttatccc tgaagtccat ttgcttctta ttgttttgag tcatttactc   73380
agaatgaaca gaaacataaa gtcattgctt ttatttatct ggcatctgtt tgtgtgcagt   73440
tcagttaatc cagtttagga tcagggactg taaatgtgaa gggaaatgaa gcaaagtgaa   73500
aaagctgact tgcaaattgc atcctgtttt aagtcaggat ggtttagagt gttggcattc   73560
tccaaacaaa catcatgcct ttttggcatg tcactgtatt gggaccacca gcttttgtt   73620 tttgttttg tttggctatc ctgatgaaat gaagtgctgg atgacccagt gcattttgtt   73680 tttttttg agacggagtc ttgcttggtt gcccaggctg gagtgcagtg gcatgatctt   73740
ggctcactgc aacctccgcc ttctaggttt aatccattct cctgcctcag cctccagagt   73800
agctgagatt acaggtgcct ggcaccacac cagctaattt ttgtgttttt tttttttctt   73860 tttttagta gagatggagt ttcactgtgt tggtcaggct ggtctcaaat gcctgacctt   73920
cagtgatctg cctgcctcgc tttccaaagg acccaatgca ttttgatggg agggattgag   73980
atggggtgag caggaaaggc taatttaaac catgcagacc agccgaaact aatttttct   74040
```

-continued

```
tcaagtttgt gaaagggatc acattttcgt tttaacctgt gaaaacttttt aattttttatt   74100
taaatcacct ctgttttttgc tttaagatcc agcaatggga gcagaatctt gagaaatttc   74160
acatggatct gttcaggatg cgctgctatc tggccagcct acaaggtggg gagttaccga   74220
acccaaagag tctccttgca gccgccagcc gcccctccaa gctggccctc ggcaggctgg   74280
gcatcttgtc tgtttcctct ttccatgctc tggtaagttc ctgaggaagg ctgtttctgc   74340
agcattcggg gagggctgcg gatgctcccc cttctcttcag cttgttgcca tcggcacttg   74400
tggggcttga cccaacaact gacacctaga ggccaggtca cccagaggcc aggggcctgg   74460
agatgaagga gaccagacgt cgtgctgtag agccccccggt ttctctactg cttattctag   74520
agtccagcag ctagtggaca gttactgcat gctcatctct gcctttctgt gtattccacc   74580
atcaggaaag tgggatcctg gagaagggggc aacagtggtg tgaagattaa aggatggatt   74640
aaaggttgtt ttctctgtcc tgcagagcgc cccatcaggt tttttgaagt cgtacccatt   74700
ttggtggctt ctgtgtgttg tgttggctca gcctaggggg ctgtagtggt tttgctgacg   74760
ctgctgccca ccatggagag agctgactgt catgacttgt gttatccaga tgagagtggt   74820
ctatatgatg gatgctttcc tggtatttca gacatgcagg agcttttggc gatagtcaga   74880
atgcatttat agcaagcaga gctcacttcc ttcattttttt ctgccactca aatactaagc   74940
ctttagattt ttttttaaact gtgttttaca ttaggtatgt tctagagatg actctgctct   75000
ccggaaaagg acactgtcac tgacccagcg agggagaaac aagaagggaa tattttcttc   75060
gttaaaaggg ctggacacac tggccagaaa aggcaaggag aagagacctt ctataactca   75120
ggtgagcttt tcagcatggg aacagcagac tagagtgaaa ttcctgaaac ccctaattttt   75180
cggcctgcta tgaatcatca atgttcattc tctgttaaga atgaaatgag gcgaggtggg   75240
gtggctcacg cctgtaattc tagcacactg ggagggcaag gcaggagggc cacctgagcc   75300
caggacttca agaccagcct gggcaacaga gtgagacccc atctctacaa atagccgagt   75360
gtggtggtgt gcgcctatag tcccagctac tcggaagct gaattgggaa gatcgcttga   75420
gcccgggagg ttgaagctgc agtgagccat gattttgcca ctgtactcca gcctgagtga   75480
cagagcgaga ccccgtctca aaaataaaaa tgaaaataaa agttgattca aaggaatcaa   75540
ctcttagcat gcactttttt ttttaaccca acgaaactgc acaagttgcc gtatctatcc   75600
cggcaccct gaagaggtag tcacactgcg tgcagtgctt aagaacagaa aaataagaa   75660
taatcagaaa ataatccaca cttttccttc cctctagtac taatatttac tttctcatag   75720
atttttatatt aaaataaatg gaaaattaat aatcagagga gtggcagctc agttctgttg   75780
atagagctgt ggattttgct cactaaatcc ttagaacatg gccttggggt tttgtcatcc   75840
cattttagag acgagcagac tgacacttga agaggttacg tcacttacct tatcctgttc   75900
accagcacca aagggcaggg ccaggactag tttctgccta agtccacggt cttgaaacac   75960
tggaaaattg ctagtgctta ttttcccttg gggaaaggtg actcttgcaa cactttcttt   76020
ttcttttcttt ctctttttttt ttttctttt tttgagatgg agtcttgctc tgtcacccag   76080
gctgaaatgt agtggtgtga tcttggctcg ccgcaacctc tgcctcctgg gttcaagtga   76140
ttatcctgcc tcagcctcct gagtagctgg gactataggt gcacaccacc atgcctggct   76200
aatttgtgta ttttttagtag agacagggtt tcacctgttg gccaggctgg ttgtgaactc   76260
ctgacctcag gtgatccacc cacctgggcc tcccagagtg ctgattacag gcgtgagcca   76320
ccgtgcctgg cctcttctaa catttttatt aaggaaaaat agtctaagca catgttatgt   76380
gaaatgtggc ccaagtatcg taaattgttt tcaaaacatt ttgaatatgt gtatttcatg   76440
```

```
gtgcacctgt atttcatgat gcaggtgcat gataatggac tttatcttgc tgattgatat   76500
gttttaggat tattctgttt caaagctgtt gaaaaaataa gttatgatga gacctgatca   76560
ttcaggtgaa tagggaaatt gtttgcaatt aaatctgaag aagttttgc ttttattttc    76620 aatgagctgc tgttttctg attatatttt caatatcatt ggaaagagag tcacatttta    76680
ttggatcttt gttttctaat ttgtatatgg ctatttgata acgcttttgt gaattgggta   76740
agtaaaaggg ccagtatcag ttcctttgac ttgtttaaaa ccttaaaaca ataaagttag   76800
aggtggtgga gagtgggttg gtagattaac agacagcaga atcacaggaa acttttctta   76860
tgtggccacc atgtttatat actcatatac aaaaataata tcagatttta aaattgtggt   76920
tctacttgta attaatttt ttttcttttt tgagacagag agtctctctg tcactcaggc    76980
tggagtgcag tggcacgatc ttggctcact gcaacctcca catcctgggt tcaagcaatt   77040
ctcgtgcctc agcctcccaa gtagctggga ctacaggctt gagccaccac acgtggctaa   77100 ttttatatt tttagtagag acaggggtttc accatgttgg ccaggctggt ctcaaacttc    77160
tgggctcatg tgatccacct gcctctatct cccaaagtac tgggattaca ggtgtgagcc   77220
actgtgacca gcctgtaatt taatttaatt taattgtaaa gagtaatctt atttgttggt   77280
tgtaatggaa atgtatttcc tcattattga ctgtagtcaa ctgcaaaccc tttgctaatg   77340
gtgggcctat gctttcttta ttttttaaaa attgttttg tagaaatggg gatgggagtg     77400
gtctccctat gttgcccagg ctagtctcaa atttctggcc tcaatccatc ttcccacctc   77460
aacctcccaa gtcctggga ttacaggtct gagccataac accgagcact tatgttttgt    77520
gaactgaact tctttgatgg ttaactaatg tccttaaggt attttaatca agacagtata   77580
ttcgatataa ataataactt gataaataac ttgcttattt tttcttaggt gtagacattc   77640
tgctaattag atatgagcct aatatggttt ttacccagca tctgtggtaa tttgttctca   77700
acatagactt tttgataaac aaaagcattt ggtcgaacat ttttgtttt aaaaagatat    77760 gaaactaatt acagtgtcag tatttatata actgaatgaa gttgatttag taggtatttc   77820
taagtgttta tattgttttt aatgttaatt atgccattac aaaatttaga aggtgaaatt   77880
tggaaaaggc aattgttttt aattcttcta cccaaacaaa ccactttaa catttagcta    77940 tattttcttc caagatttat tctgtgcaca ttaaaaaaag taggtatgag cttgattttg   78000
ttggttctgt ttcacacctt cagaaacatg tacttttgg ttaaaagcat atcaagaatg    78060
aatttattta tttatttat tatttattg atacagtctc gtgctgttgc ccaggctgca     78120
gtgcagtggc atgatctcag ctcactgcac cctccgcctc cgggttcaa gtgattctct    78180 gcctcagcct cctgagtagc tgggaccaca ggcgggtgcc accacatctg gctaattttt   78240 gtattttaa tggagatgag gtttcactct tttggccagg ctggtcttga actcctgacc    78300
tcaggtgatc tacccacctc agcctcccaa gtgctgggga ttacaggccg acttaaataa   78360
tagatgacat aaaaagtaa aacgtaacta tgcgggaaat aaaaacttta agtgtattag     78420
aataatgata caaattgtga tatgaagctc ttctaaaatg ttatagaact ttagttttta   78480
aataatgaaa aagggtagct ggcagatgaa tattacaggg ccatttcatt agtctttttc   78540
ctcccccatc tgtcagatat ttgattcaag tggcagccat ggattttctg gaactcagct   78600
acctcaaaac tccagtaact ccagtgaggt aaactttgct atagatggcc gccatccttgt  78660 tttacatgaa tgacacaaat gctaactttt tctgtttttt tttgtttgtt tttgtttttg   78720
tttttgagac gggagtctggc tctgttgccc aggctggagt gcagtggcac gatcttggct  78780
cactgcaagc ttcgcctccc gggttcatgc cattctcctg cctcagcctc ccgagtagct   78840
```

```
gggactacag gcgcccgcca ccacgcccgg ctaattttt  gtgtttttag tagacatggg  78900
gtttcaccgt gttagccacg atggtctcga tctcctgacc ttgtgatcca cccacctcgg  78960
cctcccaaag tgctgggatg acagggtgag ccacagcacc cggccacaaa tgctaactta  79020
agcgaggaat gctggttcag aatctttaca tgaactcctt gaaaatagat ttataattaa  79080
aatggtccca gtaggtattc tctaaagaga tagtcttgaa tgccaagcat tttggaggta  79140
tctaacctca tgttaactcc attttaaaat tagtgacatg actagactga agtcataata  79200
atatctttga tttatacatc tctattcctc agcagtactt accttcgttt gagagttcag  79260
tgaatacaaa attgcatttt cctctcaggg ttgtcaggga tcttcacata gatagtacat  79320
tctatgctgt gtctctccag gcgccgtcaa ggggagcctg agtaatgtct cctcatccct  79380
agaattgctt ctgaccaaac aaatcctcag aatgatttct gaatgaaatc ctagagcatg  79440
aaatcccaga tgtgcctatg cctcttccta gtgcctttt  caaacccaca acatccccat  79500
gaagctgtgt tatttaattt ctcctccacc aaataatttt ttttttttca gatggagtct  79560
cactctgttg cccaggctgg agtgcagtgg cgtgatctcg gctcactgaa acctctgcct  79620
cccaggttga agcagttctt ctgcctcagc ctcctgagta gctgggatta caggcacctg  79680
ccaccaaggc tggctaattt ttgtatttt  agtagagatg gggtttcact atgttggcca  79740
ggctggtctt gaactcctga cgtcgcgatc cacccacctc agtctcccaa agtgccgaga  79800
ttacaggcgt gagccactgc acccagccag ttcttactct gcacttacca tctcttactg  79860
ttagccactc tgtcaagtgc gtatgtcatg gctcccagga aagcttgtaa tcgatatagt  79920
ttatatatgc cctatttcta ttagatgtag tcatttaatg gctgaggatg actgattgt   79980
aataaaggcc cataatttta gggtcctatc tcttccagca ttatataaca atgtaaaatt  80040
cttactttga aagttaagag gcctggcatg gtggctcgtg cctgtaatcc cagaattttg  80100
ggaggctgag tcaggtggat catttgagac tagcctgggc aacatggtga aaccctgtct  80160
ctatcaaaaa tgcaaaaaat tatccgagtg tagtggcttg ctcctcggag gctgaggtgg  80220
gaggattgct tgagcctggg aggcagaggt tgcagtgagc caagatcgca ccactgcact  80280
ctgacctggg tggcagagta agaccccatc cctgaaaaaa gaaagttatg aaactatagc  80340
atcagtacac ttcctattaa cagagtttat gttggacttt gaaataaat  tttgctgatg  80400
tagccactta cagtgagaat ttaagcttag tgcttaagat gggctcaaat caacaggtcc  80460
catcgatgct ctaaggagtg agaagaaact atgatttctg catttgtttt actcctattt  80520
gttttagcta agcattactt gtgatgtagg gatactgaag aaattccttt catttatagg  80580
acaattttaa tgcagcctct gtaatttctg tgctatcgta cccagataac tagattcaga  80640
tagaatggca gatagaacta agggtgtaat ttgtttttt  atatctctgg gacttaaaat  80700
tctgcctgag ctggctaaat aattaatatt tcattttgct acttttcatc tgctaatcat  80760
tcttggagaa tacttgtaac ctgcacaaac ctatttttat acaataagta cattacgccc  80820
atttctataa cacagaaagg ctgttgtgag ggaggggccg tgtgcatttt aaactatttc  80880
actctaattg atgcatcata taacagccca acagtgagtc accctaattc aaaatctgtt  80940
aagtctggaa taaagccagt cttacttgaa cattttttta gaggacactt tggcttgcca  81000
aaaatgaaag cttttcataa cgaacgtctg atgagtaat  agtgagtctt acacggcctt  81060
tgaagggagg tgtttgtcat ggagattgtg acaacaaagt ccccactaag gctcagatgg  81120
cggcaacccc agaagcttca ttgcagaaat tgtgacagcc cctgggcctt ggccccttct  81180
tctggaaaat tggcttgggg tattccaact ttctgtggca gtgagtgaat gcagtattgt  81240
```

-continued

```
catcttagtc atgagctgta aactgaaaaa aaaacctaaa aaacccccaaa aaaccccaaa  81300 accaaaacaa acccccctaat attgttttct taaatggaaa atatgaatga aacagcttac  81360
tcttcaccac agtatggtaa tctgtttaga gagaatatta atacacaacc ctacatagca  81420
tatatatatg catacagcta gcgagctagc tagatccatc tttgtttttc tttcatatca  81480
accgatgtgt gggcctcagt ccaagaagga aataaacact ttctcttcta tgacatttta  81540
ctgttgttaa gaaaactggg agcgtgcaac tcccttttgt gttttctcct catctccctt  81600
gcaaatagac tttccttta tcagccactg tggtggtttg ggcccatttg tgacagccag  81660
attgtgattt tgctactcac ttcccttcag tgatccaagt agtaattaca agccatttga  81720
tccaaaagca tctgctgtga aacacacgg agtttcaatt ttttctcctt gctgcatact  81780
gagcataagt aatttgacat gtggtttcag gaccattgat gtaataataa taataataaa  81840
tacttctgtg gaatgccctc caaggagagc taaagtgatt tgcagacgtt cactagtcag  81900
tctggagtga ctgtggctgc agcccagtga tgttcccgtg tcgtgatggc cagttggagc  81960
tgactgcaag gtgatctgag cagcagtggc cagaacagtg gcccagggct ttggaacaaa  82020
ggatgattct caggaagttc tttatagtgg ccatcgctga aatgcagtag ctactcccag  82080
tacagtataa tgccctgatc cagcctcagc ttccaaaaaa aatctttaca atttatgtct  82140
ttcaaatgca attcctccca tcagtctcct aaccaccca cgaggctggc gttttaacc  82200 tcttttgaag gtgaaggaac agaagtgcag aggcactaga taacagcccc taacaaggct  82260
gagatttgac ctggattgcc ttgctattat tgtattttt ctgtctccat ttgcattctc  82320
aggaccagga aaccttgaag aggctagttg gaaatatata tatatatata tatatatata  82380
tatatatata tatatatatt tttttttttt ttttttttt ttttctttga tgggaggaag  82440
tagagtagga ggcgtggtag gtgcgtaaca gtcctggcaa aggtagccaa ccgtggaatt  82500
ctgggtggtt aaaaaggtta atttaacata gcagcatctt tgacatgggt aacctggaaa  82560
aagagttttc cagatggctc cattttaat gcttattttt aggattctct cttcttttta  82620
tgaaaagaat attggagaat atttcatctg gcttcctgaa actaaagcat gtgtattttc  82680
aacttggata gcattgacct tccttcagag aattaatcca actttccctc caaatgggca  82740
aagcttacaa caacctaaga gatctgtaag caccaagtag cttttctttt ttctagtttt  82800
aataaattaa ttttaaattc ttggtgcttc ctttgaataa ccaggtttta cttttcttga  82860
actgtataca tttgtgaggg ttgtgtgtgt gtgtgtgtgt gtgtgtgtgt gtgtctgtct  82920
gtctgtctgc ctaacacaca ccaaaaatta catttaactt tcattgagg gactctcttg  82980 agagggtctt actctttgat ggccttggct ttgataggcg tcttctcttc tatggttcac  83040
tagatcttgg gtcaacagtg tagactcaga aaaccattgc tcagagcagt tgtagcacag  83100
caccttgttt aatggatttt aataggatta tttcttttgt ccttccatcc ttccatctat  83160
ctgcacactt ttctcttgtc cagaacttat tctccttcaa taatctgtta attttcttc  83220 tcgaagcttc cagagagcat taagaacttg acactatgtc aacagatttg agtaagatac  83280
tgaaaacgga cagcgtttac ccttctgcct gtaatatgac tgtgaatttc tagttgtatc  83340
cagctcagca ctgaagtttt gggtgtgtcc tgggtgtggg acgcactgtg ttaatggctg  83400
agggagaatg aggatgcaga agacaaagcc tctgctggta ttcatcttct cctggtgcgg  83460
gacttagaag tgactctcct gtgagctggg ctttgccaaa tgctgtacca gggacatagg  83520
agagtaaact catctcaagtg agaggacttg agggcagaga aaggagagat aggagagaat  83580
tcataagaca ggggcatttt aaaccaggtt ggagggtata tatggtttca gcactgactc  83640
```

```
tacttgtaag gacggtacag cagagagagg agatggaagt gagcaccggt gtggagcagg    83700
agcatgccac tcccttctgg ggaatgttcc ctgagccatt ctgttcaatg ggaacatggt    83760
gtgtggctta gaataatgga aagtaatcag gagatttggg ttgcacccat tttatataaa    83820
gggagttaac tgccaggcgg gcattctgtg tagtatagtg gtggtgtgaa ccagctcatc    83880
ccagacttcc acccttcaga tccccggagt accataggca ctagttgtgt aaacttgggc    83940
aagtttctag aatttcctga gccatatttt tcttgccttt tccataggaa gtgatgatgg    84000
tgccttcctg agagggctgg ctgtgagtgg tgagtgaact gatggcacat caggagcttg    84060
tttcatttgg tctcacgaga tgcagtcttt tttttttttt gagatggagc ctccctctgt    84120
cgcccaggct ggagtgcagt ggcacgatct tggctcactg caacctctgc ctcccaggtt    84180
caagctgttc tcctgcctca gcctcctgag tagctgggc tacagacgcg tgccaccatg    84240
cccggataat ttttattttt agtagagata gggttttacc atgttggcca ggctggtctt    84300
gaactcatga ccttaggtga tccactggcc tcggcctccc aaagtgctgg aattacagac    84360
gtgagccatg gcgcccggcc aagtgataca gtctttctct gattgtcagt aacggtgaga    84420
acaagagggt gtgaaggcac agtgttaatt tgtactgctc atgttcctcc cacacctgtt    84480
tatccataat tacgttcttc ctgatctcca aaagtgcagc agtaaattaa ttgctctgtc    84540
accctcagtg ggagcctgtg acttcctccg ggccttgttc tttgtgatgt ttcttactcc    84600
acagtgacct ctgctgggtt ttagtttgct tctcaacaag cctggtttca gaggtggggc    84660
ctgcaccttt aaggcagcat ctgtttgttg ctaagcaccg ggttgaaatc actgcccaga    84720
tgaaaagtac ccgagagaat gaaccaggga aaaaatgtg cctgtgtaag acaagagcct    84780
ttagcagaga gtgtccgggc tggttcctgg catccctggc tccttgcatc tggtcctgtc    84840
ttttcctttg gcattggcac gtgtggggat gtgcattctg gctgtgatca tccttccaga    84900
aaaatgtact gaaagcgaca gatccaagac aaatccagaa atgtcacttc aaaattgagc    84960
accatgtttt caaaagatg gcacagagag acagattttt cccttgcttt cttcttttaa    85020
atttctttac gatgtctctt ctagttttta aatcctgcat aggaggatct tttactttgt    85080
atttaaaaat gcatggaatt caaagtaaaa tcacccatta atgataactt taaagtatga    85140
tgaatgatat ataataatgt gatagtattg aatctacagg tgacattttc tggtatgtaa    85200
ggtgtttcac ataagtgacc tcttttgctc acaaaaactt aagtaacaag taattttttc    85260
aatatgaatt atattaataa tatcctcttt tacaaaacag gagctgaatc gtacgtagca    85320
aggtaaatct tgtcctaggc cacactttgc tggtagagtc tgtgacttt gatttcgaag    85380 ccccaaatct tttctttact gctatgtgaa tataagaacc tacccagaga gaaacatgtc    85440
tacatcgctt aagaaatgta tgctatttt gttatgaatt acaaaaggac gtattagcat    85500
gaagtcagca attgttgtga tgatgtagtt ggcacactac acttttttgg gaaaggcttc    85560
ctgaaggtgg tattctttga gatgattttc caacagtgtc tatgtgtgag atagctgaag    85620
gatagagaaa agatttccca ggactatggg ttaattttaa ggaacaaata gatttctgtc    85680
agtgatgagt caggctaaaa ttaaaaagaa gaaacaaaga caaaaacaca gatagtctta    85740
gaagagaaag cttgtgctgg attaagtgca gttcagagtc aggatggcag gcagatgtca    85800
gtgaccatgg acaaggtgtg tctggaattc agtgggaggt cagagaggga ttatggctga    85860
gatgcaggct tcacagtggc ccttctcaac catgatccca gagcagtaag cgtggatact    85920
cagcagccct tacatggatt gcggtgttct tttttattt tttgagacag actcttactc    85980
tgttgcccag gctggagtgc agtggcatga tcttggctca ctgcaacctc tgcctcccag    86040
```

```
gttcaagcga ttcttctgcc tcagcttccc aagtagctgg gactacaggc gcacgtcagc   86100
acacctggct aattttttgta ttttttagtag agacgctgtt tcaccatgtt ggccaggctg   86160
gtctcgaact cctgacctca ggtgatccac ccgccttggc ctcccaaagt gctgggatta   86220
caggcgtgag ccaccgttcc cagccggatt gtggtgttct aacttggcat aagcggtcaa   86280
ttgacacagt ggaaagaaca caggacaggc agtcactaac tttcactctg cttcccatgg   86340
ctgcagtttc atctgataaa atgagtgagg aaacgttgtc agcctcagag ggctgtgaga   86400
agccagtgat gtgaagcgtg tgagcgttta ctctaaatac tccgtaaatg aacaggacat   86460
ttggccggtg gtttccttca tttgttaatc aaatttgtct gcatttcttt ttggcatcta   86520
caaacaggtc gatgaacttc tgcatatata tggttcaaca gtagacggtg ttccccgaga   86580
caatgcatgg gaaatccaga cttatgtcca ctttcaggac aatcacggag ttactgtagg   86640
gatcaagcca gagcacagag tagaagatat tttgactttg gcatgcaagg taacggattt   86700
tgctgcagaa atatatttct gaatagaaat aatcattaat gttgcaatct tatgccttct   86760
aaattcatgt gatattcaag ggcccagttt ccatgccagg aacatatta gcatatttat    86820 tagttaatat atttattagc atattcatta atttgcattc tattccttga tctctttaga   86880
agaatgagtt attaggtcat gatcccacac ttccatgaag aacctgagct aatctactga   86940
aattctatgt atactttgat atctagaata attatgaaat ccgttgctat ttaagttact   87000
tagagatggt gtgttataag aaggcggcat aaactttgag gtaatttaat ttaatcctaa   87060
atagttttat cggatttctc cagattaaac acgaaacttg atatattcac agttgcttta   87120
tggagattaa tataagatga tgtttttattc attttttcaaa ctgggtttca ttcctgatct   87180
gagaagggag tttatggtaa gtcttaaaga gagccctctg agagagaata tattcagcaa   87240
catcagatca gaagctttta gaccaccagg tggtgcagta gagcttaaat agttttaagt   87300
ttccagagaa aatacaatca actatgttga aatggtgaaa aaggcatata gagttttggca   87360 acacttaatc atgtgcactt aataaatgtg aaaaatgttt aatttttagtc ccccttttt    87420 actttgactt gaaacattag gattctctac atttatatgt agtttatatc cttaggaact   87480
taatttcctt ttgctcccat atgtaacgtt tttattcaga aaaccaacaa tgttctatac   87540
caatgatatc ctccattaaa ctgataattt tctgagtaat aaagggtatc agaagtagtg   87600
ggtcagctgg gagcagtggc tcatgcctgt aatcccagca cttggggagg ccgaggaggt   87660
caggagatcg agaccatcct ggctaacacg gtgaaacccc gtctctacta aaaatacaaa   87720
aaattagctg ggtgtggtgg cgggcgcctg tagtcccagc tactcgggag gcagaggcag   87780
gagaatggcg tcaacctggg aggtggagct tgccttaagc cgagatggct ccactgcacc   87840
ccagcctggg cgacagagca agactccgtc tcaaattaaa aaaaaaaaa aaaaaaaaa    87900 gatgtagtgg gtcaatttga cccagttaga gcataggcct gagataaatt tctcactgtt   87960
gaaaatatgc atgcgagaga aaatatgagt gtgtgtgcgt acacatttc gttttgaaag    88020 tttttggagt aggacattct taagtctgta gatttgttaa cattttacaa atttctgtac   88080
tttagtaatg agaaacaagg ttaggcttaa cctaactaaa gagatggcat ttgctgagct   88140
gataagattt attttactgt cagatatgtt ctaccgtaat ctcttaaaaa tgcatctctt   88200
gcctttaatc ataagcaata ttgttcagcg aaaaccttct taaaaataat tgtcctcctt   88260
tacttttttg catacaagta tttatttatt tatttattta tttgagttgg agtcttgctg   88320
ttatcaccca gactgagtg cagtggtgct acctcagctc actgcaacct ccacctcctg    88380
ggttcaatcg attctcctgc ctcagcctcc cgagtagcta gtattatagg tgtgtgccac   88440
```

-continued

```
tacacctggc taattttttgt atttttacta tagtcgatgt tttgctgtat tggctaggct    88500
ggtctccaac tcctgacctc aagtgatcca cccgccttgg cctcccaaag tgctgggatt    88560
acaggtgtga gccgctgccc ctggcctgca tacaagtatt taaattcgag ctcttatata    88620
ggtttaaatt cagcaaatta tatgcagtat tcttttagag atttctactt tgattttttaa   88680 taagcctgct aaccaatgat ggatttagaa agagcattta aaatctgaat aactgtcttt    88740
ttctttatag atgaggcagt tggaacccag ccattatggc ctacagcttc gaaaattagt    88800
agatgacaat gttgagtatt gcatccctgc accatatgaa tatatgcaac aacaggtaag    88860
tgtgcactag ctttaggaag ggaaactgaa ccacatctat ggccctttga ttttgaaaaa    88920 tgtcatttttt ggggaaaatt ctgtttaaat ttggcgtcta gtttggaaac agtctctata   88980
taaacggtat cttaacagct ttcttgtttt atgaaaaata gtgtcaaagt aatttttttga  89040 ggtatcataa catgagatcc tctgattttg ttgttttcac cttttgcagg tttatgatga    89100
aatagaagtc tttccactaa atgtttatga cgtgcagctc acgaagactg ggagtgtgtg    89160
tgactttggt gagtgtaagg aatgccccctt tcagggaatt gtgttgttca tctttgccta   89220
ctttgcccca gcatctttgg acttaatttt ttccccttac attcacattt tcagaatata    89280
tgacagtagt ttctgaactt cctttctctt ccttcatttc tatttattga tattagcagg    89340
tgacacagat aggtattagt attagaggga aatgccaaag taattaaatg gaatgaatat    89400
aaaattgatg ggaatttgaa aatatagatt aataacacaa tgaatgtact gtgtgctggt    89460
gctgctctga gcagaccaac tcatgattca tatgacagtt gctttcatct ctagtgtctt    89520
tgctcttagt tttctcttcc cacctggaat gctcccccttc tttcctcttt cttcccccat   89580
ccctcctctc tggtgacatg aatcctgctg tccttcaaga actaactcaa ggtcttttctt  89640 gaagaagccg tgtctgattg ctttagcttt acttccttct ttcttccctg agtttaacag    89700
ttgagggtca gctgggcgcc gtggctcatg cctgtaatcc cagcactttg ggaggccaag    89760
gcgggcagat cacctgaggt cgggagttcg agaccagcct gaccaacatg gagaaacccc   89820
ctctctacta aaaatacaaa attagccaag catggtggta catgcctgta atcccagcta    89880
ctcgggaggc tgaggcagga gaatcgcttg aacctgggag gcagaggttg cagtgagccg    89940
taagccaaga ttgcaccact gtactctagc ctgggcgaca agagcgaaac tccgtctcaa    90000
aacaaaacaa aacaaaaaaa cagttaaggg tcagtacttc tgaagtcact tcatagcatc    90060
atttcctaca tttctccttg attagataat gattggtaaa tacttccata gaaacactga    90120
atgattagat aatgattggt aaatacctcc atagaaacac tgtttcttac cttgttaaat    90180
atatcgatac atgattttttt ccttaaaatg attcaaacta ataataaagt ttataatatg   90240
ttaaaatgtc cttttttagga tgccttcgtt ttttaaaaat ttgtataatc ttttctgacc   90300
cccatgttat ttttttattt tttattttttt ttgagacata gtcttgctct gtcacccagg   90360
ctggagtgca gtggcatgat ctcggctcac tgcaacctcc gcctcctggg ttcaagcaat    90420
tctccctgcc tcagcctccc aagtagctgg gattacaggc accgtgcttg ccaccacacc    90480 tggctaatttt ttgtatttttt agtagagacg gggtttcacc atgttggcca ggctgctctt  90540
gaactcctgg actcaagtga tccgcccacc tcagcctccc aaagtgctgg gattacaggc    90600
atgagccact gtgcccggac ccatgttat gttggttttt cctttgaagc cctcttagcc     90660
ttttttctcc tcctcttggc cttcactgtg cttttttgtgg ttgccatttg tgttcatctt   90720
tgtattggaa tggatgaatg aagacattgc aaagatactc tctggtgaga ccatattcta    90780
ccagcagaag atactctctg gtgagaccat aatctgccag gctctgctgg ggtcacagca    90840
```

```
gagacctagg gaacaggaca ttcttgctgt cctcaaagaa ctctccgtat taggggacca    90900
agacatggaa acctgtgctc ctcactgtgg catcacagag ggggacacta agtcaggagc    90960
catgcattca gaagagggaa ggtctgccta ggatttgcat gtagtcttat gtatttaggg    91020
caagcaccgt attcatccaa gcattttttc accttcttaa aatgctcaac cccaaacata    91080
gttgtttctc aacaattatt tgttgtattg aactgaattt catgtatttc agtgagagta    91140 ttttttgct gttaaatttg cctaaatttt taattgtggt aatagacata taacataaaa     91200
tttatcgtct tgaccacttt taggtgtaca gttttgtgat gttaagtaca ttcacaatgt    91260
tgtgctacca tcatctatct ctagaaatct tttcgtcttg taaagctgaa ctctgtaccc    91320
atttaacacc aattcctcat actgtccttc ccccagcccc tggcaaccac cagtttgtta    91380
atactttgta tctctcggaa ttcccctagc aaccaccatt ctattaatac tttctacctc    91440
tctgaagttg actgctctag ctactcacgt aaatagtatc atactgtgtt gtctatttgt    91500
gactgacata ttttacttag catattctcc tcaaagttca cccaaattgt agcatatgcc    91560
aagatatttt tccttttttaa gactgaatga tactccactg tatgcataga tcacattttg   91620
cttatccatc cgtctattga cagacagttg ggttatttcc acctcttggc tattgtgaat    91680
tacgctgtta tgcgtgtggg tgcatggtct caccttttgga ataaaagtta tgtttttata   91740
tttcttaagc ctctcgtttg acatttgtct ttttctgccc ctgcaagata tttatacttt    91800
caaaatagct gtaatttcga ctttctcaac atactgtact tatgagaaaa gatgttcaag    91860
gagatactgc cggtgtggtt ggagaaattc agtgtggtgg gctgagactt gcttttttcct  91920 tttgttttca ttcctagggt ttgcagttac agcgcaggtg gatgagcgtc agcatctcag    91980
ccggatattt ataagcgacg ttcttcccga tggcctggcg tatggggaag gtccgtgtgg    92040
cacaccgtgc ccctgttgcc tcttaatttg aaactgtggg atacagtctg gctagtgaat    92100
gtttcttctt acagttttgt cagaaaaagg ttgctcctgg aatttttaaag aaagtaaacg   92160 taagagttta attggaaatg cgaccaaaca cagcggctcg ctcgcataaa cccagctgct    92220
caggaggctg aggtgggagg atgggaggat tgcttgagcc caggagccca agaccagcct    92280
gggagacaga gtgagactcc tgcctccgta aaaaaggaca gagagagaga aaagaaagaa    92340
aatgcatatg cctatatata gagagagcat gtgtgtgtgt gtgtttaaaa gagtaagtgt    92400
atacatatat atagacagag ggaaggagga agagagtgtg agacagacag gcggacacgg    92460
atggaacaaa gttaacatgg gaacactaga aaaacaacg aatgagtggt tctcaggagg     92520
ctgaggcaca agaatctctt gaaccgggga gacagaggtt gcagtgagct gagatctttc    92580
aaactgtttc ttcgaatagt agctgtgaga gagctaacat tgttttgct cttagtggca     92640 tctaaatact atacattttg gcccttaat tctttttttgt ttttcttatt taaaagacga    92700
agtcttgcta tatagcccca ggctggcctc aaactcctgg gctcaagtga tcttcctgtc    92760
tctgcctcct gattagctgg gactacaggc acctgccact gtgcctggct ggcactttct    92820
ttgaagaaag caacaaacaa aacagtccct acgagtacat ggtttgagtt tgcagccttc    92880
tttcatctga aaatatttct cacagtaatc cctctctctt ttttctgttt ctccttcctt    92940
tttctcaggg ctgagaaagg gcaatgagat catgacctta aatgggaag ctgtgtctga     93000 tcttgacctt aagcagatgg aggccctgtt ttctgagaag agcgtcggac tcactctgat    93060
tgcccggcct ccggacacaa aagcaaccct gtgtacatcc tggtcagaca gtgacctgtt    93120
ctccagggac cagaagagtc tgctgccccc tcctaaccag tcccaactgc tggaggaatt    93180
cctggataac tttaaaaaga atacagccaa tggtaaggct ttgttctgtc ttccttctta   93240
```

```
actgctggta tcaacagcca atattttag gctgtaattt tgcttgcaaa ctcagattat    93300
ttaagctgtt caaagaatgt tttctaattt attagaagaa cacagatgcc aactggagta    93360
gattttatca aaatttcatg cgttttagta attatagcgc tttcattaaa atagaaaata    93420 attattttg cacaaaataa catttaaaaa aaaatcatgg actctttaaa aatcacccat    93480
aatgtttagt cttgtagttc ctttgtgact gaaggcagat gaaagcctgc ataaatgcca    93540
aagtggaaag attttctta tttagttgaa tctaaggcac aaccattttg cagtcttctg    93600
ttgggctctt agaacagccc gtgcatttca gttcagttat atcttttgtt aagtactact    93660
ttattaataa acagcaaact ttctttttta aaatttattt ttatttttat ttttttttga    93720
gacagagtct cactctgtca cccaggctgg agtgcagtgg cacaatctca gctcactgca    93780
agctctgtct cccgggttca agagattctc gtgcctcagc ctcctgagta gctgagacta    93840
caaacgtgta ccaccatgcc tcgctaattt ttgcattttt agtagaggtg gggtttcagc    93900
atgttgccca gactggtctc aaactcctga cctcaggtga tctacccgcc tcggtctccc    93960
agagtgctgg gattacaggc atgagccacc gtgcctggcc agtaaacagc aaacttttaa    94020
tgtaggtcat gaattttaaa actttgtgaa ggcctaaaaa tgaaaaactg tgtgccagtt    94080
tagttttctc acggtaagac ttccatatga ggaaatcatt tgaaggtctg aagttttgag    94140
ttgatcattc atgtgtattt catgtactgc agtcaagtaa attaggggct cggctagtac    94200
tgaaaaccag tagtttcgct ttatacctct ggagagcccg ggtcaagctc cacaggagac    94260
caagtgtggg gtctttttcc tgggagaaca cagagcaatt tttatactta attacgataa    94320
taatggattt ccaattgaaa tctctgcatg attaccaaaa atgaatgaaa aaacaccaaa    94380
gagaagttgt taggattgat ttaattataa aggaagttta ttaggtcatt tttggaatta    94440
aaaaatcaga tggtaagatt tgcgattcaa taaggtatct cgtgctttct cctcctctct    94500
tggggctttc ctctaattta aaatgccatt aaatggacta ttggcatata aaagtgaatg    94560
tcataaaaca aaaattatga tggaacttat taattacttg ggtatattag ggccatcatt    94620
cagctaccct gggctgctgt tatgggcctg agtattccat ataatacata catgtgtcca    94680
tttgttggat tcattactct tgagggatac attcactacc tgtgttatgt ctctatgtat    94740
tttatcataa taagaaatta ccacagaggc tataatactt ttggtacttg cgggaatgaa    94800
ttcctgtaga aagtagagaa aggggcaaat ttacctttt ttttttttt tttttttga    94860 gacagtcttg ctctgtcacc caggctggag tgcagtggcg caatcttggc ttagtgcaac    94920
ctccacctcc cggtttctag tgattccctt gcctcagcct ctgaagtagc tgggactaca    94980
ggaacatgcc accacgcctg gctaatttct gcgttttaa tagagatggg gtttcaccat    95040
gttggccagc ctggtcttga actcctgacc tcaagcgatc caccctcctc agcctcccaa    95100
agtgctggga ttacaggtgt aagcaaccgc gcccggctgt ttttctttt tttttaaatt    95160 ttttttaaa tagtaaggat caagcaggtg agttaagcca cttttattta ttattttatt    95220
tatttattta tttatttatt tatttattta ttggcaagga aacagaataa agaggcagtc    95280
ctggatctgt taaatagcta ttctattact catcttaggc agccattcgg actgtctaat    95340
cctttacaac caatgtctgt gtggacagag agcttagtta gccaggcagg cacggtgctt    95400
gtccacatca cgtcctcctg atggaatctt gcaggttctt ccactaccag cctagtggga    95460
gccactaacc cttttcctggt gtcctggcaa gactgtgctc tgtgggtgtg acagtctccc    95520
aggcagcgcc ccgcccacct ctgccctgag ctttaccatt cctcccctct cctaagctcc    95580
aggtggctgt tccatagtga tgtcgcctgt gctggaaaaa acagccccag cagactcctt    95640
```

```
ccccagacac cacaaacaga ggcttttctt tttcttttcg aggtagttgc gttgcttgtg   95700
aaggaagtta catgcctttg ggcaaacatc tcagaaggaa gtcttccatt ttgaaggttg   95760
aggggaaaag aaaataaggg taggtgggtg gattaaaaga taaaagtgaa aaaagaccag   95820
gtctctcatt catatgcaac atctgaatga caagagaagc ctgtgtttgt ggaaactctg   95880
agagatggca gggtgacaag catacaggtt ttgagtcaga cgtgggttca ggtcctgggc   95940
tgccctatac tggttttttg actcacccag ggagttctgg gctttggtgg atgctacccc   96000
agcctcttta ccctggtgga aacggttctg aggtgcagtc tacacagctc tgcagatggg   96060
ccctggaatg agccccagct gtacacagca gcctcgcttt cacacctccc atgggcttcc   96120
tgcccttctt gcctcactgt ccctaccect tcctttggga atctcggggt caccttccaa   96180
ataaacttct gtactcaagt ccttgactca gactctgctt ttaggggagc ccgaatgaag   96240
atgctgagcc tcacttttct catccagagg ataatgtttc tcccctgccc ctgtggtccc   96300
tgtgagtttg gggagttcc tgtctgtggc atgttcagcc cagcgtttca cttggcagga   96360
attctgaaaa cgtgcttctc ctcctcctcc ctcgcttttg cagcttcctg ttttattaaa   96420
aattaccttg atttacttt gcaatgaatt agaaaacagt aatcccattt tttaactaaa   96480
aaagttaaaa tttacggaaa tcaaaaattt aaatgacttt gaaaaacagt ttttaataca   96540
actttgaatt ataacttagc agtggccggc catttgagag cctgcctttc cctaaatttc   96600 actttcccctt ggcattgcta gaaggcaacc atgtacttga aaagaaggaa agttctgttt   96660
gcttttccag agaagccaat cctttgcttg ctataaaaac caaatggctg gctctctggg   96720
aaagaagacc tgttttttta aaatagaaat tataagaata tcagaaagta gatgaaaagg   96780
aaagccttaa gcacttgttt gggcttatgt tgcccttcca agcagaatat ttatagcccc   96840
ctgtcgagca cttaaaatgt gtgggggacc ctgggaacaa gctacacaga gttcagggct   96900
ttcagtcata tcctgaagtt tacgttgctt aacttttgtc tcttgatcag tttcaagtgg   96960 gaaaaaaat ctgtctctgt ctatatctct atatctaatg aatctttac tgaaagaagt   97020 gttagtcaca gtggcaggtc ccaggaagct aggggggttgc ttgtgggttg ctattaaggt   97080
tctgcttttc tagaaaagaa gcatccttgc agtatttgac attcattgat actaataatg   97140
tttaggaaaa tgggtctcaa acttcctagt gcccaagact cacctgctga gcttaatgaa   97200
aatgcagatt ccagggtttt gctgtgggtg cacctcctgc aagaggcttg gggcagtgca   97260
accccccctc ccccaccccg ccccctttt tttttttttt ttttttttga gatgaagttt   97320
tgctcttgtt gcccaggctg gagtgcaatg gtgcaatctt ggctcaccgc aacctccacc   97380
tcctggttca agggattctc ctgcctcagc ctcccgagta gctgggatta caggcatgca   97440
ccaccacgcc tggctaattt tgttttttta gtagagacaa ggtttctcca tgttggtcag   97500
gctggtctcg aactcccaac ctcgggtgat ctgcccgcct cgacctccca aagtgctggg   97560
attacacgtg tgagtcactg tgctcggccg caagccccat ttttaacttg cgcaggtgtg   97620
gaaagcagcc ttgagagcc agcctctcta gcctgcattg gctggagagc agcccagggg   97680
ctggcgtgag cactcccgct gcccccttggc cattagtcta caagaggtgg cctgaactga   97740
ggcagtagga cttactgttt cctgaggcct tctatgccga ggttttgagg atggaatgag   97800
ataatgtgtg caaagttccc ggcacatgat ctctgttgcg catgtgtgtt cttaggaatt   97860
gtgtgtccca aacctccacc attgtctttc ctcgtgcgct cagaatgcag gcagtcgact   97920
cttagctcac ctcgtttatt gctgggcccg tgcttggaag acaccatgtt ccatttggca   97980
aatcgcttac actgggaagc aaagaacttc cagcattcac cagcttcact ccactatgcc   98040
```

```
tgtgatgctc tgtgaggagc ggaagagaca ggaatatatg gagaatcgtt gagggttcag    98100
tatgaagttc ctctgttgcc tacaaaatga gtgaccattt gattttgcct agaagggctt    98160
aaatttctgt tctagttatt cacagtggag agaggaaatg tccgtaggct gtatttgact    98220
tgagcggaaa tatcatctgt aaaaactttt tatggagaga attaatttta ccactggaat    98280
tccccagaga ggccagtgtt atttcagagc caacaaggca accattgaag ggattggaca    98340
ggccagacct gtttatactg ggatcctgtt aatgccatac ttgtgatttg tgtatgaaaa    98400
tcccttttct agtgtttgcc atcttttgaa acattccagc agcttttaag aaagtctcat    98460
tgggcataga gtttctgaat aaagtcttta tgtaaacact gaacttgtcg cattaatgaa    98520
ttctccatct ataaacagcc attaatccta ccttgttagg attggaggtg tatttaatag    98580
gggacaaaaa tagaaaagac ctatgttcct ccttccattt agacgatgta aatccaacac    98640
aggcttacca gatgatgaag gtaattgcag cctgaggttc ttttttttagc ctccacgccc    98700 cctttgaatc attctttttt taaatcgctg tgagtagcgt tgagtctcaa gctaccagaa    98760
gccacttcga tgtaaatttg ctctttggaa tgaattgctc ttgggaatgt atgtgtccat    98820
tatatagctt ctcaccaggg aaaagcatta tagagccagc tctgatgtgg caaacccact    98880
tatttcctgt ttatgagagt gagggcattt tggcttccat agcctgttta ggatgactaa    98940
cagcatttag ctcagagaat gctctgtttg tgtgtaaaac tgctattagt gagtctggct    99000
ggctgatacc ccagatttcc agatgtaaaa acatattagt gttcctaaag atgagtggta    99060 ctttttttt ttttaaatca gaaaacaatc tgattgggaa atactggttt taccaggaca    99120
cagaactttg gtctcagaat tacgagtttg ttttgtctgt gctgaagatc ggtttcattt    99180
ccaccagtgt ggaagtgagc gtgtggcttt cttttagtgg tggaaaaaat taagatcctg    99240
gatactaatt tccttataaa acttagtttt gtttgattct cttttctta ttctcagtca    99300 tttatttatt cacttgtgta tttaacagat aaccttttgt taaatgtcga aggtacataa    99360
aggtgaatta cacattattt catactctca agaagctcat agttgaattg gaaaacactt    99420
gtaaatcctg gctccaaaga aaaaaaaat tgcaatgaag agaattagag gtcagaggtg    99480
ggatttccac taattttct gttttacaag agcaaaggca cccagaagca aggcacaggg    99540
ctctcagcat cagcatcaga ggacagtttc tagaagggtt tgtgtttgat ctcagcgctg    99600
cagttggaca ggccatggac ctggaggtgt gtggtggggg gatttggtgg agggaagggc    99660
ctttcacata gagcaagcaa gctggaagac agaggctgca tgtagaggtc acgggaagaa    99720
aggttggaaa gtctattggg gccagattgt agaaaaccct gaattccagg aatttataac    99780
gtatcgttgc atgtatctga aaaccaact agctaattaa ctaactaatg aatattgtat    99840
tactacttcc ccctgccttc tataaaatat agagaacttg tctgctcatt tgatggccac    99900
tggagtgtgt gtgtgacttg aaaagcttgc ccctgcctgt cacctctctg atcccaccac    99960
tctagcttca ttcctttgga tcttaaagta ttgtcatgtt gaatgatcag aagcccctta   100020
taaaataaat attcagatgt tttagaggaa agagtgaata aaggaacccc tatatgttct   100080
ctgtaaaacc taagtcttcc tcagcactgg gaagccgtct ccactaaagt gtggtcctca   100140
ccggtcccct ttaggggtga ggtagatgga ttaacatcct gctggcctgt gacagggatg   100200
gctggtgggg aggggacacc ccatggcaaa gaggaccagg cagtatgagg gtcaggagga   100260
gagatgttaa ataaacgttc ccagcatttt gagtaaaaat cagtcttggc ttttctctcc   100320
gaacattaac tataaataca actttcgat aaaaatctac agaagttctc tgaagcacac   100380
tgtgtgaaat atctgttggc tctgccactt ttgatagaca tttgagagtt tgggatgcca   100440
```

```
ggcaggtctc ctatgaaggt agagtgagcc ggctctctgt gaagcagtag ttctatgaaa 100500
ctattggctg ctgagaagag gaaactttac agcctgttac ataaggaaaa ggaaaaaaaa 100560
aaagatctca ctttcctgtc ggtgttatga gtactggctg ccaaatggtg cttgtttgtg 100620
tttctatttt tttcctcctt cttttgtaag gggcttgaaa atgaattcta tttctcactt 100680
tattcctgcc tatgaaggaa gtgagatcat tgggaaggac caagtatgaa aatcttcttt 100740
ttagctctcg tgtttagaga taactgtatt gtgacactat cttcgctttt tcagattggt 100800
aatacatgcg catggtacaa aatgccagca gtgtagaagg gtaaacggtg acagctaagt 100860
cccctaagc tacatcgggc agtggtgaag agcatggaca ccatctgatg acctggttca 100920
ggtcctggct ccagcctctc ctactcacta gctgtgtgac cttggacaag tcacttaacc 100980
tgaaagctca gttttccaa gtgtaaaatg gtctaggatt tttgtaggag caacggacta 101040
gtatttggaa agcaccagat actgcctggc acgtagtaaa tgccatgtaa gtgtgtgttg 101100
aatacgcaga tacattcctc ctaccctgtt cttagccatg cagtgtctct tccagaggtc 101160
atcattgttc ttagtgtctt tctcatcctg gcctggagaa ttctaaatat tggggaaaat 101220
tggctgggcg cggtggctca tgcctgtaat cccaggactt tgggaggctg aggcaggcca 101280
atcatttgag ctcagcagtt caagaccagc ctgtgcaaca tggtgaaacc ctgtctttac 101340
taaaaataca aaaattagcc aggcgttgtg gcgcacacct gtagttcaag ctatcactcg 101400
ggaggctgag gcaggagaat cgcttgaacc caggaggtgg aggttgtagt gagccaagat 101460
tgcgccactg cattccagcc tggatgacag agtgagactc tgtctcataa aaacaacaa 101520
caaaaaaaa aaattgggga aaataatggg gtattttct gccttgtttt tactccattg 101580
tcttagtaca tggctatggt ggagagaata atggcccacc ccaaacatgt ccacattcga 101640
atccccagaa cctgtgaata tggcaaaagg gattttaaat ttcaaaagac tttgaagata 101700
tgattaagtt aactatcttg agatggggga tggattttca tggattatgt gggggggccca 101760
gtgtagtcac agggtctttt actggaggga ggagggtcag aatcagagaa gtaaatgtga 101820
tgagggaggg agagagttga cagccacgag ccaaggaatg caggcagcct ctagaatttg 101880
gaaaagggat ggaaagagtc ctcccttaca gcctccagat agaacacagc cctgtggcct 101940
taatcttctg attttcagaa ctgtaaggta ataaactgag tttacatgtc aagcaccatg 102000
tttgatggca gaaatacaaa catgaaaaaa aaacaacaca gttctggtat tcggggtgcc 102060
atggtctgga ggcagacgtg tgtacagaca gcagtcataa tccactattg tcattactct 102120
agttttacag ttcttggact tgtcggtctc tttctggacg cttactgtt aaaaattatt 102180
gagggcccta aagagcttta gttatgcggg ccacatctat atctattgat attgactgta 102240
ttagaaatgt aaactgagca atgtccaaaa tgtttgttta acataacaat agtggatcca 102300
tttttatgta aacacaataa acattctttt aatgaaatgt ctcctcaaac caaaaaaaaa 102360
aaaaacttag tgagtagcct tattttacat ttttgcaaat ttctttaatg tgcatcttaa 102420
tagaagaaaa ctagattctc atatcagcat ctacattcag tctgttgcag tgtattgctt 102480
tggtggaagt tatttaaaga aaattcattc ttatacaggt acatgtagtt ggaaaaggga 102540
ggagtatttt gatactcctt tcagacaact gtggatattc tttcatgtgt tcccaaactc 102600
agcaagtggc catttcttca aggttggttg caatgcggaa cctgaggcat tattggtgga 102660
cttttcttat ttggtagcat taaaattcat tggcctatct tgtacttgga atagatcttt 102720
tactcatgcg tgatttcata acatgcattg tttatttgga aatatggaat cactaagtta 102780
tgtagatctt ccaaatgtgg acatttcatt tcacagtatt aaaaattact ttcaggccag 102840
```

```
tcacggtggc tcacacctgt aatcccagga ttttgggagg ccgaggtggg aggatggctt   102900
gaggccagga gattgagacc agcctgggca atgtagtgag atcctatctc tacaaaaaat   102960
aaaaaattag ctgggcatgg tggcttgtgc ctgtagtcca agctacttag gaggctgagg   103020
tgggaggatt gcttgagtct gggaggttga ggcttcagtg agctgtggat tgtgccaccg   103080
cactcagcct gggggacaga gcgagacctt gtctcaaaaa aaaatgtcac actcagatct   103140
cattggaaaa gtattgggaa gctcacggtg gcagatacaa attttccaaa attctgattt   103200
ttgttggaca gtttgaatta tatctaccaa taccgtcagg ctcattttgt tcattttaaa   103260
gaaaatgttt ttttctcacc tttatttttcc aagtaaaaat tgtggttctt gaaaaaagac   103320
agttagttcc gctcccaaca cagttgtaca tatgttttttc ctcaatgcta cgattgtgct   103380
tgggtatgca gctgacgagt tgtatgtgtg cttcctgaac atgttccaag ggtgagggtt   103440
taggaaaatt accaattttt gctgctccat tgaggacatt cttaagtgaa actggcgcat   103500
ttttaaatgt aagagtgtgg caatgaagag cgcaatggtg ctgagcacag tttggtgttc   103560
ctgccttatt tgtgctgaga cagcagcaga tgctttgcac catcagtgca catgtcctca   103620
gagagcaaaa ggcaaatgac atttgacatt tgacatttttt ctgaaaataa ttttcaactt   103680
gtggactccc tggaagggtc ttggtgaccc caggagtcta cagaccacac ctggagaagg   103740
gctgttccga tacatatgga gcagcaacac agaggagcag aaaactcatg ttccaggttg   103800
atcagggcca ctctccaggg agggtctcac ctttgttaac ccctagggaa tgagaaggta   103860
gatgaggggg catagagcgt tccaggcgca gagaagccgg gaggaggccg gggctgtcta   103920
gctgtgggga ggtgtgtgag taactcagat ggttggagac tcaggtgcaa atgggggaaga  103980 ggagaaggta gggtgagaca ggtgagcagg gccaggtgac aaagggtcca cggagctgcg   104040
agcagcctgg atgtaaagat ccacagggaa aagatgatca gggtatggtg ggtcagattt   104100
gtaggttaga aagacaggca gccccggtgc cagccaggga agggcattgc agctgctgct   104160
agtcctctaa gagatgacca agggtggcca ggcaccaatg ggctgagagg tgggtggcac   104220
agcatggcag gcagtccctg cccttccctc cctcagagca cataggtagg aggagatact   104280
ctgtcctcct cctttacagg gactctgtct tgtatttgtc accaataaat cactgggcac   104340
ataagtagag tcattcaaca aatatttgct tgaacatttg aacaaatgag tagaggatat   104400
aggaacaaca agactcagaa tatgagaaag aagaaaccc caggtcttcc gctttaaaca   104460
tttcaacatt gacatgattt ggctgtgtcc ccacccaaat ctcatcttgt agttccctta   104520
atctccatgt gtcatgggag ggaccaggta gaggtaattg aattatgggg gcggtttccc   104580
ccatgctgtt ctcatgatag tgagttctca ttagatctga tcattttata aggggcttcc   104640 cccttttgctg ggcactgatt cttccttgctg ccaccatgtg aagaaagaca tgtttgcgtc   104700
cccttccacc atgattgtaa gtttcctgag gcctccgcag ccctgcggaa ctgtgagtca   104760
atgaaacctc tttatttttat ctattaccca gtctcaggta tgtctttatt agcagtgtga   104820
gaatggatta atacaaacat taactttatt tttcaacaag attctaaggc ttaaggtgtg   104880
caaaataaaa cttgtaacta agaagggagc tgtggctttg tttatagctt gagattgaat   104940
ccgggtgcaa ataatttgag aagttttttgc cttcaaggtg gaaaatgaac ttctatactt   105000
aatcctgaat tcaggcacat aaattaggtc catgacatga gatttgcatt ttttttacccc   105060 atggtaggta cccatcgcct gtgaagatca cactgaggcc aagctgagaa accagtgatc   105120
tctggagaaa aatattttttc tctcattttta ctttttctctg gttatcaag tatttagtta   105180 ctgcctgttg tgtcaggcat tgatctagga gggctagaga taaacagtga acacagcagg   105240
```

```
taaaaaagca tccttgccca cgtggagctt acttgtattt tagtgtgtgg acatacagag   105300
taagcgggaa cctcacaatt aataagttat ataatgtatt cacagatgat aagtgtgacg   105360
gaacaaaaat tgatcagggt gggagggatg gggagtaggg gccaggctgg ttgcagttgt   105420
gcatagggca ggccggtagt gctcaggaa caatggacac ctaggagcac aggcttgtg    105480
gaggtcaggg atggggccac gtggccgtca gggggcaaag ccttctaggc tgagggaaca   105540
atcacatgtg ccccgatgtg gcctgttttt cggcaggtgt gcctggaagg gcaagggaag   105600
agcagagcag tgagaggtga ggcccagagg aagtgtgagg ccagatcagg ctgacctcaa   105660
agaccattgt gaggtccatt tattggaggg aaggagaag ccgttgcaga gaaggaggag   105720
cagggaagta gtgacatgat ctgacgagtg attggtaagg atcactgagt gttgctgaaa   105780
atggactgaa ggaggcagtg gtgcaacaga ggctttgccg tcacccaggc gagaggtgag   105840
ggggtggagt ctgcttgggg tggtggcagt ggcagtagag ccaacagagc tcgcccagag   105900
actggaagga gagggatcag aggtgacccc caggttttgg cgtgagcatc cagaaagttg   105960
gagtttccat cagttaaaat aggaagatgg gtgtggagca gctttgggga acgatgagga   106020
attggtttgg gaactccttg tgtttaactt ctgttcatgt tgaatatttc acctgcttcc   106080
aaaaccgttt tgaaatgaaa actcatctat aaaattccat aagaggtatc aaaattagca   106140
acagaaagag aaaggggga aattttaaaa ggcatattgg tctttcctct agattggatg   106200
gtgttgggaa gcgggagtta ctcaatgatt gggaatctta ataatcttac ctagaagatg   106260
ctctaaatgg taaatgaatt tacaatgaaa acgttatcta taaaattcca ttaaattcat   106320
caaaattagc aacataaaga gaagggagg aactttgagt gacacattac ccctttaaag   106380
atgtccactc atagtgtaag gcaaacacat atttgtttat aggagaataa atcaataggc   106440
tttgaaatgc aaattgtagc acatcagttc ctttcatttc agacaattta gttctgatct   106500
gttgtacctt ataaatttat ttctgcccta ccatactcag ctatgattat ttataaatta   106560
tccaatctca tataaatcca tttatctgtt atccttctt gcatatggct gttaacatct   106620
ttaacatgtc gtgggaaaat gtgacaaagt tcaaattatc ccattttgtt acttgttggt   106680
agctctggag aaggttattt ggaaaaaagc acatgaaatt gttaacaaaa ttattgtgta   106740
tcttctgtta ggagccctgg ccagctgccc tggggagtga gcaggtgcta ttccacagtt   106800
tctagagtgg caggatgccc cctccttcca gaagtctccc agtgggcttg tgccaaatct   106860
ggacttccca gtgaagcact tggaaactgc cgaatgaaag gacatgtgat cctccacatt   106920
ttaacattt tctttccaaa cactagttat tttctcctaa attgccattt gtgaatctaa   106980
ttctgtcttt catgtttcag ttgatgaatg gccatgccat tctttttgtga agtttaggca   107040
tcttcgcata gcagtattag caacattatt tgaacattta ttgaattttg tcattattat   107100
tttatacaaa tgattgagga aaaatggggg ctgaaaatgt tgataagaag cctagctttt   107160
ctaagcttaa ttacccatga ccccgaaatg ccagtcaccg catgtgtcca gccagcaaga   107220
cattagctcc atatggatgt tctttgacct tgaatgtatt ggtctgttct tatgctgcta   107280
atacagacat acccgagact gagtaattta taaagaaag aggtttaatt gactcacagt   107340
tctgcagggc tggggaggcc tcagaaaact tacaatcatg gtggaagg aagcaaacat    107400
gtccttcttc acatggcggc ggcaagcaga agggccgacc aaaaggggga aagcccttg    107460
tgaaaccatc agatctcgtt tgaactcgct gtcaccagaa cagcatggaa gtaaccatgc   107520
ccaaggttaa attacctccc accgggtccc tcccaggaca ggtggggatt atgggaacta   107580
caattcaaga tgagctttgg gtgggaacac agccaaacca tatcactgag caagtcagta   107640
```

```
tgtgttcact ggggaaagag gagaaaatta atacatgtgc taggtctact taaaaggtgc   107700
agcacaaata gaagttttat catttttttgg gatctctggg agtagaagtt cacagaacct   107760
gaatactcac ctttcatgct tctcttttac aattgtagtc tgtgagaagt gtggggctgc   107820
ttgcatgtca cactggcgga atcttgggct cttcctcttt tgaactctga aggcattttg   107880
tctgtatggc tgatatgaaa gttgccttgc aatatcgctc actgtgtgcc tgtcctaatt   107940
aacctactac tgacaatccc ttgaaaacag ggactttgaa gagtgtaaag gatgtttcag   108000
acacagcagc cagcacaatt cttgataaaa atagcaggca ttgagtaaat agctattgag   108060
tgaaaggaag gttgttagaa atctcttaat gaggccgggc gtggtggctc acgcctgtaa   108120
tcccagcact ttgggaagcc gaggcgggtg gatcacctga ggtcaggagt tcgagaccag   108180
cctcaccaac atggagaaac cccatcttta ctaaaaatac aaaattagcc aggcatggtg   108240
gcgtatgcct gtaatcccag ctactcggaa ggctgaggca ggggaatcac ttgaacccgg   108300
gaggcagagg ttgtggtgag ccgagatcgt gccactgcac tccagcctag acaacaagag   108360
caaacaagag caaatctcaa aaaaaaaaaa aaaaaaaaa aatctcttaa tgaaagttaa   108420
ggcaacgttc ttaagaatga attatggggg ataaaaggaa tccttggaac acatcttgag   108480
gcttccatga tttcttcttt ataaatctga tgcaagggaa tggtgccgag actttcttga   108540
gccgaggtct ccatcagtgg cacatgtgtg gagggcaccc tgggatggcc catgctgtg   108600 gtggtggaga accacatgcc ccagctctgg agtcctactg catatcctgg gagtccacgg   108660
agcctagctg ctggctcacg tctgtgctgc tctgcaattt taatgggcta attggtgccc   108720
atgacagtta atttgccagc taaaccaaaa ccacaactaa aaaaggacag taacttcttt   108780
attttttttt tttaattaca aaaaaagttt ttaagacaga gtctcgcttt gtcacccagg   108840
caaatggtgc gatctcggtt cactgcaacc tctgcctccc aggttcaagc gattctcctg   108900
cctcagcctc ctgagtagct gggactacag gcacaaacca ccacacccag atgattttg   108960 tatttttttaa atagagacag ggtttcacca tgttggccag gctggtctcg aactcctgac   109020
ctcaggtgat ctgcctacct cggcctccca aagtgctggg attacaggtg tgagccaccg   109080
tgcccagcct gagaacagta acttctatat caccagtata ggccaatagt gacagtgagt   109140
tgtgttttaa tttggggata gtaacatttg taaaagacta tgggtctcaa ataaggtctc   109200
aaatggattc tagttcctgg cttttttcgtc tgtgaccatg ggcaggttac tataactatt   109260
ttcttgactc ttaaaacaag ggatgaggca aaatagttta aaatttttc cttctctctc   109320 tgaaattctt gtatttaacg tgattgaagt gacaatataa gaactacagg agtgtacatt   109380
tcctccaaaa ttttatgaag cgaaaaaagc aaagtaatgg atcaaacatt ccatttggt    109440 tttgcagcca gtcccattcc ctccttaaat agagtcaggt cttgactgcg gtagagaacg   109500
tgtttgttaa ggcttcctaa taatagcagg ctgtctcaat ataaagttca caagaaacct   109560
taaaaacatg aattatccct cacatcaccc tgatggagca gagatgtgtt attatcatt   109620 tactttcaca gctgggtaaa tcaaggtata gagacacatc aagcctctgg tagcttggac   109680
aaggtcatag tcagtggcac acacagatag aactgtgtct tcctgttttt ccttccatgt   109740
agggaaaaat gtctggattt taactgcttt ttttttccttt taaagattta tctattaata   109800
tacatagagt aaaacccagt tataatttgc cttgcagtaa agcaaattta gatgtgatcg   109860
gattgctgat agtccttgtc ttctcatctg gattcttatc tgagggttgg gactgatgat   109920
cagaaaggtc ttgtgatcat ctggggcttt tcagttcag ggaaaggtca gttatttaca   109980
gtcatagctt cgctatctat tcttgttcct ttttttgatgg ttcatacaga ttttcattaa   110040
```

```
ccttgcaatc atgtggccat atatttcctg tgatttgttt ctttggaacc ctcttatggt   110100
ggagttttgc tgttaattct aatttctctc ctgtaatatc taccctgact tccttatctt   110160 cttttttaaaa aattgaatag aattaacata ctatacaatt taccttttac agtgtaccat  110220
tcagtggttt ttagtatatt cacaaaattg tgcaaccatc actaccgtct aattccacaa   110280
tatttttatt ccctcaaaaa agaaacctga cacccatcag aagtcactct tcaaggccag   110340
ggtcagtccc tcacgcctgt aatcccagca ctttgggagg ctgaggtggg cggatcacaa   110400
ggtcaagaga tcgagaccat cctggccaat gtggtgaaac cctgtctcta ctaaaaatat   110460
aaaaattagc tgggcatggt ggcgcacacc tgttgtctca gctacttggg aggctgaggc   110520
aggagaatca cttgaaccca ggaggcagag gttgcattga gccaagatcg tgccactgca   110580
caccagcctg gtgacagagc gagactctgt ctcaaaaata aaataaaata aataaacaat   110640
aaataaataa aaataaaaaa agaagtcact ccttatcctc cacgctccaa ccccgctcc   110700 tggcaactat gaatctactt tctgtttcta tggatttgcc tattctgggc atttcatata   110760
aaaatgaaaa tacaatgtgt aacctgtcat gtctggctcc tttcacttag cataatgttt   110820
tcaaggttca tccatgttgt agtatgaatc aattcttcat tccttttat ggctgaataa    110880 tattcaattt cgccttcttt taatccaaga gaaccgtagc acttactgaa aagtgtcctc   110940
aaattttctt ttttccgtag aaactttctc taatagaatc tcatgtgtac ttttgtctag  111000
gtttcttctc aaagtcttta aatagaactc cagctaagta gttcctaagg gctttgaact   111060
taaattcaac tttattaaaa ttcttggagt gtttgaagta cggtattgtc tgttacatgc   111120
ctgaaggtaa gtaagtgtgg cattggggtg tcctcccagt actagtgggt gtccgtttcc   111180
ttgcagtgcc aagaccttgg ctgaagatct ctctcgtcat tgactgtgta tttttcactg   111240
gggctcataa aaccccatgg gaggctctgc accttctttc tttgggttaa gcacgctgcc   111300
tcagtcactg ccatagcctg cctggcgaag gaagatatgg gtacatctaa acgctctttt   111360
tcgttgttct aagaaggagt attgcagtca gtgtggaggt ggctggcagc acctttctac   111420
tgtgagaaca tctgccatgt tcctttatgt attttttccc actctaagga catttatcac   111480
aagacaattg aaacagatcc tggcagcctg ctattaagaa acatttacta ccagcattta   111540
ctttactgct ctctgtttat tgccggtgtt agcttgcatt gtcaaaaaca tcaccaattg   111600
gaatgtgacc tcaggttaaa tggacttgga agatttatga atctttctag cacagtattt   111660
gtgctataat agaatttatt tctttgcaag cttaacaata acattcagac tgctgctttg   111720
aatttccctg acatgagtca taacaataaa aaaaatgca aagtcccaga tatggtcaga    111780
agagaagact gattttttatc tatattaaga gtaggtaata ataaatggtg atctctttgt  111840
taatggtgca gtttgggact tgactcacct ttgaatgtgg tcaactcaag agttacttt    111900 tttttcccctc tcagttattt ctattatttc atttaaatgc tttgttttca ttctctttca  111960
ctgactgatg atcagaaata tttgcctgga tggcacagta cagctaatgt cattagtgaa   112020
aggtggcaca aaccactgca ttttaaagta aaagtatgag taaaattttg gacaatctgt   112080
gttacttaaa aatatgcatt gctatacaaa gtttacaaat ttaaatttat ttagaagaaa   112140
ttgttttaaa agcaaggtct cactctgtcg cctaggctgg agtgcaatgg cacaatcaca   112200
agccactgca gcctctacct cctgggctca agtgatcctc ctgcctcagc ctcctgagtg  112260
gctgggacta caggtgtgca ccaccatacc tggataactt ttttttttt tttttttaat   112320 agagatggag tctttccatg ttgcccaggc tggtcttgtg aactcctgac cgcaagcaat   112380
cctcctgcct tggcctccca aagttctcgg attataggca tgaatcacct cactggccac   112440
```

```
aaagttaaat ttaaaaggag agattctggc tgggtgccat agctcacgcc tgtaatccca   112500
gcactttggg aggctgaggt gggtggatca ctcgaggtta ggagtttgag accatcctgg   112560
ccaacatggc aaaaccccat ctctactaaa aatacaaaaa aaaaaaaaaa aaaaattagc   112620
cggatgtggt ggcatgcacc catagttcca gctactcagg aggctgaggc acgagaatta   112680
cacctgggag gcggaggtcg cagtgagctg agttcacgcc actgcactcc agcctgggtg   112740
acagagcaaa actctgtctc aaaaaaaaaa aaaaaaaaaa aagagaaaga tttgcaaaga   112800
ttttctttgc aaatgttcaa tgtgctgttt gtactgtgag aactggctgt gagcattaat   112860
gcagagtttt gtaatagtgg gtgaagcttg aagaattgaa aaaagtctt aatttctat    112920 ttacataatg ctattatgcc taggctggca gctttgattt acccaaattt taatcttttc   112980
ttaaaattac atttgtactt tttttaaaaa acaaaagata cataaaatga aggaattgaa   113040
tagggtgatt tctgagtttc ttttctgatc taaaattctt tgattctcta cgagtttttc   113100
atttatggaa ttgcatagca taaattctga gaaactgaat agggaaactg agtaaatcaa   113160
atagattaat agcataattc aaataaagta cgttattttt tctggatgtc agtagatagt   113220
agaatgtaag tattaaatgt cagagacgtg taactctaat gccaaagtgg attatgtagt   113280
tgaaaactta attaaaccat ttattattca cttgtaacta ctttgacatt attttttaga   113340 ttttttttcag tcttagaaaa ttattcttct gtagttttca catcagaagg ggtttctaag   113400
gattaatgat ttaatcaact aaaaacattt tttgagcctg agatgagagt cccactgaaa   113460
tacacttcat tgttatttgg ctgctatatt tttaattgct ttagtgagta tattttatct   113520
ttctttggga agtgagggaa actaatactc agagggtgca aaatgctatg ggttggatgc   113580
attttgcatc ctctgatgcc acttgattct cttagaggta aagttgaggt cctggccacg   113640
gggaggggca gaggcaattc tcagaggtgg tggcgctgac caccaggtga cattttggaa   113700
gtttgtgttt ctgttttttgg tcatcataat gattccaggg atggtgacgt ttggtagttg   113760
ggacatggtt gctggacatc cggcagtgat cacgttaatc ccatacattg cacattgttc   113820
gactggacct taatggaggt taaaaaacat gcatataatt atctgagcta ggaattacct   113880
cgattttaca aagaaatgca aattattttt tccccacagc tataggtact tggaattttc   113940
tgggaagatg gcaacccaat aaataaagga agtacatcct ttgttttgct cagaactttg   114000
ccaagagttt tgtcattttg gaaaatcatg tccctgatgg tcataccacc aagacacact   114060
ggcattggtc tctggtgaag cttgggacaa ggcctgtaga gccagtggct gacagcttcc   114120
tcacggcttc tggagaggtt ctggtgccat ttacatatgg agtataattc aaacaaagta   114180
ttcaaaccat agttttttaat tataaattac tttccgttta ttttctttt tgtcttattt    114240 ttagggtagt atattgcttt tggagaaact atgaaggtag attatattaa gaatgatttt   114300
tatttcagga tagtaaaagt atatattatc aaaaaggacc ctttggatat gagagtatta   114360
aaaatcaatg tactataata tatgctttga agcatgaaaa acatatttta aaacaatttt   114420
tcattctcat gcccgatact tttagtctat ttcaaatgaa tcctcagtcc gcatattgaa   114480
gcacggcttt ttccgatgcg gtgactgctg tcttagttca ttcgtgctcc tgtaaagaat   114540
agcacacact gggtaatttt aaaacaaatt tacaggctca gagtcctaga ggctgggaag   114600
tccagtgtca aggtgccatt aggttttggtg attctgattc caggatggca ccttgaacgc   114660
tgcgtcctca ttgtggctga aggtggaagg gtaaacagtg gaagagaaca gagccactcc   114720
tgagagccct ttttatcata gcattaatat tcatgagtca tgggtagagc cctcatgacc   114780
taaacacctc ccagtaagtc tacctcccaa caccattgca ttgagaatta agtttccaac   114840
```

```
atgtgaattc tgggggatac attcaaacta tagcaactac cattattaat ttctaaaaaa    114900
aaaaaaaaaa aaaaaaaaaa aaaaaaaaaa aagtcatctt gtacctttgt acctaagaag    114960
agaaaacaaa tgttctcctg tcactttgca tttcttgttt ttggctatgg attaatatca    115020
tgttgaaatt ttaaatttaa tttctcttta attgctgttc cggagaactg ggaggcact    115080 ctcagacttt ggggtggagt ggttcttaga tcactttttc taggaaccag ttgtctgtcc    115140
tcaggaggcc ccatcctggc tgctggaaag cagggaaac tcttccctac ctgtccttac    115200
aatcaggagc tgcctggtgt ctccagggtc tgctggcggc cacctggtgg gtgtccaggg    115260
actacaaaga actttcttgc ctagtctctt gctgcctggt tgagtaggga ggaggctgcc    115320
agcaagactg ggattatggg atggcatcag ccagatgaac catacgtagc tgcctgagga    115380
gagtcaggct tccttaggat taagctgcag gtgggatgct ggcagggaca ccaccacgca    115440
cgccaggcct tctcccaagc tttccattgc tgcccgtttc caagaattcc cccttgagcc    115500
tatcacagtg agcacctaga tctattggtg ctttctgggc aacaggaaaa agaaatggca    115560
aaacccacac gtttgcatat taactgtgct aggttggatt tggaaatgat gtaactgtac    115620
attttgaatt cagattacga gctgtgtggg tgagacaacc ttaacttcaa tatttcctga    115680
tatttctgtt tttaagttgg tacccaggat gtcccttaa caaatgtttt gcccttcgt    115740 tgtaaaggat ctggggttgc cagtgacttg gctgacagtg gtgctaatgg gccaggtact    115800
gacgcacagt tcaggaggaa gctgaatgac caggtgtctc aaacctaaag ccagatgtgt    115860
tccccagttg tctgtaagga gctataggct gtgcggaagt gtagggaggc aggcattttc    115920
cgtggtagcc tgcctggact gtcatccttg tccacagcat ggttttttg ttgttttgag    115980 atggaatctc gctctgtcgc ccaggctgga gtgcagtggt gtgatctcag ctcactgcaa    116040
cctccacctc ccgggttcaa gtgattctcc tgcctcagcc tggggtacag gcacccacca    116100
ccaggcccgg ctaatttttt gtattttag tagagatggg gtttcaccat gttagccagg    116160
atggtctcga tctcctgacc tcgtgatctg cccccctcag cctcctaaag tgctgggatt    116220
acaggtgtga accactgtgc ccagcccaca gcatgttgat taaaggagag agatggccga    116280
gcctggtctc gtgattgctc tggccgtggc accttgtact tggtggatgc acagtgtctg    116340
gcacccatgg gaattaaggg taaataaatt aaatgacaca tccaaattga ggggaccaga    116400
ctgtaacttg ggacattgca gctctgctgg ctcaactgct gagtagaagc tcttgttggc    116460
tgtgctaaat gttagatttt ttcaaattgc tagacctctg ccccaaactg ttaatttcca    116520
cgagaaatgt gatgagaaag acaaagggt atattaacca gatacaaata gataactctt    116580
gacttgaatt tataattgat ttgcagtcat attggccaga ggcttttct ggagtgagtc    116640 tgaacatctg tactgtgcaa tgctgagttc agggtgggca ggaagcaagt gcttattact    116700
ctctgataag gacaaagaac ccctaaaaca tgttgcactg tatatgtcct gatgaggctc    116760
ttccaggtgg gaagccagat tttcgcctgg gaggggcagg atatacttac tcccttagc    116820 agctggtgct caggatgtgg gcagaatata aggggctat gtataggcat ttggcaccca    116880
ggacaggatg cctgttttcaa acagctttgt aaataagcat tcggattta ccagcctcca    116940 ctctttttaa agccagtctt ctattcttcc agaatgtact tttatctcat gtctcttcta    117000
taaagagcac taagggcacc ctccttttac ggggatacag gtcctggtga aattggaggc    117060
tcccagagct ggggatggca gctgtggaca ctgtccagct cggattctcc tgtgctccgt    117120
catgtccagg acagtgttgg cacattgctg gtggctgcag ggactctgta tgcacagatg    117180
cattccacct gggggaaact tgggcagtag aacaccgctg agatttcctg tcttggcgga    117240
```

```
tctcaggaac tgtccacagc tgccttctct tctcagatcc ccagggccag cctcagtggg   117300
agctggttcc tttgggccat cctatccaag cctgtgcctc agagaaaatc cggtggcacc   117360
caaagtttcc ttgaagttaa ggggctctag ggggcctaag ggagcctcac tgattcaaag   117420
ctaagccttt atcctggagt gagcagggtt ctgacaggaa ggggtcagta ttctcttacc   117480
aggtacacgt tgccccctttc ctcatgctta cctgaaacga atctcttctt ccctaagtga   117540
atgagtacct ccttgtctct tttataagaa gcgaacagtg gttcggggag ttttcagtgt   117600
ttaagttcca aaatctttga agagattgac tcagatgact caggattcac ttggcacccg   117660
cttttgacat cagccatgct atattttcac tagcatccat ctggcatctt gggctccaaa   117720
gctccttatg cccttgccac agctgagttc ttggtgggac tcaaggtctt gttcatcttt   117780
gtatccctag tacttagaac atgcctgatg tacagcaggg gctgtgaaat ccccatcatc   117840
agtgaatgtg catgtggatc atatgtccta tttcctgtac ttgatgtaac tctttggaaa   117900
taccaagtct tcttatttac aaggtaaagg cagcactaat gcaaatttga ttctgtaacc   117960
taggtaatgc acttttacat tgtatggctt ctgtgacatg actcttttt gacggcctta    118020 tacttctttt taaattctct atgaaaagaa aggtacctct cttgagaatc accccctcct   118080
gtacccttat gcactgatgt ttccatggtt ctctcctcgg tcctcttgat gtcatccacc   118140
cccttggctt cactgctatg gagtgatagt ctgatgactt ccaaatccat gtctctgtga   118200
aggcctttct gggctttgga ctctggactc cccgaccact gaaaatctcc cactgcatgg   118260
cccacatgtg tctcagactc agcattgcag aagctaagct tgttatcccc acttctcccc   118320
ttgccgcatt ccccatctac ccagtcacct aggacataga aaccaggcgt ctccctcgat   118380
gcctctcttt tctgtatctt cttatattta ataagtgaca aagaggggac ccgtagaatc   118440
tacctcctca aatgctcaac catcccttt ttctgttgct ctcttctgtg atcttctggt    118500
ccttacacct tgtacctgtg atgtcactgt gactttcttg tcctccatcc atccgtccat   118560
cgaggacact cttccatctc tgccccactc tgtgcagcca cactcggcaa gttccctgat   118620
ggtgcccggc tcctcctagc attggccttt actcaggaca cttccagtcc tggaatcccc   118680
tctccccgct gcccacccg ccttgtcatc ttcagcttga aagtcaaata aatattcctt    118740
cgacataaag gctttgctca agtgtctgct ctcctttgaa gtgttttaag ggcccaggga   118800
gaattaactt gcttcctgag tgtccccact cagcagcctg tgggctttcc tcatatcatc   118860 tgtgacccttg gttgcactc atctctctgc ctccccctcc ctcaccaact gcctctcccc    118920
agattagaag cagcccgcga gagcatttca ctccttttg catccccagc tcctagcacc    118980
gtgcctggaa aacagctgct actcaagaag tatgtgttga gcgcatgaac ggggagatac   119040
acttaggctg gatacagtag gattgagggc tgctgttctt ttgtgactta cctagattgg   119100
tctcccttaa gccaaggtat acacatcaga gaaaggaggc agtcttaaag gacagcagtg   119160
ggtcacttgt ggttgagggt ctcatcttac ttcccgtgca gttagcttgt tggtgagggg   119220
actgcctctg tgttgtggca ttaggggact agaggaggca ggcccaagtc tgcttgcttg   119280
tcatggctac tcaaaatttc cccagggacc cttcatgcct ttcgggtcag cactgccttc   119340
cctaggctaa gttaactctg caaccaacaa cagtgaggta tgaccgagat tatctgtctg   119400
gtccttacct ggatgagatt agggtgtcgg aagaggtaat ggaagaaaaa aattggagct   119460
gcagaattct gtagatcatt atatgttttc cggaggcctt cccctatctt agaagtgagt   119520
gcctgtgtag tggttggtaa tatcagcatg aaccagctac tggcattctt gtctcccagc   119580
tgtcccaacc tccaggggtt cccctagctt ctaaaggttc tccagaaacc atcttccctg   119640
```

```
cccccatcat gctgggcagt ttctttgttt gcaagtctat ccaagcctct tgggcctaga    119700
tcagctcaga ttgatttctt gttgtaccta actgggatca gaaaccatct ggtttcacct    119760
agttgagggg acattctatc aaatacaaga attacaatga aaacttgtgt tatgttttga    119820
tagaggctgg tctttctgtc tctattggag aagagtgctg aggatgggat gtgtgcttcc    119880
agttgtaggc tggaaaacta tgtgttctac ttatttcata ttatttaaat tttttaatgt    119940
tttaattttt aatttactta aattttaaat tttcattttt attattttta tattttaatt    120000 attacccccct cccccttcctt ccccctcctct ttcttttttct ttccttttctt gatagggtct    120060 cattctgtca tccaggctgg attgcagtgg cacgattact gctcactgcc gcctcaaact    120120
cctgggctca agccatcctc ctgcctcagc cgtccaagta gctgggatta tagccgcata    120180
ccaccatgcc tgattgtgtg tgtgttttttt ttttcaatt tctcgtagag acactatgta    120240
gtctcactat gttgcccagg gtggtctcga actcctggtc ttaagtgatt ctctcgcctt    120300
ggcctcccac aggcctgaga ttacgggcat gagccaccac acctggccca tattatttct    120360
tagcctttac tctggaagtt aataagggtt tactgatcct cttgggactt tcaagttagg    120420
atgaaattgt ggttgatgcc agcacaagaa acatgcttgt aaatgagcaa gttgtagatt    120480
ggaataagta taatattcca tcattggttt ccaagattcc ctggtaattt tgccttcact    120540
tagccaaaaa cagggaaata ccaacaaagt tgttgctgtt tgattgtagg tccaaataaa    120600
ttagttaaga ccagagctta ggggagcata gttcacacaa caacgagaag agtgacaagg    120660
tatttaggtc attattttga ttggtctctt tcgaccaaaa caggcagatg ttgccttttc    120720
aattagcaag accctagatc tgtttcagaa gcccatctgt atgcgtaatt gtaacctcag    120780
tgtcattcag gactgctctg tactgcctcc taggttgttt tcttctttcc tttctccatg    120840
tgagccttta aaccgggtgt tattattctc tgcaaatggc caaactcata tatgtttttg    120900
tcatttttta tgcagatttc agcaacgtcc ctgatatcac aacaggtctg aaaaggagtc    120960
agacagatgg cactctggat caggtttccc acagggagaa aatggagcag acattcaggg    121020
taagatactg gcccaaatcg caaaccaaga accaggcagg cgagtgttag ttcccacctt    121080
tacctaaggt ggggaaagga gatggagtta cctatctcta ggtccagcag ttgatacaaa    121140
catacatata tatgttaagg atacagcttc cttatttatg tatttttttg aagtgaagta    121200
ctactaatcg gaaccatttg ctctagccag aactcctcca tgacttctgg tatgccatca    121260
aagagcagtg cacactctgc tgttcatata ttgtgctggc tttgcttagc aattttgaca    121320
aggaaaacct tgtcaaaagg tgttaattac taatctcttt cttcttact ttttttttttt    121380 tggctgaaga taaattattt ttggaatgtt gtcatttttgt gtgataaaac gtatataaca    121440
taaaatatgc ctttttttact attttcaagt gtatgcctct ctgtggcatt aagtatattc    121500
acattggttt gcaaccacca ccaccatcta gaacttttttc atcattccag acagaaactc    121560
tgtaccccct aaacaataac tctctatttc ccctgctttc aactccctca taacttctat    121620
tccactttct gtctcatttg ccaatttcta ggtgccccat atattggtgg aatcacaata    121680
tttgtccttt tgtttctggc ttatttcact taacatatgt cttctgggtt aatccaggtt    121740
gtggcatgtg tcagactttc attctttttt atggctgagt aatattccat tatacggata    121800
caccacattt tgtttattca ttcatctgtt gatagacact tggattattg ctgctgttgt    121860
ggataatgct ggagtgaatg ttggtgtaag agttatctgc gtgaatcctt gttttcaggc    121920
caaggagtgg aattgccagg tcatgtggtg attctctgtt tagcttttg aggaacagcc    121980 catggtctcc cacaatgctg cactatttga cattcccagc ggcaatgcag gaggcttcta    122040
```

```
cttcatccac atccttggca gcatttgtta cattccattc ctttcctgca ttttttaactg   122100 tttgttgtca gctacccttt cagaaatggt ctgattgaca taatctgtgt taatatccag   122160
tccagtttta atcgattttg aaattataag tcttctgtat ttgttttttgt cttaaataca   122220 aaataagaat ggaagaaata gaagcaatga taggcattta aatgaaagtt ataaagtgga   122280
acgatggctc ggttgggttt agactaacac tatcacaaga ttcttggggt atcacttcac   122340
cagccggaaa cctctgtggc caagggtgct tttgcccaag ttttgctcgg gcccactagg   122400
cccactcggc ccactcgacc tggcaggctg tgctcaactt gcactactgg cctgcatccc   122460
atgcctgcca agagtgagca gagtggtgag ggtgtgtca gtgagcgcag tggtgaaggg   122520
tgtgtcagtg agcacgtgtg gggtctggcc accacacaca ggcaggaatg ctggctgtgg   122580
tggggcaggc agcagctgca ggctctagca cgggcgccgg ttccctgtga agctacggct   122640
ggatcacaca tattacaagc agtttccatg gcctgcatca gtacctggaa gcttggagat   122700
gccaggaacc gctgagcccc aaagagggtg gcatagccct ggttctggga actcctaggt   122760
ctgggctccc tgaagggctg cagctcttct ctcctcctct tttctctcct tgtcacctgt   122820
aatgtggcga gcaaggggcg tgttttggcc ctgtttgtgt tgtagctctt tcagccctgc   122880
cgttaggcag gtcccgaatt cttgtcccat gaccaggaag aaggaggtat gcgggcaagg   122940
ggagggtgag caaggtgaag aggagcttta ttgagctgta gaacagctca gaggaaaccc   123000
acagtgggta gcttctctct gcaggctggt tgtcccatag agtgttcacc tctcagcaga   123060
gagcagaccc tggagtgggt agctcctctc cacagctggt agtactaatg tctgcttagc   123120
tttaagcaga gaggagaccc tggagtagct cctctcctca gctggttgtc tcattgtctc   123180
tttgagtctg gctgagtcca gggctcgagg gggtggaaat gtgcactgat tggtccatag   123240
tggccatgag cagacccaga aaaagctcca taagttccca ctctggtctg tgggactggc   123300
agcccagccc ccagacttca ggccttcccc ggcttgaaag tggggctttt ctggggaccc   123360 actccttttcc acccaggagc ctgtctgcgt cctgccactc ttcctggtgc ccaggctgtt   123420
tgtgccaaag ggtgcctgca ggccagggcc gagctgccct cagtcccctc cttggcctgc   123480
ctcccatgct cattggtgcc caaagtacag caggggggctg gcatgtcagc gctgcccctga   123540 acgtgtccac acatggctgg gttgcagcag tgcctgggct tggactcaac tttgctccaa   123600
gagcagagcg ggcaccagga gtagggagaa accaggcagt gggagcaggc tactttcgag   123660
cctgtggggg caatgggtcc ttcctaggcc cctgagagtg cagagatgtc tgggtccaca   123720
gtcgcggcta cgtggctgca gcagtacccg ggagggcggg gctccttcct gctcctggcc   123780
cccaagaaca cagggatgtc tgggtcagaa gccacggctg ggcagtcaca gctgtgcccg   123840
aggagcacga ggctcccgcc ctgccacttc aggattgggt ggggcttcca cattctcagc   123900
tcctgctggc tccatggaac gcacagcgct ggccgtgcct cccccggtgc agccggcatc   123960
atcgcagtga ctgttccaga tgggccaccg ctgccatcaa gaccaccagg agccaggcac   124020
atggcacatc ctttggagga accatgtggc atacctttttg ggggttggtg acatcccctg   124080
tgtgtgaggg accaggttag agcctgccag cttcagaacg gatgcttctg gttccgaagc   124140
agctggtttg atgaagcagc tatgggctct cagcctcccc tctcttctcc ctttcacttc   124200
ctcactacct gctctcttct cccgtttttcc atgcaccttc ttccaaattt ctcctccctc   124260
tcctcctcat tcctcatgca aagcaaatgc tcagctgcct tcgctggcct ggttatgtcc   124320
caggatgcaa gttattttac aaaactgaaa ttcatcagca tttttagtcc ttctactttg   124380
ttctatctct agtgggttat ttaattttgg gaacccaata tcatatctaa tgttcattag   124440
```

```
cttttttaatg aagcagtgga tcctagagca tcaaatagat gtgttttgat agccttgtct  124500
taaattattt ttaaatctta ttttaataat acaatagata tggggtctca ctatgttgct  124560
gaggctggtc tcaaactcct gggctcaaga gatcctactg ccccggcctc ctgaagtact  124620
ggaattacag gtgtgagtca ctgtgcctgg cctgacttaa aatttttag aaaatcaaat  124680 cctcctgaaa cactgataga gcaaggccat gtatttaaaa gttaagtgtg cctgtggggg  124740
ccctggcaca ggatggtagc ttgggggact ctcacttaac accgtgaggg ataacgactt  124800
ctcgtctctt atgatctgct tgagttacac atcagagctc ttaagaagga aattgaattt  124860
tttcccaaag tttatcttaa gattcagcaa aatagatatg caaaaagtta gcacgttaag  124920
gccattgcca actctgttat ttaacaatgc ctatggtaac taagcaaaac atttacaaag  124980
tgaacattgg agcatcagaa atttagaaga ggagagaaag ctgcaatcag gttgaaattg  125040
gggccgtctg agcttcaatt ttcattgtta aaagtggaga aaggagaaag caaataataa  125100
catcaacgaa cacagaagaa aaatttttat tgaaagaata tgagcatgtt aagcatttgc  125160
tgtaaaatcc ctctcaagtc taacgtagtt atcaccttac cttttttaaga tatgaagatt  125220 tccatgtata atgatagatt tcagtgcatt ttttaaaatc tttggtaaat acctagcagt  125280
tactcagttt ccctgttctt tgtttcttgg gaaagaagaa tcagtggcca ccaaaagtaa  125340
aaactgtggt ggacattagt gaaaagaaaa agaaaatttc aaatttaagg atcacatttt  125400
tttttctgtt ccgtggtttt tttaaaaaaa aattttaaat tttttttttt tttttggaaa  125460
catcgtgtta tatctaaagc aatcctcttc tggatttttt tttattgtt ttaaattttg  125520 ttttatttta ttttttttgag acaagttctc accctgttgt gcagcctgga gtgcagtggt  125580
gtgatctcga ctcactgctg ccttgacctc ctgggctcaa atgatcctcc cacctcagcc  125640
tcctaagtag ctgggaccac aggtgcctgc caccatgccc ggataatttt gtttattttt  125700
tgtagagact aggtctcact gtgttgccca gtctggtctc aaactcctgg gctggagcaa  125760
tactcccgcc tcagcctccc aatgtgctgg gattacaggt gtgagtcacc gtacccagtc  125820
ctcttctatt tttgaagtgg tgatgtggga ggtgtctggt gaatgcctag tgtgtgctgg  125880
gagtggattt tttgggactc cccccgcccc accccctgtg ccatgtcctc agaaggtggt  125940
ctcttctcag ggagaagatc tgcctctgtt ttctgggctt cctgcctag cccaactggt  126000 cttctcaggg gtcattaact tcttttcaga ttagaccctg gttgaacctg gctgttggg  126060 gatattttac taacaactat tctagacatt agaataaaga ataatttccc ttgaaaatca  126120
aatgaagcct ggtttgatga agcacagctg tacccagggc ttttgacagc cccgcaattt  126180
ctgcaaatgg ttcctaattg attggcttct tctctgtaag ggtgcctatt actgtcatag  126240
ctctttgtgt gaccctgtca gcctctcctg taggggggga tttttttccc cagtattgtt  126300
agcaattagc atgtgctatt gtaatagttt ggagtttgaa agaaatatac aatgtccctt  126360
tgggtgagga ggttgaaaga gtttttggtt tgttctggga acttaaggta tattaagcag  126420
tccccacaga catgctgcct gcactccacc tgctgagctg gctctgaggc tcaggagacg  126480
tggccctctg tggtcccatt gtctccacgt ctgtggtaac ccggtgcctt tctagagcag  126540
gcaggctccc ggcatgggtg gaaacagagc aggggggccag cttcccccaa tcaccggtgc  126600
tgctgtggag gaagagcttg gtggcgctag gacgtccttg tgaatgtgac ttggaagagc  126660
agtttgggat tttttttcatt gcctgggat gagagggaga gacaacgtgt gtcttacaca  126720
tctcccaaca gccgacttag atgtgatccg ttctcccaga gggagcaggt ttcttttgaac  126780 ttttcctttt tatgtacagc atgtaagtaa acaagggctt tgattttcat gggtaaagat  126840
```

```
tttgatccaa atgtaggcat gcttgcacgg tttccttttc ttgattgaaa gttgattttg    126900
ctctaaaaat gtctaaagac tgatatgcag atgagaagag atgcctttct ccccagaagg    126960
gattctgaca gtgatcttta catgcttttt acagctaagg ataagagaac ttcttttgga    127020
tacccgttct gtggcgctgt cactgttcct ttctcattcc aaaatcttta acttcatctc    127080
cgaaatagtt ctttcttttt gaaatataaa gatatcagaa aggcctaggc aaatatttac    127140
tctacaaaat atgcttgaaa agacagggag gaataaattg aatatagcaa ttaattgtat    127200
gcttgtaaaa tttccttgga gtatagcaca tattaatact tatattgggt ttaatactgt    127260
aaaagaaaat tcacaaacat gaaacccatt ttctacaagg taagcagagt ttttaattta    127320
gttattcttg atgaaataat ttttcggctt tgtggaagaa ttttatgtaa tcacctagtg    127380
tcgctttggc agggattatt tttgccgttt gtaggcgttg tgttgataga acagagagca    127440
ttgagaatct ggagatacac agcgtgacaa ctgtgtgttg tgctctttgc aatttaatct    127500
tgtttaagat ataattgata tattttgtcc tgtttatttt ttctaggcag aaaaaaaaga    127560
acgtgcacta gtggctatgg ttttagtgt acagcgtgaa caaaacttgc atttagtatt     127620
taatttctgc tcacccactt ggcttaacct tttgagtttt ttttgtcac atgaattgct      127680
tttaagagct tgcctatcta agaagctgaa ggaaaagaaa aaattattgg accacatgat    127740
ttgcttccca gcattcttgg agttttcgtc ttcctttggt gtatacttgc ctgcattatt    127800
gcaagatctt tttggttatg ttttgttag gcagtcaagc taaagataa cttatttata      127860
aaccgtagtc tttctccatg gttgctattc aatagatgaa tagaatcatg atccttttct    127920
taaaaccaaa catgcctatt tctaaatgca agttatgtga ctaaattcct attttaatgc    127980
acggagagat ggcctcctca aggcaaacgc tttgtccctg aaaaatggtt tggggtgtgg    128040
cagtctccag caggaagaca ataatctgtc acaaagacct aattccaggt agcccttct    128100
tggaggcagt ggtatgttgg aaagaactcg acctgatgct taaacctgaa tttgtattcc    128160
catccaccat gccttatcat tatgtgacct ggggcaagtt acccaacctt tgtaagcctg    128220
tgtgtcctcc tctatgaata aacataaacac caccaccaac ccagtgttgt caaaggaatc    128280
acgtgagatt atgtccaact aggagcactg gaagcagggg agagaggatt aggctgtaag    128340
ctgcccttc ctggtgcgtc tcccatgtat acgtgtgtgt gtgaaggttt ccctgttgc      128400
tcacctaatg gcctcttgag ctgagattcg atgtcaggta ggaaactgaa caaatagatg    128460
agcacctcaa taaaatgctg ttgaaagtaa gacgtgcatg ctttgaccat ctcagctgcc    128520
cacccgtgtt cttgaccatc tcagccatcc acccgtgttc tcgaccatct cagccgccca    128580
cccgtgttct tgaccatctc agccgccac ccgtgttctt gaccatctca gccgtgttct      128640
tgaccatctc agccgccac ccgtgttctt gaccatctca gccgcccacc cgtgttcttg      128700
accatctcag ccgtgttctt gaccatctca gccgcccacc cgtgttcttg accatctcag    128760
ccgcccaccc gtgttcttga ccatctcagc tgcccaccta tattctcgaa gttagtgtca    128820
gtggtcaact tctcccgaac cgtcccatga gatgaaaatg aactagaaac cgaaagctgt    128880
aagaattggg tcctctttgt tgtctgcatg gagacaaagt ctgctcaccg tgtagctgct    128940
ttttttttaat gtatagtgtt gtaaatggat gagctttcc aaagggttgc ttcaagtgac     129000
caaataaaaa tagtgtatgt tagatctgcc tttccctta gcaggagtag gctgtgaaca     129060
ccgagatgct tagtgaagcc tgagcggctc tgccagccga ggagggcttg cagactttgc    129120
ccctcctgga agagaggcgg caaggacaca gatcaccagg ggtcagagtt gggcggagtg    129180
tggcaccagc ccatatgcct tattctgcct ctctaacgcc acacttcctt ggcagagact    129240
```

```
tggaggcaag tttgtggact tgtttgaaat gactgtgctg tttttgttgg agtctcaaag   129300
gccatttgat ctcttgtag tgagttggat ttttttttaa aaaatttcct attttccgtg    129360
ctccagagta tttgtgccct gctcttcttg gtctatcctt ggtcattagg gtggatgtgt   129420
caggcagatg ccaacccctt gctgggtgtg gcaggaagac ggtggctata aagacatta    129480 ctgtggcata aagcacacag agacctgttc ttttctttgc cagggataac ttacacgctc   129540
tgttcaacag ggttggcaat gtcacttacg tgtcaacagg aaaaacagga aaaaaaaaa    129600 gagtggtatt gagaatccaa aagacagcgt tccaagcaag tggctgcctg aaggcccctt   129660
tggcaatgga gagcttgtcc tgtagagagg atgaacaac agagcgtggc aggaaggcag    129720
tgggaagaaa cttgctggtg acctttctcg ccatttcttg caactggccc ttcccgtcag   129780
ctgggctgat tcctcctgcc aagtgggtcc ttggacagag gcaaactaaa aagtgggcag   129840
tggggctgtt ggcatggtct gtgctgtggg ctaactgggg ccaaagagaa attgccagca   129900
acaggaagtt gcctgatgag tcctcagctg gctgtgcctt tgccaggcag gcttttaaaa   129960
ctcagacatg gggtgttgag ttattgaacg agactttggc tggggctcag agtctgcctg   130020
cagctgtggc agagggcctg tgttttctct attaaacatg gaatacacgt atgtctagga   130080
gcagagtatc atgcaaggca gggggacttg agcctggcga ggctggtctg gaggcctggc   130140
gggctgcaca gtaagaaccc caggagccct gggccagcct ggccccacca gtgcttgtgt   130200
ctcctgatcc tgatctggaa agtaaggatg atggcaccta gcacacagtg aggttggaag   130260
gatgcaggga ggtcaccaat tgcccttctt ccccttttcct ttctgtcttt ggatcactga   130320
ggcactttcg tcagcacaac tggcttccca gcctcttttt ttttggcaga aagagtttta   130380
atgaaaaaat agggatttgc attacaaact agggacaaaa agaagacatc gtttaaact    130440 tgaagttata gaaaataatc aagcgtgtct tacctctttt taaaattatt attatacttt   130500
aagttctggg atacatgtgc agaatgtgca ggtttgttac ataggtatac atgtgccacg   130560
ctggtttgct gcacccatca acccatcatc taccttaggt atttctcctg acgctatccg   130620
tctcctagct cccacctcc actacaggcc ccggtgtgtg atgttcccct ccctgtgtcc    130680
atggttctca ttgttcagct tccacttacg agacatgtgg tgtttggttc tttcccctgc   130740
tgttttctgt gccacagtac tttcctacct gccttcctct gtccctgctt tcttcttttc   130800
cagacttttc tctttcatct tgttttttt tttttttgaa aaaaaaaaa acaaaaaaaa     130860 acacaagtta ttattcagag tcatcttcag aatcacaaaa taagaagta aaaagagaa     130920 gttttagaga gcagcgctgt gagagctgca gtgtgaatca ctgcgctggg gtgggctgga   130980
ggatcagggc ctgtcaggtg gaatgctggc tctgaaatta acttgctgaa gagataatga   131040
cactcccgtt cctcatcctg ctgggacagt gatgcacagg aaagtgactt ggagactact   131100
cagagctgag gccacacaaa gatttgactg agcagagatg ctgatcttca cctaatgctt   131160
tatttgccac gtttatttct gatacaggct tctccttttt ctctccattg aaacagcggg   131220
tgccatggtt ttgctctcat cctgtctgag atgacacttg aagtgggata tgtttgacct   131280
tttcaaggca aacagaaagc caagttcaag gagtcatcag ccagctccct gcaacttagg   131340
tggtcgtaag ggacctcttg ccagagctgc ttgaggtctc cccttaatt ttgtccacct    131400 ggatgacagt gaagatgggg ttgaacggca agtgtcccat gtctgtcctc tttcttccat   131460
cttccctctc catgcccctc agccctctat ttccagatct ttatttcctt tctgggcttc   131520
tgaattagag atggagctat ggagaccttg atataatttt gctttctgtg ggagaagaaa   131580
gcaggaagtt tgatttctca ggccaaacta gcctcagtgt aaataccatt tgcaggttct   131640
```

```
tgcctattct tcttcttatt tatttattta tttttgtttt tttgagaggg agtctcactt    131700
tgttgcccag gctggagtgc agtggcgcga tcttggttca ctgtagcctc tgcctcccgg    131760
gttcaagcaa ttcttatgcc tcagcctcct cagtacctgg gaccacaggt gcacgccacc    131820
atgcccagct aattttttgta ttttttactag agacggggtt tcactatgtt agccaggctg  131880
gtctcaaact cctgacctca ggtgatccac actcttcagc ctcccaaagt gttgggatta    131940
caggcgtgag ccaccacacc cggcctgttc ttgcctattc tttggggaag ccacctcgac    132000
atggggtaca ctcggagtaa gaacacatgg gttgggtggg cgtggctcac gcctgtagtc    132060
ccagcacttt gggaggttga ggctggtgga tcacttgagg ccaggagctc aagaccagcc    132120
tggccaacat ggtgtgaccc tatctctact aaaaatacaa aaattagata ggcattgtgg    132180
ctcgttcctg taatcccagc tactcggag gctgaggcat gagaactgct taagcccagg     132240
aggcagaggt tgcagtgagc caagactgca ccactgtact ccaacctgga tgacagagca    132300
agactctgtt tcaaaaacaa aaaacaaaca aaaaaaaaa acacaaaaaa aaccatgggt     132360
ttttgccct aagtcttaca ctgaggagcc gtttcttcat ccttgggtaa gttgtcaaac     132420
ttccctatct gtgaaactca agggtccgtc tgaccagctg tcctgccctg atgtctctcc    132480
ctgtctgtct ttctgcctga atgcctgatc caaagcagct ttctgctaga tatcccttttt  132540
tatccccatg aatatggaga gctgcttaga agaagaatct tagcagaacc ctattagaat    132600
ttgcttcggt cgtttattgt ccttcatgca tttcattgaa gctaaaacct gtaagatttt    132660
tggaggcttc tcaggtaatg gtatgcgaag gtcaggatgg ttagataccg tatttccaga    132720
tgctctctgc tcttttatgc acttacgtta tttaggaact tatttcaagc agaccatttg    132780
agaatctgag gaaagctatg ggtccccaga agattgctta tgcacatacg ttagaaaattg   132840
cagacaattc cagggagctc cccagtctta cgatgtttat tcacagcttt ccctgttagg    132900
aatttatgaa ccgtcagttt gtgatcctta ctttgagtaa acatctgaat agcctagcct    132960
gtgtcttaat attattgata ttgcagaatc agttatcaag tacctgcaat atgaacagca    133020
ctgtgtttat atagtcaagt gatattttga actttgtttt tatcttagtc taattgcttg    133080
ggtgagatta gctattaatg ctttattttt ttaatgtgct aagagatgtt gaggaacgtt    133140
aaataaataa caacccctag atggcaaata aattattagg ttgagaccag aatagattat    133200
attgatgatg tgggtagac atccccagat tttttttttct ttttttttt ttttttactc     133260
tgcacttcaa tggatgcaaa cccaggttgt taaacaccaa tcgcagcatt acgtgctggg    133320
atgttttggc atttttgaaag tttttatttttc tatcattagt gaacaaaatg ggttttttt   133380
tggagtaaga attttaacat tttgatccca aaccaaactt ttatggatct ctttagtaaa    133440
ataaatagct gtctgatgga ctaggagggg tgttttttat gctcagcgta agggacgctc    133500
aggtggctgt ggctcctgtg ttccccggca agggcgttgc cagtgaattt caccctttccc   133560
cttttccatgt cagcaaatta gctaagcct tgttgtcgtt cgccctttt cttttaaaga     133620
agtaataggc acaattacta tctaattttg gcttgccact gtgtgggtgc ctggaatctc    133680
atccgatctt taatatttac ccaggggggt gggtgtagtg tcgcattatt cattcactca    133740
ttaaatcccc ttcaccgagg cctgctcaga tgcttgccat tgttcaaagt tctgaaatcg    133800
tcacctggct gccttctgtc aatattcttg cgtagagatt gtagtccaat gaaaaccttg    133860
tactgagtga agaagatgt gtttgagttt caaggcattt tctgtgcctt tcatgactca    133920
tagcagattc tcaccttgtg ataaagttcc ggctccacag tggtggctgc ttttgctttt    133980
gcaaaagtaa gttgtgagaa attgttctga gtcatttgc aatttcctct atagactcag    134040
```

```
ctaagagtag atgtgtgtgt catgagtaga tgtgtctgga gttgagggag gaggggtcat    134100
ggaaaaactc tgcctggaag tgcttcatcc aggtacacat gatggtattt tcaccatctc    134160
aaacactagc ttctaactgc tgaaggttaa gatgggatca ttcgttttgt aaatccgtct    134220
cctgctgtct tgataataac atgaagaaaa gggcaagaaa acatggatg tgtcattagt     134280 atggaaggaa ggaggagaat ggaggtttgt tttaaaggca cccccaattc tctttccctc    134340
tttcatcctt tcgttggttc ttgccccttc cacaccccga ctgtgtttgt tcagcctcca    134400
gcgcatgctg ccgcctctgc tattcacctg cctttgcgct ctctcattct ttgctgccac    134460
ctgagtcctc tggtgttttc agaaaacagc tggcagagga ggaggctctg agatgtgcag    134520
ttgcttagaa ggttctggcc tggcatctgc acagcgggga tttcatcacc aactgctcag    134580
aaaccacaaa tgctgcatgc ctggaggagt cctgccatct tcctaccttg catgccactc    134640
tcagctggtt ttgggatttt ctatttattt gtttgtttgt ttgtttgaga tgggtctcgc    134700
tctgtcaccc aagctggagt gaaatggtgc gatcttggct gactgcaacc tttgccttcc    134760
aggttcaagc agttctccca cctcagcctc gcatgtagct gggattacag gcatgcacaa    134820
ctgcacacag ctaattttg tattttggt agagatgggg ttttgacatg ttgtccaggc      134880
ttgtctcgaa ctcctgactt cagatgatcc acccacctcg gcctcccaaa gtgctgggat    134940
tacaggcatg agccaatgca ctcagctggg atttttaaga gtttattccc ttcttggttc    135000
attcaggcat agataaaggg cagtctgagg gcccgggtga cacacccatc aggacaggtt    135060
ggtgctctgc cttcctctca tttgagcacc gaggtcttga atttgggggct tatacagatg    135120 agttaccaag atggggaaag gtggaccatc aagcagtaat acaacgtgag gcttacaggt    135180
aacttctaag tgtggggctt taagaaaagt ctctgttcac attctgtcac cctcactctg    135240
tctcttccat cttttcttg cctgagtgtc ctggttctgc tgccttctct agatccccag     135300
ctcttctcac caccagggat acctggcttt ggttcccatg tatttattga tttctatttt    135360
taagaagttt gatcaaaact gtcaagttat ttattgaaaa tgatagttgt cttagtttaa    135420
atcttattcc atttctgtta gaagtcagtg tagattatag agtggtaaag tctcagataa    135480
atacttatat aaataaagat aggtattgtt ccatataaga ttatcattat tttgagaacc    135540
tgttgatgag ggtgccagat gtgactgttg cattactcaa atccagcaaa aaacactgaa    135600
caaaaaccat aattaagggg gcacacaggg tatctgtgct cacttaagg caagtagccc      135660 ttggcagtac ccctgcttaa ttaaggttgc caggatatta acatgtaatt gatgttttat    135720
atacttataa ctttcctccc agaagctaca attttttga aaccagattc caagcattgt      135780
tttaagccaa tattagaaga gaaagtgtag ggctttctaa gcatgaagag gatgtgatt      135840 cagacgaaat catagcacct ggaccctgtc tccctgcccc catcccattc ttcataagcg    135900
atgaaaagca tctttgatcc atgaaacctg aaaaagcagc catcagtaga agtaagtgtg    135960
acggctgaag gtgtcataag atactaatgt accagtgggg aatgggatgc aaggctgctc    136020
agcctcagta gccccttgg ctggctgagc atctttgtgg gctccgcttt taagtggaaa      136080
caaaagattg ctgatggtag gttgggtgtg gtggctcacg cctgtaatcc cagtactttg    136140
ggaggccgag gcaggtggat cacttgaggt caggagtttg agaccagcct gaccaacatg    136200
gtgaaacccc atctctacta aaaaaaatta gctgggtatg gtggtgcacg cctgtaatcc    136260
cagctactca ggagcctgag gcaggagaat cacttgaacc caggaggcgg aggttgcagt    136320
gagcagagat cgtgccactg cactccagcc tgagcaacaa gagtgaaact gcatctcggg    136380
tgggggcggg gggcagggaa gaaaaaaaga ttgcagatgg tgaaatttaa atgcttaaaa    136440
```

```
aaatctttaa gaactcataa tttgcctgca acaaattcag gtggtgacat agtcccttc    136500
attcccccaa gtcagagccc gtgcccctgt gtgtctgtcc ccatcagtga aactggggct   136560
tggtttcttc tggagaagaa taatccaggg caagtcaagc tgtttgtttt gcgcccctgt   136620
ctctgttgct gagttgctgt caccttgagt tggctctgac tgtcccgtgg cgaaggccat   136680
cccaaacagc acatttgcag tatgtgctcg gagagtggga tacataagaa acaggagagt   136740
taactagaag gattttccct cctgctctac taagttggaa aggaaagtag atgtttgtct   136800
cttaatttgc tgttgcacaa agtgaaaaga tacttggacc agaattgctg gagctttcca   136860
tgcactcaca gtgggctttg gaaaaatcat tcactccctt gaatccttat ttgttaagaa   136920
agtgggattc catttccaca actgtttcat ggctgtgagg tgaaataaag actaggcatg   136980
cggaatggct ttgtaaactg caggggtgct gagtcagtct gcggagactt agcccatggc   137040
gaatacaatg tgttttaaat acatcacttc atttaaaccc gttttcccca caccctatt    137100
gaacagatat taccagcccc atttagcatg agaaaactca aattcagaga tgtcaactag   137160
caggccagtg tgtcctaggc agtgactgta ccacggatcg cgcccagccc tgccagcttc   137220
taaagcactt cttcccatga caccacactg cctcgtaagg agaatatggc actgcgtgta   137280
gaagaaaggg gagaaaactg tatttaagta tcagactcat ggcatatggg tgtatttact   137340
cttcaattga tttaaaggta gagcgactgt atttgtgaaa ttgcaaggta cgatgttaga   137400
aatctggaca cgactttttg gttctttagc ttaatttaca aagttggtta caccccccgtc  137460
gacaagagga atctgtgagg atatagagat ccaaggctta tgttccaaaa gcaggtagac   137520
tgtgacagct ggagagagcc agcagaggat gcagcctcct cagcagtcta gaagcacatc   137580
taagatgccc aaggagtgtc ggcaaggaac tggaatgggc gcaaccgaat tatttctga    137640
gcatcttaga actattatca gagcagagtg cttggtctgt acctgggagc caggtgctgc   137700
tctatttttt gtttcgttt ctaggttaag gcagccggga acccacatgg attacaacta    137760
gaaagaaaat caatttctag ggagccagag aaagggagga agggcttagt gaagggagag   137820
tctgggctca ggtagttggg cagagctgtc ctaagcaaag ctgggtggac acagcctgaa   137880
ctgctaagcc taagtatgtg ggatctcccc cttcgagtat gcgactgaat tttgtcctca   137940
gttttctgta ggatagactt tacctgccca ggaaattggt ggctaacgga gatttgtcag   138000
agctctagtc tgtcaagaat ttggttatag ttgctgttat tgacacattt tgtcttcaaa   138060
taaagtgata aagataatct ttttggcgct ttattgtcca atcatgaata tataaaaga    138120
aaaaagtctc aactcaatac ggtctcagag tatgtaacac tgaagacctt tcctggctgg   138180
gcatgatggc tcatgtctgt tatcccaaaa cttggagagg ctgttaatca gaagcaaagc   138240
catatctttc tttccgggtg aaaaatgggt tagagaaaat gcagttcctg gcagaggagg   138300
catacattag acagattagc cttaagggta gcattgaaac tcccagaatt ttatgtgaaa   138360
gaggtggctg gttgtgtaga aatgctgccc tggcccttga aacttccttg gcagagaaa    138420
catcttattc attcctgaat tccgaccaaa ctcctgttaa ataaggaaac cgagcagaag   138480
gcaggcagcg aggacacaca agcccgacgc tcctcctgtt cccaccgctc tggcaccagc   138540
tgctcagttg ctccgtcctg gggagcaggg gtcctccctg tgactctggt ctgggaagcc   138600
ccacagcagt gaccatggcg cttcctctct ccagcatgca gctctgacct gccttcctgg   138660
gcatgccccc taggcactca ggatttgcca cttgggacat gcacatgctc tctgccttct   138720
caggaaagta tgtccgcatt tcctccagac agcgggtggc cactgcccac ctcctccctc   138780
tctgaccatg actggtgctg ctcattccag ccctggcctt ctgcacgcct cccctcgttg   138840
```

```
ttactcttcc catagccctc gccactttat tgagatactg agttttgttg tcactgtgcc    138900
tgttgcctct ttctgccttt tatccctaca cccagaacag agcctggcag acaggaggtg    138960
cccagtaaga aactgctgat gagatgaatt tgactgttct tgcccttcct ttggggcact    139020
cgggaaattt attcttccat acttgtaaaa atagaagaac ttgagacatt gaatgccctg    139080
tgcaaattat aactttcatt gagccctggc ctttgtggaa tccttgtact atgctaagta    139140
ttttacact gaatgctctt gaccacccttt taaatgtgac ccctgctttt ataggcaagt    139200
aaactaagtc atggagcagt tagccatgat cacacagctg gtcatggcca tggccaagaa    139260
aggtttgtta taactccaga gcctgtgtgc ctaagtctcc tgtcttgaaa gaagtaattg    139320
ttgaagaaaa gcttagtctc aagcacattc tgaggcccttt ggtgtgagtt tcacacttac    139380
agtgggattg tgaaaggggg cagagcccag gtgtattaat tcattttcat accactgtga    139440
agaaataccc gagactgggt aatatataaa gaaaagaag tttaatggac tcacagttcc    139500
acatgactgg ggaggcctca caatcatggg ggagggtgaa ggaggagcaa agtcacatct    139560
tacatggcgg caggcaagag agcgtgtgca ggggaactgc cctttataaa accatcagat    139620
ctcgtgagac ttattcacta tcacgagtac agcatgggag aaacccaccc ccatgattca    139680
attacctccc actgggtccc tcccatgaca catgggaatc attacaattc aaggtgagat    139740
ttgggtgggg acacagagcc aaaccatatc accaggtgac acctgtacca ccgagagtac    139800
aaatccacca catagcccat catgctgtca cctgtaagct gtgtgtccag taggcaacag    139860
gggctgctga actcacctcc aggtgggtct cctccaccca ctcctgctct ccctgagct    139920
cgtctccttc acagaaagtt caccacctca tgcccctcgt ctttgtggtg tccacagttc    139980
ctaactcgca cctgccagac cctgcctctc tgtcctgcct tgggccacag ttacactggc    140040
cttcaattcc tgacacactc tgtgcttccc ccagccccaa gctgtgcaca gtttagctga    140100
ctttaacccct ggctccagtg ttagctgttc ctgtccttgc ttcaaccaga gtagctctct    140160
ctgttgtgtt tccgtaggac cccccacttt cggcactggg caccttttgaa tgacttgctt    140220
aaagcttgtc ttcccagcca gactcaagga gtgatttgtt catcaaagtg tctttatgga    140280
agcagaatgt cttatcaggc cttttctgcc tcaaataatt ttttttaagt ggtaggaaaa    140340
gattccatta aaaattgtaa aaattcaacc gctataaaaa aatgagaaaa ctcagataag    140400
ccaaaagatt aaaataactt gaaaggcagt gttaaccact gcatttatta tacatgtagt    140460
tcaattttat aaaaatctat gcatacatat ttatataagt aaatatacat aaaattactt    140520
ttaaattact ttaaaatggc agagctactt tttttttttt tttgagatgg agtctcgctc    140580
tgtcacccag gctggagtac agtggaacga tcttggctca ctgcaacctc tgcctcccgg    140640
gttcaagcag tcctcccaac tcaggtcctg agtagctggg attacaggtg tgtgccacca    140700
agcctggcta atttttttt ttttttgtatt tttagtagag atggggtttc accatgttgg    140760
ccaggctggt ctcagactcc tgacatcaag tgatccgccc accttggcct cccagagtgc    140820
tgggattata ggcgtgagcc actgcacccg gccctacttt cttcccttac cagtaaatca    140880
cgtccttctc ttctggtcag cagatgttgg tctctggcat cactggcagc tgctgcatat    140940
ggctcctctt catactgcaa tttctttagg tgactgttta cttcacagt ttatgttctc    141000
attctgccca ggaaatagaa cctttggaaa tggaactgtc tagtctagaa gacaaataat    141060
atggggctct ttggagcagc atttcttcct ccttttttgta ccatttttgat aaatataaaa    141120
atttcataca atttccctgg agtatttagt gtatcactat aaaatgaatg gtttgtcctc    141180
aacttttaaat gtctctagtc atcttgaacc tgtttttttaa ctcccaccac accctgccaa    141240
```

```
ggggctgacg tgctgcccct ttccttctcc actccacgga gcatgccggt ccaggagaaa   141300
ctggatgtgg tgttgccctc tatcagcctg tgggccctgc cagcttcccc ccaagcacta   141360
aatagagttc agccctgaaa tcctgacctg gctgcagtgg ggtagcccag ggtagctgca   141420
gctggatgtg cagaccagga gccccttgtt cccactgtgc agtccagatg tgcaggatcc   141480
acctccactc aagagcatca tctgtgttgg gcatggtggc ttgcgcctgt aatcccagta   141540 tttttgggagg acgtggcagg tggatcacct gaggtcagga gtttgagatc agcctgacca   141600
acatgatgaa actgaaaccc tgtctctact aaaaatacaa agattagcca ggcttggtgg   141660
cacgcacctg taatcccagc tacgtgggag gctgaggcag gagaattgct tgaacctggg   141720
aggcagacat tgcactgagc cgagatcgtg ccactgcact cccgcctggg tgatagagtg   141780
agactctgtc tcaaaaacaa aaacaaaaac aaaaaaaaac aaaaactggg gaagtagtca   141840
ttcagccctc tgtggtcctt ccagattcca tccttgccag tgatatttgg ggataatact   141900
agatctttct gtaagttaga cagtgacttt tacgaagttc agagtgagtt gagaaaaagt   141960
ccttcgtgca attttttagtg ttttttttttt cccgttttcc taaagggaac ttttctgact   142020
taatgaattt gcttgaatat gacagctgac agtgtcattg cgctctgaga ttatttagta   142080
gtgcagcctc cccatgcctt ccagacaatg aactgggaat attgtaagtg ctcagtgtat   142140
gagaacgcaa accatataaa ccacacccct tctggggctt gactttcctt aaggataact   142200
gaccgtttgt cccaggccta aatgtatttt gtatttttc tagcattcta tttcggtgca   142260
ggaggagcag cagaaccta gttcttctga ctgatgtcct ggtttgggga aactctgagg   142320
acatgagact tggattcagt ccaggctgat ggctcagcac agagtgggtc aggattcagt   142380
ccaggcctat ggctcaacac agagtgggtc ggcatgcgga gggagaggga tctcccgcca   142440
gggatctgcc gaaagatcat actgcaaagt gacgggacca gctcaccgaa cagcgtggca   142500
gtctctttcc tagtagcttt ctatgttggt tacgtctgtt acggatcctc ccccaacata   142560
cttttcctct aaagcaggaa ttgaaatgta gtacacactg caaatgctgt ccttcatcct   142620
tgtttctgta tgccacatta ccccaaatta cgcagcactt ttaaaccttt tttcttagac   142680
tgaaagtgtt ttctgagccc aagcaacaca aacaggtgcc tttgacaaga gtttgcagta   142740
cccagaatcc ctaaatgagg ccacagctgc accctgagcc aggaaaggcg ggcacgtagc   142800
tcagcttctg atgcagtgga ctcctgccac gtatttcatg cagtagctac aaaatttcag   142860
gcatagtctt gaaatagttc tgggtaatgt gatgtaccta ccccgtagta gtttaaagat   142920
tccaaaacgc acaggaaagt tgaaaggcct caggctgtga tgtctctgaa taagacaaaa   142980
gagaatatca aagttgttgt gatcaaggga acagatttca caaactgtca tcaagaggag   143040
gccatcatgt tatttttcta atgaaaagta ttgcactgaa cccaggttag aaggttcatc   143100
tgagtgactc agagcttggt ttgacaaaga ctctgtcctt caaagaccgt caaagagggt   143160
ctgggcgagc tgcttgatcg tcctaagcag ttttcttgcc actcctaaga aatgggttta   143220
tgggctcctt gaaaatagac aagaaaatgt ccttatccat acattaaaac acaaataact   143280
gcttagacgt ctgcctgaat tcagagctct tgagtgggat gctcctcatc tataaataag   143340
ataaaatcat tttcaagcag ggatcaacct tagtataaca ttaaaaacct gaactaaagg   143400
cccggcatgg tggctcacgc ctataatccc agcagtttgg tgggaggatc gctggagttc   143460
aggagtttga gaccagcctg ggcaacatag tgagaccctc ccttctctac taaaaatcaa   143520
aagaattagc tgggtatggt ggcatgcgcc tggagttcca gctgcttagg aggctgaggt   143580
gggagggttg cttaattcca ggagtttgag gctgcagtga gctatgattg taccacagca   143640
```

```
ctccagcctg ggtggcagag tgagaccctg tctcaaaaaa acaaaacaaa aacaatttga  143700
gagaaaattt ttttgggggg ggggttgggg ttcaatatca ttgcttttcc agatagcata  143760 attttggaa  aaaatgtttt tatttaatct ttttatgact tcttaaagaa aatattggtt  143820
tcatgctctt ttatgaaagc tgaggcctgt gatggaccca agtttgtagc attgattgct  143880
acaaactgga aaaaccaat  ctgaggcccc catttcaagt gcccgtgttt tttattctgc  143940
atatgcacat cctgttaggc cactgaatcc tcacactccc agccctaagt tatgatcatc  144000
tgtcttttgc ttttatttat ttacttttag agatagagcc tcactctgtc actcagtggt  144060
gtcatcataa ctcactgtaa ccttgaactc ctgcctcagc atcgttagtg ctgggacca   144120 caggcatgtg ccaccacagc cagctaatct ttttatcttt tgtaaagatg ggtttcccta  144180
tgttgtccag gatagtcttg acctcctggg ctcaagccat cctcctgact tagccttctg  144240
agtagctggg accataggcg tgtgccacca tggccggcta atttttttt  atcttttgta  144300 gcgatgggtt tcccttatgt tgttcaggct ggtcttgaac tcctgggctc aagtgatcca  144360
cctgcctcat tctcctaaag tgtgggatt  acaggcatga gccactgtgc cagaccagtc  144420
ttttgctttt aaagcagcat tcctggggtg ggggtggaat aggctcaata gatgtcccag  144480
ttgtctgcat atgagctgtt tctgcctctc taagcagagg tggtctccag aggcaggtgg  144540
ctgcatccct agaacacctg gggccaggag agccctgacc acatggggagg cagaggcagc  144600 aggaggcgtg aggaactaga ttgctttgcc tgtgctctgc taaatacctg ggagtggcag  144660
gggctgtgcg gacagctaga gaggggaaca gagctagaga cggagcacag ctagagatgg  144720
agcacagcta gagacagagc acagctagag aggggaacag agctagagat ggagcagagc  144780
tagagagggg aacgggccct gtgccattta aggtctcgct gaagcctcct tgcccctcag  144840
ctggaaagcc ctggagagtc atggtaaagc tgcaatgctg gcatgttctg tgagaaacct  144900
cccaactgtg ccttgtgcac agcagctgct cggcaaacac gagtttcctt ttcttcttga  144960
cccaaacggc aattttagca gttacttgat ggaataggca ttcctgctgc cttttcatca  145020
ggaaggacac tgaagactta gaatcgagac ttgcccagga gtgcacagaa ggctgggggt  145080
tgagcctgga ctgcagccca ggccttctga ctctcatctg tgcttttcag gcctatcacc  145140
atatatgcat gtgaagatat cccagcccag ataatcacta ttcctataaa gtgctgatca  145200
ggttcaccca aatgtccct  ctaatgtttg taaacatcac gaacagtggg tgaactgaaa  145260
tgtaatcacc caagtgactc cttcagctac aatctgaaaa gacacactta taattactct  145320
tctccttttg ggggccctgc ctccttttgg tcccaagtaa tcctcaccaa ctcccttaga  145380
caacagctaa aatgttaagt gtacaaaagg tggctttcta gcacttgaac acttaattgt  145440
ggtactttaa gaagtaaatc tgctatgaaa aatctcagct aacattcact ttttgggagt  145500
taatcttacc agaaaagttc ataaagtgaa ttctgttttt ctaaaatggc aagatacttt  145560
atttgtaaga tctcgttact ttaacactgc attgttaggt gtgattttg  acatcccagt  145620 gaagcaaagc cataatctca ccagatgcca tttaacttat gatgtatttt atcagatctt  145680
attttataca gtatattcaa gcttaatata gattctatag ccctgggaac tgttagtttt  145740
caggactgca gaattatatt gtctgagctt gtggtgcaaa tcccagtaca gagatttcaa  145800
atcagtgagt cttggagtcc gagtattatc atcgtgaaca ttttagctca cttcatagga  145860
ggccacaacc agaacaccag agtcatggct gtgattccgt caatttcctg tagcccgtga  145920
gctctgtcca catacctcag tggggaccct gggacaggtg atcccactgg agccagcacc  145980
actcccagaa atccaagcag aacgcgagct gtatgaagag tagaccagca gttctcatgc  146040
```

```
aggccacaca ttagcaacac ctgggggagt ttttttaaga aacacccatg acagccaggc   146100
atggtggctc atgcctgtaa tcccagcact ttgggaggct gaggtgggca gatcacctga   146160
ggtcaggagt ttaagaccag cctggccaac atggcaaaac cccatctcta ctaaaaatac   146220
aaaaattagc caggtgtggt ggtgggcact tgtaatccca gctacttggg aggctgaggc   146280
aggagaattg cttgcacccg ggaggcagag gttgcagtga gctgagatcg tgccactgca   146340
ctccagcctg ggtgacagag caagactctg tctcaaaaaa ataaaataaa agagcaagtc   146400
atatcttacg tggatggcag caggcaaaga gagcttgtgc agagaaactc ctgtttttaa   146460
aatcatcaga tcttgtgaga tctattcact attacaagaa cagcatggga aaggcccacc   146520
cccatgattc aatcatctcc cactgggccc ctcccacaat acatgagaat tatttatggg   146580
agctacaaga tgggatttag gtggggacac agagccaaac cataccattt tgccctggcc   146640
cctcccaaat ctcatatctt cacatttgaa aaccaatcat gccttcccaa cagtccccca   146700
aagtctcaac tcatttcagc attaactgaa aggtctacag tctaaaatct catcccagag   146760
aaggcaagtc ccttccacct atgagcctgt aaaatcaaaa gcaagttagt tactttctag   146820
atacaatggg ggtacaggca ttgggtaaat acagccattc caaatgggag aaattggcca   146880
aaataaaggg gctccaggcc ccatgcaatt ccgaaatcca gcaggacagt gaaatcttaa   146940
agctccaaaa tgatctcctt tgactccatg tctcacatcc aggtcacact gatgcaagag   147000
gtgggttctc atggtcttgg gtagctctgt ccctgtggct ttaaaggata tagcctccct   147060
cctggctgcc ttcacaggct ggtgttgagt atctacagct ttgccaggca cagggtgcaa   147120
gatgtcagtg gatctgggct ctggaggatg gtggccctct tctcacaact ccactaggcg   147180
gtgccccagt agggactctg tgtggggctc caaccccaca tttcccttct gcactgccct   147240
agtggaggtt ctccatgaga gccctgcccc tgcagcaaac ttctgcctgg acatccaggc   147300
atttccatac attctctgaa atctaggtgg aggttctgaa accccaattc ttggacttat   147360
gtgcactggc aggctcaaca ccacatggaa gctgtcaagg cttgagactt gcaccctctg   147420
aagccatggc tcaagctctg tgttggctcc tttcagccat ggttggagtg gctgggactc   147480
agggcaccaa ttccctgggc ggaacacagc atggggaccc tgggcttggc ccaggaaacc   147540 acttttttcct cctaggcctc caggcctgtg atgggaaggg ctgccaagac ctctgacatg   147600
ccctggagac attttcatca ttgtcttggg gattaacatt cagtccctct ttacttatgc   147660
aaatgtctgc agccagctta gatttctctt cagaaaatgg gattttcttt gctattgcat   147720
tgtcaggcta caaattttcc aaagtttat gctctgcctc ctctataagg ctgaatgcct   147780
ttaccagcac tcaagtcaca tcttgaatgc tttgctgttt agaaatttct tctcccagat   147840
accttaaatc atctctcaag ttcaaagttc cacagatctc tagggcaggg gcaaaatgcc   147900
gccaagctgt tggctaaaac ataacaaggg tcagctttgc tccagttccc aacaagttcc   147960
tcatctccat ctgagaccac ctcagcctgg accttattat tcatttcact atcagcatct   148020
ttgtcaaacc cattcaacaa gtctctagga agttccaaac ttttccacac tttcctgtct   148080
tcttctgagc cctccaaact gttccaacct ctgcctgtta cccagctctg aagttgcctc   148140
cacgttttca gttatgtttt cagcagtgcc cccgactcaa aagagaagcg attctactga   148200
aggagctcag ccatctggga gttcccatgg cagacatctg ttagggtctc acccttactt   148260
gccccttgag gtaggcctgg aacgttactg ggctcctttt cccactgcac ctttggcaca   148320
ttctctggtt ctcccttgga gcaggctccc tccaggacat gttacaaccc tttcaccgaa   148380
gccttcctgg acaaccgatt ctaaaatgct gcctctattc atttaatgtt tattataact   148440
```

```
cttcatttgt tccacagaag tctttgttga ttccagattg ccttaggcta tgctttgggg    148500
tttccagcct tggtgagtct tacctctttg tgtaggaact gtttctactt ctttggagaa    148560
aagcaggccc tcaattgatg accactgaat tgaactgaaa gactagccag agatcaatgt    148620
tgagttttaa tgtggattgt atatttccat catatgacaa cactgtgttg gtggggttg     148680 gggcatagaa cagagagggc agttgagagt ggcctctttt tattttgggg tgcttcagtt    148740
tgtcaagaga cagactgtat aaaaagcatg catcaggcta ccaagtttga ccaacatgct    148800
tgtgtaagct ttctgcaata tccaaggaaa gaaaatgaat tatgtgaata ttaagagatg    148860
ctcctgagaa gttcagcttc ttacccaaga cagagatgga tagaggtcag gcatgaaggc    148920
atttaagctg aaaaaaggag agttttttag ttgacagtca gaaagttgct ggctgttaat    148980
ggatgccagt catttgtgtt gggactcagc tgcgttgttc agtaagaatt tcagtgcagc    149040
agaggtgggc cgagtacctc ctgtgctggc cagtgagctg gctgctggcg gagatgtgaa    149100
agaaagaagc caccctgccc tcactgggct tccagatggg gaggtggtga agtggggtgg    149160
agatgtgagg gtggaatgga aagaatgaga agtaaaagga cactttgtaa tctgaccctg    149220
ctccagcaac tgtggaagcg tttcacctgt gaggcttttcc agccaaagtc tggtggatac    149280
agataggctg tctttgagaa ggcggaagca catggtgctt ctgtctgaat aggagcttgt    149340
gccaaaggcc agtggtcccc ccagatggtc atgttccttc ttgtctcttc atctatgtga    149400
ttcctttccc atgactggga gcgagtattt cctctgagcc cacattccct aggcctggcc    149460
ctggctccct gctaagacca gcttagctcc ctcctcgcag aggtttcctc tggggctggt    149520
tgatccctgg cctctcatcc tcgccaggcc ttatgtgtcc tctgctccct gcctgtgcgc    149580
tctgcagggc tctgcacccc tttagggtga gggtgttacc atcttcatct gcttctactc    149640
cattactagc atgtgcacca gctcaagagt ttctcactca taattctact tgccacaaga    149700
ctgtggagct gagcggttag actggagggc agaactcctg gcccactgtg gccaggtcgt    149760
cctgtaattg ctcttgggct gtgcctctct tgagtctctc cgggctgttc tgtgtgggag    149820
atggaaaact ggattaggcc aaccattgag gggactgggt gggcctgttg aggccatctg    149880
ctcttgttgc tccctagaaa gccataactt cttgatttca gagctacctc accttgactg    149940
cagagggtta gccctaggca atgactctgt aatttcaggt ccaaagatac atctaacagc    150000
tgatgtgaca atggagagcc tcgtgtgtaa acactgaaca tgagtgtggg cgcacatctt    150060
ccttactcag atccgaaatg atagccagag gggtttgagg tgaatgaaac cctttgccct    150120
acacagaggc ccctctgaga tccctgctga gcacagacgg agacacttgg tgcccttggg    150180
ggcagcggat actatcaggg agaggcccgt gcattatttt ccacctcttg tcctctctca    150240
gagtgctgag cagatcactg cactgtgcag gagttttaac gacagtcagg ccaacggcat    150300
ggaaggaccg cgggagaatc aggatcctcc tccgaggtct ctggcccgcc acctgtctga    150360
tgcagaccgc ctccgcaaag tcatccagga gcttgtggac acagagaagt cctacgtgaa    150420
ggtaagggaa gagctggcat ttatgcattc gtgcctcttt gatgatggca agtggtatgc    150480
tggcagaggt ccccagatca cctctgccca ggacacctgc cactcccag gggggacac     150540 ctgctccttg aatcagtgaa ttgctcaagg aagggagggg aagagtgaga gggtggaaga    150600
gctgaggaga ctcagaaaaa aattagatcc ttggcttatt ttgttaccaa ggtagctttc    150660
actatggaaa cagatgttct ggtttgtcat ttgcaatctg tgggaaggga gtctgtactg    150720
gtttagtata aggggagaga gatcacttta ggtgatgagg aacttgggaa caatctgtac    150780
atacgtgacg gctgatccag gccccacagt cttggcggtg gcccgggcca gccctgcctg    150840
```

```
gtggttgtca tcgtgtagaa ctgggacgca cacactgggg agtggtcagc acgtgggaat  150900
atccttgcac cattatgaag gggcagttgc cgagtatctt gagtacccga agaattcatt  150960
tatccatctc ataagccccc agtcagtggt ttgagaaaga ttttatgaag aatactggag  151020
cctggggagc agagttcttt tgctttgttt cctggagctt tggtaccatt tgaagctcgc  151080
ttcatttgtc agttactgaa gcagcgcggc acggtgcggt gggctgaggg tccaggcccg  151140
gctttgcctc cctctggctg tatggtggat ggccccttc aactcccta tttgggtct  151200
gagacactcg gtccccttc tctaaatgtc ttccaactct gacgtgctgg gtccatgaat  151260
taaggcttgg cacacacgtg cggctattac cttgctctgc aagacagatc tgagcttccc  151320
ccttttgttg atgtcgctgt tttaccagga cttcacctaa ggccctattc acaggtagct  151380
tcccaaagcc ccttcttttg gcctcagagg ggagaaagga aagttaggag agatgacagt  151440
ttagtttcat tttccattat gtcttgtcct gcatccaggg tgtggagatg aagtgaacag  151500
ccaggctgtt cagactcaag ttctgaataa tcccatctcc acagtcacct ttttccaagt  151560
cgctgtgtgg cgctgtagat attttggaag cttcagagcc cttctgacat cttgagaata  151620
gtcatggagc tcttgcccca agagttaagg gcagagttga gaggagaatc gatgtccctt  151680
tttggtaata gtgttgttag aatttcctgt taggccacgc tgtactggga gggtcatttc  151740
agtgacaggc tggcagagta ctcagatggt gtcatgggtg aagtagacaa ggaccgactc  151800
tcccttctct ctgcaagaaa cctgcacttt gttttcttag ggcccccctg ggttgcagcc  151860
ctttgccccc cgcagctctg cgcggacctg attttgctgt ccaggaagtc ctcccaggca  151920
gcaccagcct gtgaggcatg actgccaggc cccaacaccc tcggacaaaa taacccacac  151980
ttggcacctg ttgtgattca cacacacacc accgtttctt catttctttt ttgttgctga  152040
cgtttaacac agaatcttgt tgtttttaa cctggatccc ctgcatgctc cttgaaattt  152100
ttgacatcta tgtgttccct gagatatgat tcagtaactt ccatcatctc ccttctctga  152160
gcggtctggc gtggaatatg gtgagggaag gccagggagg ttttatggt gaaagcatcc  152220
gtgtcacagg ccttgccttt tgctctctga actaaggcca gaaagttctg gggatgcttt  152280
gggctttata aagctctggg tcttaggttc ccctcttggg aagtgaggga gttattatag  152340
ctgactttgc agtcaactgc ttctagtatt ttaggactca aaattcttca gaataaaaga  152400
gaaatctttt ctatcactga actatatcct ggtcttgcct tcaaattatt attattatta  152460
ttttggagat ggagtctcgc tctgtcaccc aggctggagt gcagtggcat gatcttggct  152520
cactgcaacc tccacctcct gagttcaaga gattctcctg cctcagcttc ctgagtagct  152580
gggactacag gcacccgcca ccacacccag ctatttttt ttttctttt ttttagtaga  152640
aacagggttt caccatgttg gcttggctgg tcttgaactc ctgacctcag gtgatccacc  152700
cgcctctgcc tcccaaagtg ctgggattac aggcatgaga caccatgcct ggctttggct  152760
tcaaattatt aaacaaaatc tttcgctcat gggttttgta actgcagtct actcccacta  152820
tactgtcctg ctggaacctc gtttgcaaga cagccaaata tggcttagag tttagccatt  152880
agagctgcag ctctgtggga gttttttatt gcctttgaat atgtgagttt gagattctgt  152940
gaatcagtca accccaaagt tgaagggctc cccagaactt gaccctccca gctccatgct  153000
ggacctctca ctgtgctccc tgaggcagaa gaggccagga gctggggtgc acctgacacc  153060
agtgccaccc agacgcccct cctctgcagg gaagtgagtg cccctgctgc agtggcctga  153120
agaaagggtg tttctgtcac caagacactt acctaagcag agggaatgat cgagctgtaa  153180
aggtgtggaa tccagctgtt gcctgtattg tgatattaaa ctctttgaat taggtgagca  153240
```

```
ataatcacta cttttggggt caggaatttc aacaaaggct gggtgtggtg gctcacgcct  153300
gtaatgctag cactttggga ggccaaggca ggaggatcac ctgaggtcag gagttcgaga  153360
ccagcctgac caacatggtg aaaccctgcc cctactaaaa atacaaaaat tagctgagtg  153420
tggtggagca cacctgtagt cccagctatg tgggaggctg aggcagggga atctcttgaa  153480
cccaggaggc agaggttgca gtgagctgag atcatgccac tgcactccag cctgggtgac  153540
agagcaagac tccgtctcaa aaaaaaaaaa aaaaaaaaa aaaaaaaag aatttcaaca  153600
aggcataaac ttcattatcc tgatgggagc cttgggagct gctgccaggt tgctgctacc  153660
caaatctcat gggtattttg gagactaaag cgttgaagac actttcttct attttctttc  153720
aggatttgag ctgcctcttt gaattatact tggagccact tcagaatgag accttcetta  153780
cccaagatga ggtaaataaa atcaccttcc ttctgtccag tgatccacag gttagtctct  153840
gtttgccttt tagcagaact cctatgagag tatctctgtt gatcccaaaa gaacatccca  153900
agacttaacg gtcttctgag agtcccaggc atagcctcct cctaaaccac tgctgtggcc  153960
tcggctgcat gacccagtgg cagagtgttt acaaaggcag agggacggtt atggtctttt  154020
tgaggtagaa gagagtgtga tcagaaattc cttttcaata catacctttg taatgtgaaa  154080
ccacataatt agttctactg acttacattt ttcttaattt gaattctgag aattttacat  154140
ccacttaaaa atttactgta gtaatagaga attatgggggg atggagctgt gaaactttct  154200
atgtataagc catatcccat aatgaatgtg ctgtcttctt aaaggattta ctttctgtct  154260
gcttttccgt gaagaatttc cttgtgattt atttgtgggc ctaagagtta gcgtggtgtc  154320
ctgaacttca tggctaatcc cctcatttca aatcctgatc ttcacataga tggagtcact  154380
ttttggaagt ttgccagaga tgcttgagtt tcagaaggtg tttctggaga ccctggagga  154440
tgggatttca gcatcatctg actttaacac cctagaaacc ccctcacagt ttagagtaag  154500
tatctcagat ttaggcttaa agtaaaaata cgtggctatg gtacgtattt ctctcatgag  154560
aattctctca tgagaaagaa tttcttgtcc tgtgactatt gactatttat tgtcctgtga  154620
ctatttcctt gcaccgtttt cctctgtcag gtggtaaagg aaggctgtat atatttttt  154680
ttcctggcgc aggtgctttt ggtagtcaga agtccagcag cacctcccgc ctggttgttg  154740
accacgtacg tgctctttc tcagctgctg tgaaggatat ccaaggtggt tgcttctgaa  154800
accagagctc ctaccctgtg cccaatcctt cttccccgtg gtcatgtgga tctgggatta  154860
agagaatagg tttctaattg ctgggctcaa gccctctctt ctatgaagca ccagtgctcc  154920
atagcatccg tgtaagccgc agtgtggcag gaagcccctc caaggggacc tggaaccata  154980
cagacagcat cactctcccc aagcaatgca gagtcggctt tattagtgaa cctctctcag  155040
attgtttata tcccaccttg tcagctgtat ttttgtagaa cttctctttgt ttcttgtcct  155100
tggattgcac actgtcagta ggctctgccg ctggaaactt tgcagtcaag ctagatacct  155160
gccaggggag cgcctgggct gttccccacc tcctgtgtgg atggagcagg tttgaacttc  155220
tccaaggcat tagtgctatg gaatctgaca gaagccatgg ggccgtcaaa tgccataagc  155280
cagcacgcat tgattaaacc atgtctgatt tgactttccc ctctgccctt ctagaaatta  155340
ctgtttttccc ttggaggctc tttcctttat tacgcggacc actttaaact gtacagtgga  155400
ttctgtgcta accatatcaa agtacagaag gttctggagc gaggtaagtt gcttatgcct  155460
tttatagttt ttttttttttt ttgcattttt aactgttagt aaagggtaaa tctgtattta  155520
acaagtagag agtaagtaca attttgatgt attaaggtcc atccttgacc ttgacagtgg  155580
caaatattaa agggaaaggt ttctgtttct gtcagttaat tagtagctgg gaacaagtat  155640
```

```
gcctaagagc agagatgttg ctttgccatg tgtcactttg ctgtcagtta catctggatt   155700
cttttcttgc caaattcctt tctctaaaaa cttgcaaccc caaacc ctag atgggagtag   155760 aaagaaatgc atgctatggt gttttttttt ttttccttgt taatcttctt aagcctgagg   155820
agccacaaca gcctaccacg aaactcacaa gaagtgtgtc agctgaaagt aaagtctctc   155880
tggtgcaact ggaaagagct cacatttccc aaaggttgct cttcggtgtt tctctctgcg   155940
tgggcctgga gggcatctgg aggtttatcc tgacgccctt agtgctcatt catgtccacg   156000
gatgcagctc tgccattgga ttttaatcca gaacgtcatg atatcccaga agaaaagccc   156060
cacatttaaa aagtggggtc ttagagtgct tcaaatgagc aagacccagc ccaaatccat   156120
cttctccagt tgctttagac agttgctgaa ctctgttgcc atttcctccc acaaacaccc   156180 tcttttaat taaatttaat taattaattt taaaaatgta aaaatgttcg tagaaatggg   156240
tctcactgtg ttgcccaggc tggtctcaag ctcctggcct caagtgatcc tcctatctag   156300
gcctcccaaa gtgctgggat tataggcatg agccaccacg cctggcccac aagcaccttt   156360
gtattgacag tctgtagtac agtgaaagca taccaatgta cttgtcaata catattgaca   156420
gtcagtgcag tacagtgaaa gcataccaat ggcttgctcc attcctcctt tgtcataaag   156480
aagaggggtc ctgtcaccac ctacttggcc tggtaatcac attcaaaatg gtattgcatc   156540
tcctagaatg ttgtagattt tgatcttaca acacaatccc aaataagggt gtatcttcct   156600
tcagagtagc tgcattccaa gcaactgggc atccagtgcc aactggtgga atccaagtag   156660
cactggtgta tccgctggta cccaaaccaa atgcacctgg attcctacac acacccttca   156720
tggcactcag acaaaggggc agttttcact gccagagagg gtcctactgc catgcctgtt   156780
ggaagggagc tgtggctcta ggtatgcgaa aggtgaatct gcttggagct gtggagtgaa   156840
ggctgtaggc tgcaggctgt ggtgcctgtc accttacttt acaggagaaa agacactgct   156900
ttccagataa cccttaagtg tacagaatac aaataagcaa caactagagt gaggccagtg   156960
ggaaaaacac tggtttattt tccttttatga aattttgtg gtatggtgt agggtctgga   157020 taacattgct taatggcttt tttgatgttg ttttttttga gatggagtct cactttgttg   157080
cctaggctgg agtgcagtgg cgcgatcttg gctcactgca ccctccacct caggagttca   157140
ggtgattctc ctccctcagc ctcctgagta gctgggatta gaggcgccca ccaccacgcc   157200
cggcgaattt ttgtattttt agtagagacg ggtttcacca tgttggccag gctggtctcg   157260
aactcgtgac ctcaggtgat ctgcccgcct cagcctccca agtgctggg attacgggcg   157320 tgagccaccg cacctggcca cgcttcatgg cttttaatga attgtttgaa actcacttt   157380 taggccacct ataacaatat ttctcatggg tatgcatgaa atgtgtcttt aaagtcagac   157440
attcctgcat tttgagtcag tgttagtctt tggggcgcag cctgcattcc atcctcgaa   157500 gctcccagca ctccagggct ctgtcagggc tgtgaggcgg aatcccacgc tgacagctgg   157560
gtgcctgacc cactgatgtg ttgggttttt cattaaagaa tggcattagg aggactatag   157620
aaatagatga tctataaatg ttaaaagaga aatgaagaat ttaattcacc ccactgtgct   157680
cttctgaggt cttttatcca tctgcttgta gctaaaactg acaaagcctt caaggctttt   157740
ctggacgccc ggaaccccac caagcagcat tcctccacgc tggagtccta cctcatcaag   157800
ccggttcaga gagtgctcaa gtacccgctg ctgctcaagg agctggtgtc cctgacggac   157860
caggagagcg aggagcacta ccacctgacg ggtgaggcgg cggcggcacc tccgggcgag   157920
ggcctgcaca gggcggcgag gggctgccag ccgtgccctg ggcctgacag ctcacctctt   157980
ccccgcctag tggcacgtcc taagtcactt ttcagttctg cgatggttaa tcttaggttt   158040
```

```
cacgtgaata tgtgaaacta gctaggcgtc tgggcactcc tttagagctt acaaaatact   158100
tgggtagaaa tgatctcatc cgggtagcgc catactcctc ctatgcaggg atgattctgt   158160
cttcactctc aaaataagta aattacctca ggtcacgtgg ctgtgaaaca gtgccgctgg   158220
aactgaaaat caggcctatt ttcctaccac ttggttaagt tttgtggggt tcgctgcccg   158280
agctgctggt cagatttgtt gggtgaggct ccaccttgtg gagatctctg agcagagctc   158340
ggcttcaaaa ccaaactccc aatgatgggt tatgctttca agtcgctact ggtgtgttac   158400
tgtttgaacc tctgaaatta ctggcctgag acacaattta tcaaaaacac aaagccttgc   158460
agtttgatag taaatagagg atccttaaag aggggcttta tttggttgg agatagtgat    158520 ttgttcatat gttgaaacta ggaggtccaa ttaaaccata ggtgataaaa tttatgggga   158580
gagagaggct tattaacact ttagtattac tgaataataa atactgagaa gagcgtaaat   158640
taaactggct ttttttccat gacaagcata ctttggtatc aaaatcaaca agaggaaagc   158700 attttttgtat gacagttaac ttctataagt aaataataca aattatgttc agcattcata   158760
ctatgtaaaa acttcatttt gtattaagat gatctttaga agggtttgat ttaaaaaact   158820
tccttccaaa cttccctcca gttagaatta aaatgctgaa ttgggagaaa aaaaagtata   158880
aagaatactg aatttagaag tgacctaaaa ttttgctttt tggcttttat aaaataatgt   158940
atctctcata ttccctcgcg gaaagttatg aacatatacc atatataaat gcaaacaatt   159000
gttctgtcag tcagtcatgt actggggtgt ttttaagttc catttaaacc tagatccggg   159060
ttcccagaag ggcaagccaa actcgagagc tggtgcccta agcccagtca ggcttgggtt   159120
tgaagcctgg ctccattctt gtgttttcct ctctggaact ctggcagaat atcctgcact   159180
cacttttctc atctgtaaaa tgggatggtt tagtctttga gttattgcgg gcactaaatg   159240
agatgattca cagaaatcac ctgtcgtgat ccttgctaag tagaaagtgc tccagaaatg   159300
tcagttgttg ttattagtga tacttttcac tgatactctg tctcatttca aaaagaattt   159360
gaagtaggag ataattttgc tgttcttcat tctaagggct gggctacagt gggctgttgt   159420
gacttattct gaatgtaatg ctcctgctag tgggtactgg tctggaatcc tgagttgaat   159480
cttgactcca ttcattatta ctgttggata gaatctaaaa caaataacag ttatgaaata   159540
aatatgattt catatcttgc agaagcacta aaggcaatgg agaaagtagc gagccacatc   159600
aatgagatgc agaagatcta tgaggattat gggaccgtgt ttgaccagct agtagctgag   159660
cagagcggaa cagagaagga ggtccgtgag acatctgcac cctgggagcc tagtgcatgt   159720
ggtgtggggt ctgtaggtga ccttctagat aggctgccct gttaggactt tcctggagga   159780
gaaaatgcct aagattttc ttgataacaa tgtgtctaat gaactacaca atttacatat   159840
agacatatca taaaattcat tacactggtt taaaatataa ccttatgtca cgttcacatt   159900
gtctggaaca tccatggagg gtgagagctg gcagagggtg gggtggagaa aggacatggg   159960
aactggcatg tggagtctgg ggcttttcct ttttgatttt gccttttttt tttttttttt   160020
ttaacatcaa atattggtgg ttacctgctt acttataaaa ctagtccaag caggatttga   160080
cattttctgt attttttcctt tttatctgat tgcttaattt agaatcttgt gcttctcaag   160140
ccagcatgca ggaagtagca tagtttaggg agaaaatggc aggaacagga aaggactgga   160200
gatcagtcct tcactctggc cagtttcaat gctggtgctc ttttatcagc agcccgaatg   160260
gagctcagag gtgatggatg tactagatcc caggggaaag cttacaaaag gcactctgga   160320
agaaccacgg acactggtag agttcatctt atggaaactg agttggtcac aaggcatgtc   160380
tcacctacat gtgcgtgcac tggagcaaaa tgccttcacc tttatgttat tcatcagaca   160440
```

```
cttgggtgct taactcatat tttcaaaagc tccaccgttt aaggccccat gtttacaggt  160500
atcataaaaa ttaaaccagc tgtgcttgca ttttagcaat gactgtgtgt acatcactat  160560
ctaacaagag atcatctagc ctgggatttc cgtatcttcc ttacctcctg tttttacaat  160620
ctaggtaaca gaactttcga tgggagagct tctgatgcac tctacggttt cctggttgaa  160680
tccatttctg tctctaggaa agctagaaa ggaccttgag ctcacagtat tggttagta  160740 ttccattcag aagaatgcag actgaacaga ggctgggatt acggaagaac ttcactagcc  160800
gcaccagtcc agctcactcc tgagctccag gagtcagaat tgctataatg gttggggact  160860
taacagggcc agccccaac tatttgaaac tccggcatcg ctctgcatcc tcattatctt  160920
gttctccctt ctgctgcttg gctcaggcca agtgttacag aacagatcc ctgcggctat  160980 tttgaaacct gctatctttt tcttttttctt tttctgagac gaggttttgc tcttgttgcc  161040
caggctggag tgcaatggtg tgatctctgc tcactgcaac ctccacctcc caggttcaag  161100
ctattcccct gcctaagcct cctgagtagc tgggattaca ggtgctcgcc accacgcccg  161160 gctgatttt gtattttag tagagatggg gtttcaccat gctggccaga ctggtctcga  161220
actcctgacc tcaggtgatc cacctgcctc agcctcctgg agtgctggga ttacaggcat  161280
tagccaccgt gcctggccag aaacctgcta tcttaatagt ctgctgtatt tcaaatgttt  161340
taattctgag agttgggaga acaagtgaca gtatattgtc actgagatga acacagtgtc  161400
ctcagctttc aataaaacaa agagtttaaa aaagccaaga tcaacttcta atagtagctt  161460
ttaaataagc aggtgcttct gcatagttca aatatgagcg aaagggaagt accatttatt  161520
cactcatgtt ggcagagtga ggtcttagag actcatacgt ttggagagtg ttactctgtt  161580
aagacgttca gctctagttt aaccttggaa gagtttgcat aaaataaaga cttctttct  161640 cttttccttt ctttagtttt taagagagcc gtcatactgg tttataaaga aaactgcaaa  161700
ctgaaaaaga aattggtaag gcaaaaattc attttaattt aagctaccct ttcatagctg  161760
tatcttccta ttaacgttga actgaaaagc ccactgagca ccaaggctgg gctgactgat  161820
actgcttact ctgagggtaa ctaaccccat cacatactga gagcgtttct gagtctcccc  161880
atgaaagatg tctgttttaa aagaagatat acagctgggc acggtggctc atgcctgtaa  161940
tctcagcact tgggaggct gaggcttgag cccaggaatt tgagaccagc ctggccaaca  162000
tggtgaaacc ctgcctctac caaaaataca agtaactggg tgtggtagca cgtgcctgta  162060
gtcccagcta ctcgggaggc tgaggcagga ggatcaattg agcccaggag gtggaagctg  162120
cagtgagcct tgatcatgcc actgcattcc agcctgtgcg acagagtgag accctgtcaa  162180
taaatacata aataagtaaa taaagtagat aaatactcat atgggggcct acatagaaca  162240 tcgacttta tatccctgaa aatggcccat gtttgttcca taaacatagt ctgtgaaact  162300
ttggtttatt ttcaaatgcc ttttaccttc actcagaaaa aagcaaagcc tagctgtgga  162360
taccatatgc cattggttta ccattcagag gcagcgtcag ggcgtggaag ctttggctgc  162420
tgttcttgct ttgagacctg taactgcttc tgaaccacaa ctctgcctcc gcaccttccc  162480
tagcatgtga ggtctttgag aactgggtgc gtagctgatt gacttctgtg ccctgaacac  162540
ccacatggct gctcggagac tcgcccacag ggagaacata aacttctatt cactgtgcac  162600
acatcctccc tcagtgacag cttccctaac acttttcttg gtgggccttc atgttacagc  162660
cctcgaattc ccggcctgca cacaactcta ctgacttgga cccatttaaa ttccgctggt  162720
tgatccccat ctccgcgctt caagtcagac tggggaatcc agcaggtaac tgtttcgtgc  162780
agtatgatgc cagaaaaagc atttagtag acttaactgt ggaatgtaaa ttaagaaagg  162840
```

```
accttgggga taatttttgg tgcctttat tttatagaca aggaaaatga ggacaagaga    162900
ggttgttttg atgttcctta gcagacttct gggagaaact aaatgctggt ggatagcttt    162960
ttctttgcca aatgcctttc attgtttcct tattttccct atcaatagtt ttcaacattt    163020
tcctttctgc cttgataccc taaaatgtgt tagaagaaca aagatccaca aatttatgtt    163080
tttacaaatt tagaatatag cagaaaattc cttaaggtta ggtagtactg taggtgatat    163140
aaaaagaaaa aaatctttga ctctggaaaa tgttcagaga tccttccaga gtaaccttgt    163200
tttggtgaca ggtatctggt gacagaagag gccagcaggc tgagtcatgc agtgacctgc    163260
tgggcttctg tttaactttt gtcagaagtg cttatgtttt cgagaaaatg accacatttg    163320
gggcaggcct cttttacctc aagtaccccca gctcctgttc cttccaagga aagggcaaaa    163380
ctgcaaagga ggttgaagaa taggatccac tgaatctcct cttccccaga gaggggctcc    163440
agagagaggg tgaaggcagt tcagatggag gaaaatctgc agcaggaaat gtaaaaagta    163500
accaaaaggc atttcagttc ttgtaactgt gaaaatcata catagaacaa gccacagaag    163560
aaaatgagcc aggactggga atattagact ttcttaactg atgagatttc aactttacaa    163620
gtgttcttaa ccacagcatt ttgggcaaag ttgtagactc ttgtttccat ttccttttac    163680
atagggacag aaaataattc catatgggaa ctgatccata cgaagtcaga aatagaagga    163740
cggccagaaa ccatctttca gttgtgttgc aggtatgact gacttccaaa gattaaaacc    163800
aacagaaata acatagaatt atgtctctta agggaattta tatttagtgc cctcctgaat    163860
tttgatgata tcagggtcat actccccacc ctccgaaaaa ggcaactgag gccgctagta    163920
ggagactatg ttgattaaat aaatatcaaa atcttaagag tgatcaattc tcacctcctt    163980
ctgtacggga ggccacatgg cactgctgct gggtggctgg ctggcagcct ggtccagcag    164040
gtgcaaggca caggaacaca ggcgggcgtg gaatggaagc acgatgaaca ctgtggacac    164100
ttctgctgtt ttctctcccc ccccacccag tgacagtgaa agcaaaacca acattgttaa    164160
ggtgattcgt tctattctga gggagaactt caggcgtcac ataaagtgtg aattaccact    164220
ggagaaaacg tgtaaggatc gcctggtacc tcttaagaac cgagttcctg tttcggccaa    164280
attaggtgag aattttgcta gccttgtgtt tattcaacaa aatattatga gcttctgaaa    164340
aggatatatg ctcttgtaac atagctgtga ctttttcactt tgtaagtcat cgaggtacct    164400
ttatctcctt ttaagaaacc taaacatgcc tcttgctccc agacgttcta ctgtaaaata    164460
cagccacccc caaccccccag tcccttgtct tcctacccgc tgacatagtc caaatgtacg    164520
attttgtttc ttccactaag atgtgcatgg gtccaggaca tttgttttcc tcactgctgt    164580
attcccagtg ctcagaacag tgccaggcat cctgaaggtc aatgctgaat gaagatcaag    164640
aaccttacac agagggtctc caccttctga tggttcaacc tacaatttt cgactttacc    164700
gtggtgtgaa agtgacacac attcagtaga aatcgtactt cgagtaccca gacaaccatt    164760
ctgttttttg cttctagtgc agcattcaat acatttcatg agatactcaa cacttaatta    164820
taaaacaggc cttgtgttct gcccaaccat aggctaatgt aagtgttctg agcacactga    164880
aggcaggcta ggctaagccg cagtggttag taggtacatt aaatgcattc tcgactttcc    164940
atattatcaa cttaacaatg ggttgattgg gatgtaatgc catctaagtt aaggggcctc    165000
ttatactcgt tcttaatcga tagggcacca agtaagcatt tcaaatcacg ttgttctttc    165060
tgcttgtttc taaaatttca gcttaagttt tcagaaccct atttctacat taactatttt    165120
gttattatct ttcttgtttt taggcttaga aaatgtaaaa cttcgctttt tcatgtcaaa    165180
tcagtgtgac ctcttcagat ctaccacata tttactattt tctccattgt caaaataaac    165240
```

```
tggccatcaa ataacatgc tgttattact ttgtagaaac accaaaactg agaactccct   165300
tccttctttc aatccaagag aacagaacta cacacacaca cacacacacc tataacataa   165360
aatttcagaa agttgttttg aaattccagc agagacagtt ctcatatgag agataaagag   165420 catttttctag gctgggcatg gtggctcatg cctgtaatcc cagcactttg ggaggccaag   165480
gcaggtggat cccttgagct cttgagaaca ggagtttgag accaacctgg caacatggc   165540 aaaaccccat ctctacaaaa aaatataaa aattagccag gcgtgatcat gcgcacctat   165600
agtcccaact actcaggagg ctgagatggg aggatcactt gagcccagga ggcggaggtt   165660
gcagtgagca gagatcacac cactgcactc cagcctgggt ggcagagcaa gacactgtct   165720
ttaaaaaaaa agggggggg aggggcattt tctacttta attgagcagc aagggaaatc   165780
cacaaggtga aagatgcat aggaatatgg tgtgatcttc atgatcaaat tacaaagcac   165840
cttagtgaaa gaaaggagcc tagatttatt attaccaatt aacttttcaa cttactcctt   165900
ggcaaaataa gaatcttagc ccatgtagta gtttctagtg tctagttcta tttacataat   165960
tgagctctgg taatctaaaa atgctgaatt gcctaactta caactgtaaa cctaagtcaa   166020
aaatgtccat gttttcagta gctacatttt tgcctaatta ccaggatagt tgctaactga   166080
agtcatatca taaaataaaa tcttaatgtt aaatcttaca caagctttga ggcaaacatt   166140
acacattgtg taacctgttt ctgtatcaca gcgaaatgtg tttttctcac tgtagcttca   166200
tccaggtctt taaaagtcct gaagaattcc tccagcaacg agtggaccgg tgagactggc   166260
aagggaacct tgctggactc tgacgagggc agcttgagca gcggcaccca gagcagcggc   166320
tgccccacgg ctgagggcag gcaggactcc aagagcactt ctcccgggaa atacccacac   166380
cccggcttgg cagattttgc cgacaatctc atcaaagaga gtgacatcct gagcgatgaa   166440
gatgatgacc accgtcagac tgtgaagcag gcagccccta ctaaagacat cgaaattcag   166500
ttccagagac tgaggatttc cgaggaccca gacgttcacc ccgaggctga gcagcagcct   166560
ggcccggagt cgggtgaggg tcagaaagga ggagagcagc ccaaactggt ccgggggcac   166620
ttctgcccca ttaaacgaaa agccaacagc accaagaggg acagaggaac tttgctcaag   166680
gcgcagatcc gtcaccagtc ccttgacagt cagtctgaaa atgccaccat cgacctaaat   166740
tctgttctag agcgagaatt cagtgtccag agtttaacat ctgttgtcag tgaggagtgt   166800
ttttatgaaa cagagagcca cggaaaatca tagtatgatt caatccagat atgggttaaa   166860 ttcctcatttt tacttttaaa ctggtggtaa agtggaaatt gcaaaaaaaa aaaaaaaaa   166920 aaactgttca ttcctgggtt ttgtgcagta tacattttcc cacaaaatgg ttgtaaagat   166980
ttaagttatt ttaattttatt gtggatcaga aacctagatg aaactggtca gaatctgtaa   167040
attacttagt ttatatccac tttgagcagg tatcaaatga tttaggatcc ttaaaattac   167100
attctaataa ttaagttatg tggaaaaagt aaggctgggg aagtcgtgat taatagtttt   167160
caaagggcca ttttttaaaa tcctctgggc attttcttc agctgtttgt tagttttgc   167220 tttatttaaa gcatatttaa gttatttaa tgtggtttag gggcaaaatg tgcagatact   167280
tcatttttgt aagatagatt gtaatagatg ctgtttatac taaacatgtc ataactatct   167340
atacagtata tattaaaaga aagcttgtac tgtatcttat ttgatgatat ttattttctc   167400
tgccaagctg tatagtaaaa ggaaaataag tcaca                              167435
```

```
<210> SEQ ID NO 2
<211> LENGTH: 3344
<212> TYPE: DNA
<213> ORGANISM: Homo sapiens
```

<400> SEQUENCE: 2

```
gagacaacgt gtgtcttaca catctcccaa cagccgactt agatgtgatc cgttctccca      60
gagggagcag gtttctttga acttttcctt tttatgtaca gcatagtgct gagcagatca     120
ctgcactgtg caggagtttt aacgacagtc aggccgacgg catggaagga ccgcgggaga     180
atcaggatcc tcctccgagg cctctggccc gccacctgtc tgatgcagac cgcctccgca     240
aagtcatcca ggagcttgtg gacacagaga agtcctacgt gaaggatttg agctgcctct     300
ttgaattata cttggagcca cttcagaatg agacctttct tacccaagat gagatggagt     360
cacttttttgg aagtttgcca gagatgcttg agtttcagaa ggtgtttctg agaccctgg     420
aggatgggat ttcagcatca tctgacttta cacccctaga aaccccctca cagtttagaa     480
aattactgtt ttcccttgga ggctcttttcc tttattacgc ggaccacttt aaactgtaca     540
gtggattctg tgctaaccat atcaaagtac agaaggttct ggagcgagct aaaactgaca     600
aagccttcaa ggcttttctg gacgcccgga accccaccaa gcagcattcc tccacgctgg     660
agtcctacct catcaagccg gttcagagag tgctcaagta cccgctgctg ctcaaggagc     720
tggtgtccct gacggaccag gagagcgagg agcactacca cctgacggaa gcactaaagg     780
caatggagaa agtagcgagc cacatcaatg agatgcagaa gatctatgag gattatggga     840
ccgtgtttga ccagctagta gctgagcaga gcggaacaga gaaggaggta acagaacttt     900
cgatgggaga gcttctgatg cactctacgg tttcctggtt gaatccattt ctgtctctag     960
gaaaagctag aaaggacctt gagctcacag tatttgtttt taagagagcc gtcatactgg    1020
tttataaaga aaactgcaaa ctgaaaaaga aattgccctc gaattcccgg cctgcacaca    1080
actctactga cttggaccca tttaaattcc gctggttgat ccccatctcc gcgcttcaag    1140
tcagactggg gaatccagca gggacagaaa ataattccat atgggaactg atccatacga    1200
agtcagaaat agaaggacgg ccagaaacca tctttcagtt gtgttgcagt gacagtgaaa    1260
gcaaaaccaa cattgttaag gtgattcgtt ctattctgag ggagaacttc aggcgtcaca    1320
taaagtgtga attaccactg gagaaaacgt gtaaggatcg cctggtacct cttaagaacc    1380
gagttcctgt ttcggccaaa ttagcttcat ccaggtcttt aaaagtcctg aagaattcct    1440
ccagcaacga gtggaccggt gagactggca agggaacctt gctggactct gacgagggca    1500
gcttgagcag cggcacccag agcagcggct gccccacggc tgagggcagg caggactcca    1560
agagcacttc tcccgggaaa tacccacacc ccggcttggc agattttgct gacaatctca    1620
tcaaagagag tgacatcctg agcgatgaag atgatgacca ccgtcagact gtgaagcagg    1680
gcagccctac taaagacatc gaaattcagt tccagagact gaggatttcc gaggacccag    1740
acgttcaccc cgaggctgag cagcagcctg gcccggagtc gggtgagggt cagaaaggag    1800
gagagcagcc caaactggtc cgggggcact tctgccccat taaacgaaaa gccaacagca    1860
ccaagaggga cagaggaact tgctcaagg cgcagatccg tcaccagtcc cttgacagtc    1920
agtctgaaaa tgccaccatc gacctaaatt ctgttctaga gcgagaattc agtgtccaga    1980
gtttaacatc tgttgtcagt gaggagtgtt tttatgaaac agagagccac ggaaaatcat    2040
agtatgattc aatccagata tgggttaaat tcctcatttt acttttaaac tggtggtaaa    2100
gtggaaattg caaaaaaaaa aaaaaaaaa ctgttcattc ctgggttttg tgcagtatac    2160
attttcccac aaaatggttg taaagattta agttatttta atttattgtg gatcagaaac    2220
ctagatgaaa ctggtcagaa tctgtaaatt acttagttta tatccacttt gagcaggtat    2280
caaatgattt aggatcctta aaattacatt ctaataatta agttatgtgg aaaaagtaag    2340
```

-continued

```
gctgggaagt cgtgattaat agttttcaaa ggccattttt taaaatcctc tgggcatttt    2400 cttttcagctg tttgttagtt tttgctttat ttaaagcata tttaagttat ttaatgtgg    2460 tttaggggca aaatgtgcag atacttcatt tttgtaagat agattgtaat agatgctgtt    2520
tatactaaac atgtcataac tatctataca gtatatatta aaagaaagct tgtactgtat    2580
cttatttgat gatatttatt ttctctgcca agctgtatag taaaaggaaa ataagtcaca    2640
tctggtcatt ggcatttgta tcgtcattct gtaaagacaa aagagtacct atataagaag    2700
ctccacgtag tgcaaatcga catctggtag gctgctcgcc cccaggcagc agctagagtc    2760
tgtaattctc tgcgtcatcc tcttcttttt cttcattttt gcttttcttt cgcttgagtt    2820
cttctctgaa attatatgca aagagttgtg ggtcttcatc acacattttt ctgtatacat    2880
cacagaggct cttaaagtgt gagatggaga gctggtgggg ccgaagagta gggtctatgt    2940
ctgccaactc taacagcctg cccgtgcttt ccaagcgctg cgcttcaggg aataacattc    3000
tgagccctcg atggcagtat ttccttcgga actgaaatac attctgaacc acttttttcca   3060 ccagcttgaa tggctgctct atcttgggct gtatcaaggg agtgaagtgc accacgccca    3120
cgtccacctt cgttgtaagc aaacatatta tcattctgtg gcatgatatg tggcatagtg    3180
tgatcaatca actcatcctt gtaaaacagg aagatgggct gtcaacagcc tgttttcata    3240
aacagacctt tccacgtact tcggtttcat ctctaggcat ggaagatggt acattctgga    3300
ttcgcaaatg acatggagaa atcagccggc tgcacctgtt ctct                     3344
```

<210> SEQ ID NO 3
<211> LENGTH: 626
<212> TYPE: PRT
<213> ORGANISM: Homo sapiens

<400> SEQUENCE: 3

```
Met Glu Gly Pro Arg Glu Asn Gln Asp Pro Pro Arg Pro Leu Ala
1               5                  10                  15

Arg His Leu Ser Asp Ala Asp Arg Leu Arg Lys Val Ile Gln Glu Leu
            20                  25                  30

Val Asp Thr Glu Lys Ser Tyr Val Lys Asp Leu Ser Cys Leu Phe Glu
        35                  40                  45

Leu Tyr Leu Glu Pro Leu Gln Asn Glu Thr Phe Leu Thr Gln Asp Glu
    50                  55                  60

Met Glu Ser Leu Phe Gly Ser Leu Pro Glu Met Leu Glu Phe Gln Lys
65                  70                  75                  80

Val Phe Leu Glu Thr Leu Glu Asp Gly Ile Ser Ala Ser Ser Asp Phe
                85                  90                  95

Asn Thr Leu Glu Thr Pro Ser Gln Phe Arg Lys Leu Leu Phe Ser Leu
            100                 105                 110

Gly Gly Ser Phe Leu Tyr Tyr Ala Asp His Phe Lys Leu Tyr Ser Gly
        115                 120                 125

Phe Cys Ala Asn His Ile Lys Val Gln Lys Val Leu Glu Arg Ala Lys
    130                 135                 140

Thr Asp Lys Ala Phe Lys Ala Phe Leu Asp Ala Arg Asn Pro Thr Lys
145                 150                 155                 160

Gln His Ser Ser Thr Leu Glu Ser Tyr Leu Ile Lys Pro Val Gln Arg
                165                 170                 175

Val Leu Lys Tyr Pro Leu Leu Leu Lys Glu Leu Val Ser Leu Thr Asp
            180                 185                 190

Gln Glu Ser Glu Glu His Tyr His Leu Thr Glu Ala Leu Lys Ala Met
        195                 200                 205
```

```
Glu Lys Val Ala Ser His Ile Asn Glu Met Gln Lys Ile Tyr Glu Asp
    210                 215                 220
Tyr Gly Thr Val Phe Asp Gln Leu Val Ala Glu Gln Ser Gly Thr Glu
225                 230                 235                 240
Lys Glu Val Thr Glu Leu Ser Met Gly Glu Leu Leu Met His Ser Thr
                245                 250                 255
Val Ser Trp Leu Asn Pro Phe Leu Ser Leu Gly Lys Ala Arg Lys Asp
            260                 265                 270
Leu Glu Leu Thr Val Phe Val Phe Lys Arg Ala Val Ile Leu Val Tyr
        275                 280                 285
Lys Glu Asn Cys Lys Leu Lys Lys Leu Pro Ser Asn Ser Arg Pro
    290                 295                 300
Ala His Asn Ser Thr Asp Leu Asp Pro Phe Lys Phe Arg Trp Leu Ile
305                 310                 315                 320
Pro Ile Ser Ala Leu Gln Val Arg Leu Gly Asn Pro Ala Gly Thr Glu
                325                 330                 335
Asn Asn Ser Ile Trp Glu Leu Ile His Thr Lys Ser Glu Ile Glu Gly
            340                 345                 350
Arg Pro Glu Thr Ile Phe Gln Leu Cys Cys Ser Asp Ser Glu Ser Lys
        355                 360                 365
Thr Asn Ile Val Lys Val Ile Arg Ser Ile Leu Arg Glu Asn Phe Arg
    370                 375                 380
Arg His Ile Lys Cys Glu Leu Pro Leu Glu Lys Thr Cys Lys Asp Arg
385                 390                 395                 400
Leu Val Pro Leu Lys Asn Arg Val Pro Val Ser Ala Lys Leu Ala Ser
                405                 410                 415
Ser Arg Ser Leu Lys Val Leu Lys Asn Ser Ser Asn Glu Trp Thr
            420                 425                 430
Gly Glu Thr Gly Lys Gly Thr Leu Leu Asp Ser Asp Glu Gly Ser Leu
        435                 440                 445
Ser Ser Gly Thr Gln Ser Ser Gly Cys Pro Thr Ala Glu Gly Arg Gln
    450                 455                 460
Asp Ser Lys Ser Thr Ser Pro Gly Lys Tyr Pro His Pro Gly Leu Ala
465                 470                 475                 480
Asp Phe Ala Asp Asn Leu Ile Lys Glu Ser Asp Ile Leu Ser Asp Glu
                485                 490                 495
Asp Asp Asp His Arg Gln Thr Val Lys Gln Gly Ser Pro Thr Lys Asp
            500                 505                 510
Ile Glu Ile Gln Phe Gln Arg Leu Arg Ile Ser Glu Asp Pro Asp Val
        515                 520                 525
His Pro Glu Ala Glu Gln Gln Pro Gly Pro Glu Ser Gly Glu Gly Gln
    530                 535                 540
Lys Gly Gly Glu Gln Pro Lys Leu Val Arg Gly His Phe Cys Pro Ile
545                 550                 555                 560
Lys Arg Lys Ala Asn Ser Thr Lys Arg Asp Arg Gly Thr Leu Leu Lys
                565                 570                 575
Ala Gln Ile Arg His Gln Ser Leu Asp Ser Gln Ser Glu Asn Ala Thr
            580                 585                 590
Ile Asp Leu Asn Ser Val Leu Glu Arg Glu Phe Ser Val Gln Ser Leu
        595                 600                 605
Thr Ser Val Val Ser Glu Glu Cys Phe Tyr Glu Thr Glu Ser His Gly
    610                 615                 620
Lys Ser
625
```